(12) United States Patent  
Bonnette et al.

(10) Patent No.: US 6,676,637 B1  
(45) Date of Patent: *Jan. 13, 2004

(54) SINGLE OPERATOR EXCHANGE FLUID JET THROMBECTOMY METHOD

(75) Inventors: Michael J. Bonnette, Minneapolis, MN (US); Hieu V. Le, Brooklyn Park, MN (US); John Edward Morris, Minneapolis, MN (US); Stephen E. Weisel, Montrose, MN (US); Debra M. Kozak, Forest Lake, MN (US); Robert G. Dutcher, Maple Grove, MN (US)

(73) Assignee: Possis Medical, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/888,454

(22) Filed: Jun. 25, 2001

Related U.S. Application Data

(60) Continuation-in-part of application No. 09/356,783, filed on Jul. 16, 1999, which is a division of application No. 09/019,728, filed on Feb. 6, 1998, now Pat. No. 5,989,210.

(51) Int. Cl.⁷ .............................................. A61M 5/178
(52) U.S. Cl. ......................... 604/165.02; 604/165.04; 604/167.06; 604/22; 604/43
(58) Field of Search .................... 604/28, 30, 500, 604/506, 507–510, 22, 27, 35, 39, 40, 43, 73, 118, 131, 151, 158, 164.09, 164.13, 167.06, 275; 606/159, 127, 128, 190, 191, 194

(56) References Cited

U.S. PATENT DOCUMENTS

| | | | | |
|---|---|---|---|---|
| 5,370,609 A | * | 12/1994 | Drasler et al. | 604/22 |
| 5,989,210 A | * | 11/1999 | Morris et al. | 604/22 |
| 6,022,336 A | * | 2/2000 | Zadno-Azizi et al. | 604/96 |
| 6,096,001 A | * | 8/2000 | Drasler et al. | 604/22 |
| 6,224,570 B1 | * | 5/2001 | Le et al. | 604/165.02 |
| 6,375,635 B1 | * | 4/2002 | Moutafis et al. | 604/43 |

* cited by examiner

Primary Examiner—Glenn K. Dawson  
Assistant Examiner—Jennifer Maynard  
(74) Attorney, Agent, or Firm—Hugh D. Jaeger

(57) ABSTRACT

A single operator exchange fluid jet thrombectomy method employing a single operator exchange fluid jet thrombectomy device having an outer catheter assembly and separable and exchangeable components in the form of an inner catheter assembly allowing functioning as a rheolytic thrombectomy catheter or as a crossflow thrombectomy catheter. The outer catheter assembly is common to any mode of usage and includes a guide catheter having a lumen through which a guidewire and the greater portion of a hypo-tube carrying a jet emanator and a flow director are passed and advanced. In the method, thrombus is dislodged, entrained, and broken into pieces by fluid jets and evacuated through the lumen of the guide catheter.

14 Claims, 51 Drawing Sheets

SINGLE OPERATOR EXCHANGE FLUID JET THROMBECTOMY METHOD

CROSS REFERENCES TO CO-PENDING APPLICATIONS

This patent application is a continuation-in-part of Ser. No. 09/356,783, entitled "Rheolytic Thrombectomy Catheter and Method of Using Same", filed on Jul. 16, 1999, pending, which is a divisional of Ser. No. 09/019,728, entitled "Rheolytic Thrombectomy Catheter and Method of Using Same", filed on Feb. 06, 1998, U.S. Pat. No. 5,989,210.

BACKGROUND OF THE INVENTION

1. Field of the Invention

The present invention relates to a method of treating matter in a body vessel or cavity, especially to removing undesired obstructing material, such as thrombus, from a body vessel or cavity having an obstruction, by employing an interchangeable and separable catheter system for alternatively incorporating the principles of a rheolytic thrombectomy catheter or the principles of a crossflow thrombectomy catheter, or of the simultaneous use of the principles of both the rheolytic thrombectomy catheter and the crossflow thrombectomy catheter.

More particularly, the present invention relates to a method of treatment of the human body by means of an elongated device which may be a single catheter assembly or a multiple component catheter assembly and which is suitable for use through percutaneous or other access, for endoscopic procedures, or for intraoperative use in either open or limited access surgical procedures. Still more particularly, the present invention relates to a method of treatment of the human body involving use of an elongated device in the form of a rheolytic thrombectomy catheter or, alternately, in the form of a fluid jet thrombectomy catheter, the latter hereinafter termed crossflow thrombectomy catheter, and having a commonly used outer catheter assembly, each device being incorporated for fragmentation and removal of thrombus or other unwanted material from blood vessels or body cavities, and each device using high velocity saline (or other suitable fluid) jets to macerate the thrombus or other unwanted material. The elongated device bears certain similarities to a known waterjet thrombectomy catheter and can be used as such, but differs therefrom in several material respects, a major distinction being in the provision of interchangeable alternate means which produce inwardly directed jets with or without crossflow jets. The crossflow jets create a recirculation flow pattern optimized for clearing a large cross section of mural thrombus or other similar material, the name crossflow thrombectomy catheter deriving from this major distinction. Further, the method of the present invention also involves a system constituted either by the combination of the elongated device with both pressurized fluid source means and exhaust regulation means or by the combination of the elongated device with only pressurized fluid source means.

2. Description of the Prior Art

Procedures and devices have been developed for ease in removing tissue and various deposits. Several such devices employ a jet of saline as the working tool to help break up the tissue deposit and further provide a suction means to remove the deposit. U.S. Pat. No. 5,135,482 to Neracher describes a hydrodynamic device for removal of organic deposit from a human vessel. A supply of saline is delivered by a high pressure duct to the distal end of a catheter. The saline exits the duct as a jet that is directed generally forward and directly toward the tissue to be broken up. The duct is contained within and can move axially with respect to a hose that is positioned around the duct. A vacuum suction is applied to the hose to remove the debris that is created from the broken-up tissue. This device is not intended to pass through tortuous pathways found in the fragile vessels of the body, and any attempt to employ the device for such purpose would be far too traumatic to the patient.

Another drainage catheter, described by Griep in U.S. Pat. No. 5,320,599, has a discharge channel and a pressure channel. The channels are formed into a single catheter tube such that the two tubes are fixed with respect to each other.

Waterjet thrombectomy catheters have been described in which a distal-to-proximal-directed waterjet(s) flow(s) past a window, orifice or gap at the distal end of the catheter, re-entering the catheter and pushing flow through an evacuation lumen. When placed in a vessel containing thrombus and activated, the high velocity jet(s) will entrain surrounding fluid and thrombus into the window, orifice or gap region, where the high shear forces of the jet(s) will macerate the thrombus. The macerated particles will be removed from the body by the pressure generated on the distal end of the evacuation lumen by the impingement of the high velocity waterjet(s).

A limitation of these waterjet thrombectomy catheters has been the inability to remove organized, wall-adherent thrombus from large vessels. In accordance with the method of the present invention, the single operator exchange fluid jet thrombectomy device described and utilized in the method overcomes this limitation by optimizing the recirculation pattern at the tip of the device to increase the drag force exerted on the mural thrombus to break it free from the vessel wall and allow it to be removed by the device.

Methods practiced with prior art devices often required the use of more than one operator where one operator must stabilize the guidewire while the second operator introduces the catheter over the guidewire into the anatomy.

The method of the present invention overcomes the disadvantages of the procedures using current devices by relying on an interchangeable catheter system utilizing either the rheolytic thrombectomy catheter or the crossflow thrombectomy catheter, each of which can be operated by one practitioner, and which offers multiple advantages over previous rheolytic thrombectomy catheter designs. More specifically, the method of the present invention is effectual for removal of unwanted deposits in the body, such as, but not limited to, deposits in bile ducts, the brain or other hematomas, and brain ventricles, for example.

SUMMARY OF THE INVENTION

The present invention, a single operator exchange fluid jet thrombectomy method, relies on use of a single operator exchange fluid jet thrombectomy device, which is a surgical device for removal of material such as thrombus from a vessel or other body cavity. As shown in one or more embodiments, the single operator exchange fluid jet thrombectomy device can function as a rheolytic thrombectomy catheter for removing tissue from a vessel or other body cavity and includes an outer catheter assembly common to any mode of operation, the commonly used outer catheter assembly of which is comprised of a manifold and a first tube or guide catheter having a lumen with an open distal end, the lumen being of a diameter sufficient to allow passage of an inner catheter assembly. One such inner catheter assembly as incorporated in use with the single operator exchange fluid jet thrombectomy device is comprised of a high pressure second tube having a high pressure lumen and a geometrically configured distally located jet emanator having one or more rearwardly directed orifices for directing one or more jets of saline toward the distal end of a flow director, a proximally located transitional stop fixed to the second tube adjacent to the second tube proximal end, and an exhaust tube. The inner catheter assembly is movable axially within the outer catheter assembly such that the proximally located transitional stop engages the proximally located stationary stop to hold the jet emanator in a desired relationship with respect to the distal end of the outer catheter assembly.

The single operator exchange fluid jet thrombectomy device provides a catheter combination for use as a rheolytic thrombectomy catheter including the first tube or guide catheter, being a part of a common use outer assembly, the first tube or guide catheter having a proximal end, a manifold attached thereto, an open distal end, and a lumen extending between the proximal end and the open distal end; the second tube, being a part of an inner catheter assembly, the second tube being separable from the first tube or guide catheter and being insertable within the lumen of the first tube or guide catheter, the second tube having a proximal end, a distal end, and a lumen extending between the proximal end and the distal end; a flow director having an inner body and an exhaust tube which may or may not be expandable, each being located near but not at the second tube distal end, a pressure operated sealable or closely fit annulus between the outer surface of the exhaust tube and the interior annular surface of the first tube or guide catheter, a jet emanator integrally formed at the distal end of the second tube or attached thereto by a bonding operation into which at least one jet orifice is machined or otherwise formed on the proximal side thereof to create a jet emanator for directing fluid proximally for thrombus ablation and subsequently through a lumen in the flow director and the lumen of the first tube or guide catheter, being also a part of the inner catheter assembly, the jet emanator and flow director, including the inner body thereof, being capable of passage through the lumen of the first tube or guide catheter and over a guidewire, and being characterized by the ability to provide a localized region of low pressure associated with a liquid flow directed generally proximally and into the inner body, into an exhaust tube, and into the lumen of the first tube or guide catheter through the distal end of the first tube or guide catheter. A variable displacement distance means for indexing an appropriate positional and variable relationship of the jet emanator to the distal end of the first tube or guide catheter is provided. A stop means is provided for limiting movement of the second tube and preferably includes a proximally located hemostasis nut/stop at the proximal end of a manifold of the outer catheter assembly and a proximally located filter housing/high pressure connection/stop assembly projecting outwardly from the proximal end of the second tube. When the second tube is advanced within the first tube or guide catheter, fluoroimaging can be incorporated to provide adequate spacing and relationship between the jet emanator and the distal end of the first tube or guide catheter. This relationship is also referred to as variable displacement distance. Lateral positioning of the second tube within the first tube or guide catheter is readily accomplished during the first stage (insertion) in an unpressurized operational mode where the sealable or closely fit annulus is suitably sized to allow easy unrestricted passage of the second tube within and through the first tube or guide catheter. A representative exhaust tube is shown in many embodiments with additional reference to the following exhaust tube types including, but not limited to, an exhaust tube which can be compliant expandable where the diameter of the exhaust tube depends on applied pressure and subsequent restriction by the guide catheter, a non-compliant expandable exhaust tube where the diameter of the exhaust tube is dependent on the designed diameter or the exhaust tube can be not expandable, but closely fit to the first tube or guide catheter. During the operational pressurized mode, jetted saline causes an expandable exhaust tube to expand, thus partially or fully closing, restricting, modifying or eliminating the open annulus to pressure seal the first tube or guide catheter to the second tube, but still allowing movement relative to each other. In the alternative, a closely fit annulus incorporating a non-expandable exhaust tube offers partial but effective restrictive closing to substantially pressure seal or close the first tube or guide catheter to the second tube.

The above embodiment is utilized in a method of removing thrombus from an obstructed body vessel. The method includes the steps of:

a. providing a guidewire and an outer catheter assembly including a manifold, a first tube or guide catheter having an interior annular surface, a distal end, and an externally located stationary hemostasis nut/stop positioned at the manifold proximal end;

b. advancing the first tube or guide catheter proximal to a vascular site containing thrombus;

c. advancing the guidewire through the first tube or guide catheter and past the vascular site containing thrombus;

d. providing an inner catheter assembly including a second tube carrying a jet emanator at its distal end, a flow director including an expandable or non-expandable exhaust tube proximal of the jet emanator, and a transitional filter housing/high pressure connection/stop assembly at its proximal end;

e. advancing the inner catheter assembly to a desired position within the first tube or guide catheter, so that a gap or space proximal to the jet emanator extends past the distal end of the first tube or guide catheter, while the proximal end of the flow director remains proximal to the distal end of the first tube or guide catheter;

f. providing a high pressure saline supply to the second tube so as to cause at least one jet of saline to emanate from the jet emanator and to entrain thrombus into the gap or space where the thrombus is macerated and then pushed through the flow director and into the first tube or guide catheter for removal from the body; and, g. providing impingement of at least one jet on the interior annular surface of an exhaust tube to create sufficient stagnation pressure to expand the exhaust tube against the interior annular surface of the first tube or guide catheter or utilize a closely fit annulus and force evacuation of debris through the flow director and the first tube or guide catheter out of the body with no need for additional suction.

In the method, the inner catheter assembly can be moved axially relative to both the first tube or guide catheter and guidewire to facilitate distal and proximal movement of the inner catheter assembly to remove thrombus distributed axially throughout the vasculature.

An alternate embodiment useful in the method includes a crossflow/flow director inserted into the common outer catheter assembly to function substantially as described above, but to include the features and functions of a crossflow thrombectomy catheter.

One significant aspect and feature of the method of the present invention is the use of a single operator exchange fluid jet thrombectomy device operable by one practitioner.

Another significant aspect and feature of the method of the present invention is the use of a single operator exchange fluid jet thrombectomy device having an outer catheter assembly which can accommodate various inner catheter assemblies configured to function either as a rheolytic thrombectomy catheter or as a crossflow thrombectomy catheter.

Another significant aspect and feature of the method of the present invention is the provision of a transitional filter housing/high pressure connection/stop assembly on the proximal end of the second tube which impinges a hemostasis nut/stop on the manifold to position the jet emanator at a defined distance beyond the distal end of the guide catheter.

Other significant aspects and features of the method of the present invention are the provisions of a transitional filter housing/high pressure connection/stop assembly proximally located at the end of the inner catheter assembly and a stationary hemostasis nut/stop proximally located on the outer catheter assembly which engage to prevent the inner catheter assembly from being excessively advanced, so that the exhaust tube proximal end does not become disengaged from the distal end of the first tube or guide catheter.

A further significant aspect and feature as found in additional embodiment groups employed in the method of the present invention is an annulus which is open for lateral movement of the inner catheter assembly within the outer catheter assembly during the initial unpressurized mode (insertion) and which can be modulated to a partially or fully closed position and sealed by jetted saline during the ablation process to provide maximum proximally directed saline flow with minimum or no leakage between the outer and inner catheter assemblies when thrombotic tissue is broken up and carried proximally.

Another significant aspect and feature of the method of the present invention is the provision of a flow director which can use either a compliant expandable, a non-compliant expandable, a non-expandable, non-compliant close fit, or a combination compliant/non-compliant exhaust tube.

Yet another significant aspect and feature of the method of the present invention is the ability to incorporate various emanator shapes, styles and designs.

Another significant aspect and feature of the method of the present invention is the ability to reduce cost aspect since effluent outflow or exhaust can be collected using a standard Y-connector.

Having thus described embodiments and significant aspects and features pertaining to the method of the present invention, it is the principal object of the present invention to provide a single operator exchange fluid jet thrombectomy method to remove undesired obstructing material such as thrombus from a body vessel or other body cavity.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
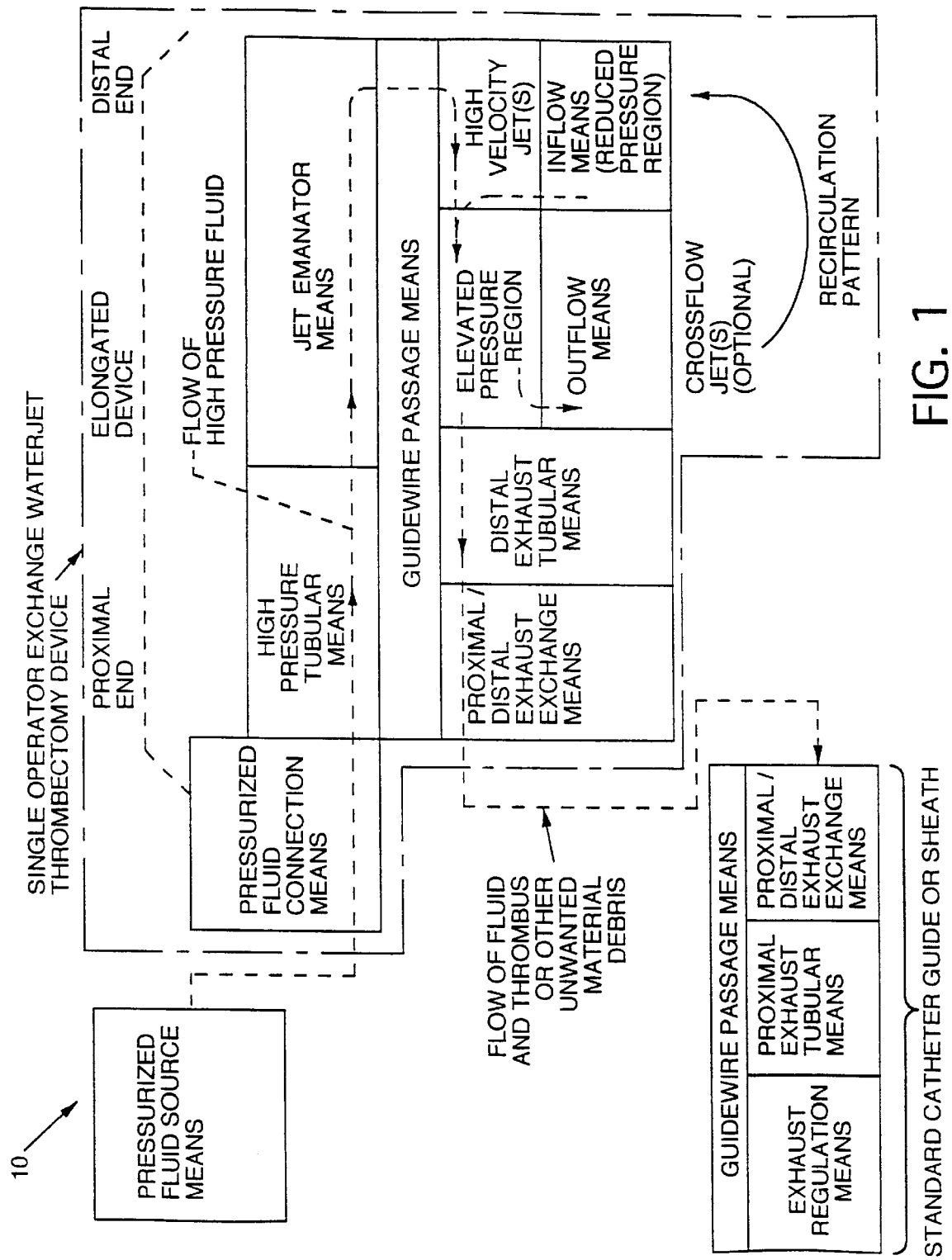
FIG. 1 is a simplified block diagram view of a single operator exchange fluid jet thrombectomy device useful in the method of the present invention.

FIG. 1 illustrates in block diagram form a single operator exchange fluid jet thrombectomy device 10 for use in the method of the present invention showing the interrelation of the various functional means thereof for use in removing thrombus or other unwanted material from a body vessel or cavity.

The major components of the system include an elongated device in the form of a single operator exchange fluid jet thrombectomy device, a pressurized fluid source means, and, optionally, an exhaust regulation means connected to a collection system (not shown).

The elongated device includes first and second tubular means each having a proximal end and a distal end. The second tubular means is in the form of a high pressure tubular means having pressurized fluid connection means providing a fluid connection permanently or detachably coupled to its proximal end and jet emanator means at its distal end, the pressurized fluid connection means being connectible to the pressurized fluid source means. The first tubular means is in the form of either an exhaust tubular means, as shown, or other tubular means (not shown in FIG. 1 but described in detail in relation to FIGS. 2 and 3) which serves as an alternative to an exhaust tubular means in those instances when exhausting is not necessary or desired. When in the form of an exhaust tubular means, the first tubular means is usually associated with exhaust regulation means, although an exhaust regulation means is not essential. Whether in the form of an exhaust tubular means or other tubular means, the first tubular means includes outflow means and inflow means which in concert with high velocity jet(s) produced by the jet emanator means create rheolytic fluid flow or create optional crossflow jet(s) that establish a flow recirculation pattern, depending on the style of second tubular means.

The optional outflow means (crossflow) consists of one or more outflow orifices through which saline, blood or other fluid or a mixture thereof with macerated thrombus or other unwanted material debris flows from a region of higher pressure within the exhaust tubular means or other tubular means to outside the exhaust tubular means or other tubular means. The one or more outflow orifices are typically somewhat downstream from the high velocity region of the high velocity jet(s) where the velocities are lower and the mass flow rate is greater due to entrained fluid; and flow of fluid with or without macerated debris typically flows through the one or more outflow orifices with a component in the radial direction, creating crossflow jet(s). The outflow orifices may be round, elliptical, conical, slits, gaps between components, or other shapes or designs.

The optional inflow means (crossflow) consists of one or more inflow orifices through which the high velocity jet(s) draw in by fluid entrainment blood or other fluid from a body vessel or cavity, including thrombus or other unwanted material which may be present in the blood or other fluid.

The one or more inflow orifices are typically near the high velocity region of the high velocity jet(s) where entrainment forces are great. The inflow orifices may be round, elliptical, conical, slits, gaps between components, or other shapes or designs.

The high pressure tubular means comprises an elongated structure having at least one passage or lumen along the length thereof suitable for passage of high pressure fluid. The elongated structure can be tubing with a circular or non-circular cross section and can be made of high strength polymeric material such as polyimide, metallic material such as stainless steel or titanium, or composite material such as fiber-reinforced material or a layered structure composed of layers of different materials.

The exhaust tubular means comprises an elongated structure having at least one passage or lumen along the length thereof suitable for passage of fluid and thrombus or other unwanted material debris. The elongated structure can be tubing with a circular or non-circular cross section and can be made of polymeric material such a polyethylene, polyester, polyurethane, or polyether block amide; high strength polymeric material such as polyimide; metallic material such as stainless steel or titanium; or composite material such as fiber-reinforced polymeric material or a layered structure composed of layers of different materials. Further, the elongated structure may have an attached structure near its distal end such as a chamber or manifold to accommodate the inflow means and optional outflow means.

The other tubular means comprises an elongated structure having at least one passage or lumen along the length thereof suitable for passage of fluid. The elongated structure can be tubing with a circular or non-circular cross section or may resemble a shorter chamber such as a manifold, molded or constructed of multiple components. Suitable materials for the other tubular means are polymeric material such as polyethylene, polyester, or polyurethane; high strength polymeric material such as polyimide; metallic material such as stainless steel or titanium; or composite material such as fiber-reinforced polymeric material or a layered structure composed of layers of different materials.

If desired, isolation means (not shown) can be provided as part of the elongated device to isolate the region of the body vessel or cavity being treated, although this is not always required. Isolation means can include balloons, filters, baskets, membranes, blood pressure modification, fluid flow control, or other occlusion devices such as are known in the art. Isolation means can limit passage of debris in the blood vessel, limit the flow of blood in the area of the elongated device, or confine the recirculation area. Also if desired, additional tubular means can be provided for communication between the proximal end and the distal end of the elongated device, such as for passage of fluid or other material or for passage of devices such as guidewires, catheters, or imaging tools, or for actuation of isolation means, for inflation of a balloon, or for passage of medication or body fluids. The additional tubular means (not shown) comprises an elongated structure having at least one passage or lumen along the length thereof; for example, the elongated device can include a multiple-lumen tube, in which one lumen functions as the high pressure tubular means, a second lumen functions as the exhaust tubular means, and one or more additional lumens function as the additional tubular means which communicates between the proximal and distal ends of the elongated device.

The pressurized fluid source means includes fluid such as saline and one or more pumps or pressure intensifiers or pressurized fluid containers for delivering the fluid under pressure to the high pressure tubular means through the pressurized fluid connection means coupled to the proximal end thereof. The fluid can be provided at a single pressure or at multiple pressures, at variable or adjustable pressure, and at a steady flow or unsteady flow such as pulsatile flow.

The exhaust regulation means, when present, comprises structural components which increase, decrease, limit, or adjust the rate of flow of fluid and thrombus or other unwanted material debris along the exhaust tubular means and can be one or more pumps such as roller pumps or peristaltic pumps, clamps, restrictors, or other devices to influence the fluid flow rate. The exhaust regulation means can regulate exhaust at a predetermined or user-adjustable flow rate which can be correlated with or independent of the rate of flow of the pressurized fluid flowing along the high pressure tubular means. Further, the exhaust regulation means can have pressure measurement or flow rate measurement capabilities. The exhaust regulation means is connected to a suitable collection system (not shown).

The system is placed in operation by first inserting the first tubular means into a body vessel or cavity and advancing it to a site of thrombus or other unwanted material in the body vessel or cavity followed by insertion of a guidewire which is inserted to or past the site of the thrombus or other unwanted material. Subsequently, the second tubular means is advanced along the guidewire and is accommodated by the first tubular means. Then the proximal end of the second tubular means is connected to the pressurized fluid source means which provides pressurized saline (or other biologically compatible fluid) to the proximal end of the high pressure tubular means via the pressurized fluid connection means. At the distal end of the high pressure tubular means, pressurized saline (or other fluid) passes into the jet emanator means which produces high velocity saline (or other fluid) jet(s). The high velocity saline (or other fluid) jet(s) entrain blood or other fluid from the body vessel or cavity and draw it into the distal portion of the elongated device through the inflow means, carrying thrombus or other unwanted material from the body vessel or cavity along with the blood or other fluid. The high velocity saline (or other fluid) jet(s) together with the entrained blood or other fluid create a region of elevated pressure in the elongated device; this region of elevated pressure communicates with or is a part of the distal portion of the exhaust tubular means. Optionally, the elevated pressure in the elevated pressure region drives fluid flow through the outflow means, creating crossflow jet(s) which have a radial component and may have circumferential and/or axial component(s) as well. The fluid in the elevated pressure region includes saline (or other fluid) from the high velocity jet(s) as well as the entrained blood or other fluid from the body vessel or cavity. The crossflow jet(s) impart normal and drag forces on thrombus or other unwanted material in the body vessel or cavity and greatly improve the effectiveness of the device in removing and breaking apart thrombus or other unwanted material which may be adhered to the body vessel or cavity, and form a recirculation pattern which further aids in drawing thrombus or other unwanted material towards the inflow means. The combination of outflow means, crossflow jet(s), recirculation pattern, inflow means, and high velocity jet(s) synergistically acts to provide for enhanced breakup and removal of thrombus or other unwanted material. The elevated pressure in the elevated pressure region can also aid in the transport of fluid and thrombus or other unwanted material debris through the exhaust tubular means. If desired, the rate of flow of fluid and thrombus or other unwanted material can be regulated by providing exhaust regulation means, although this is not always required.

Figure 2:
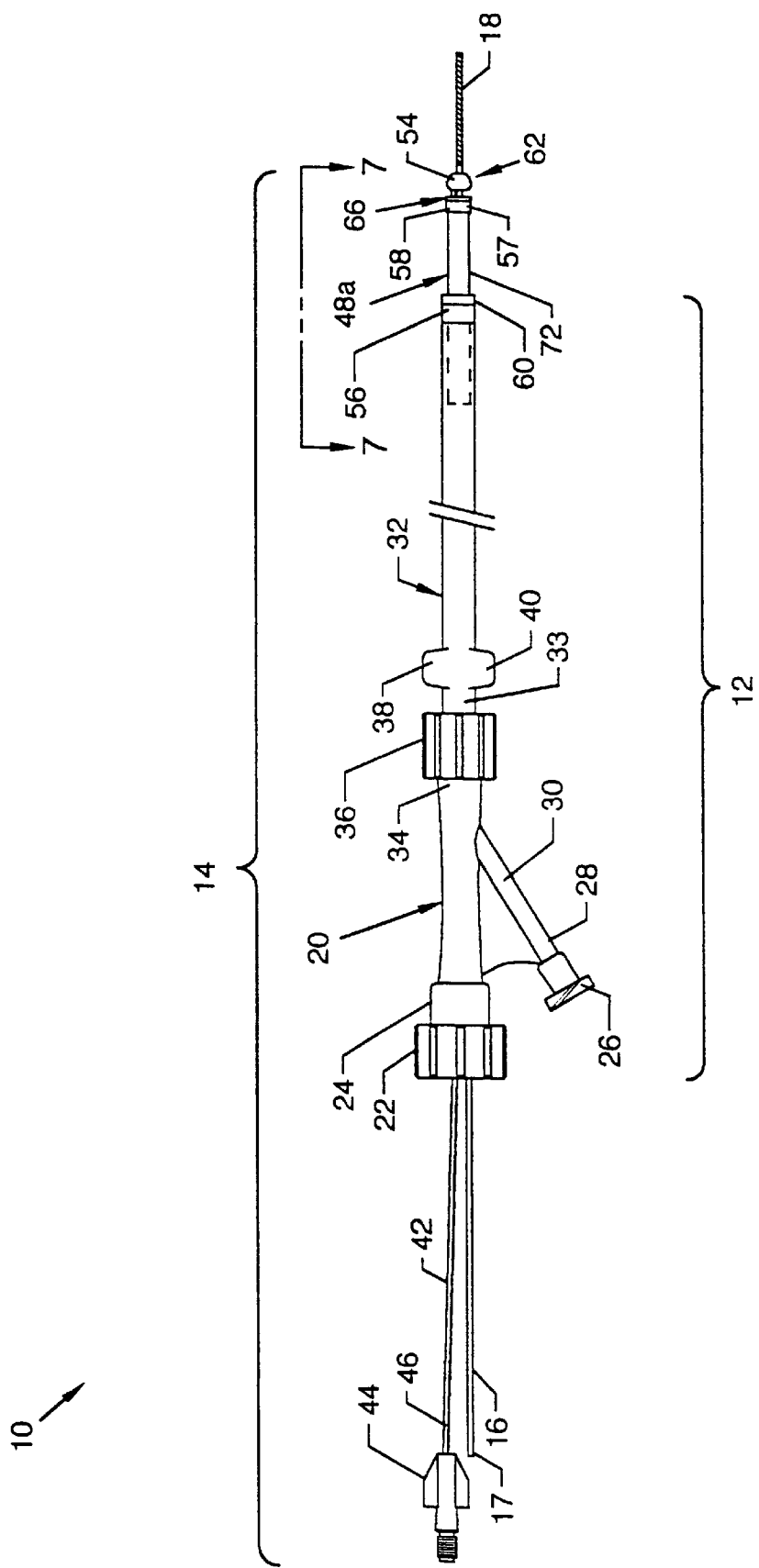
FIG. 2 illustrates a side view of a single operator exchange fluid jet thrombectomy device.
Figure 3:
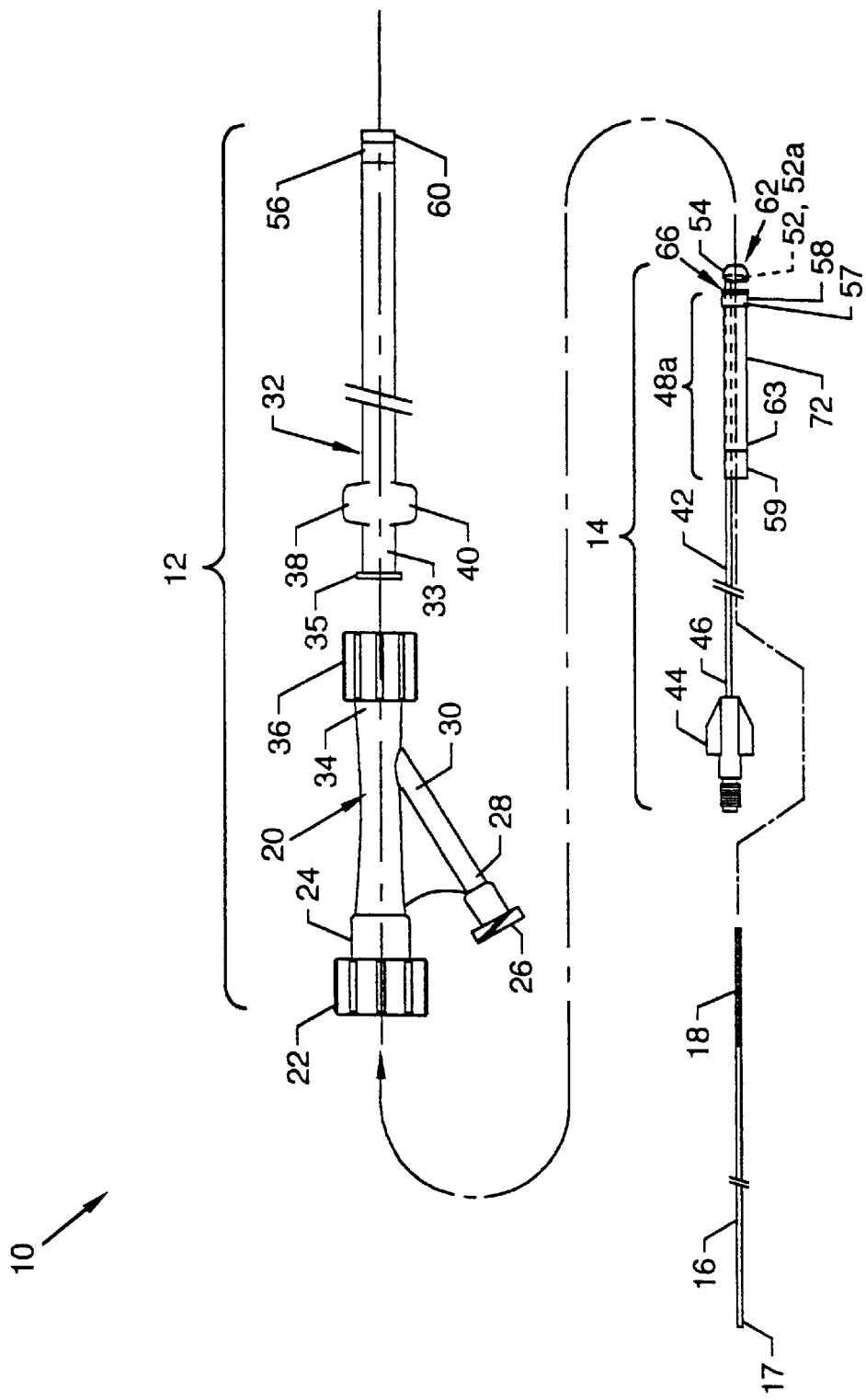
FIG. 3 illustrates a semi-exploded side view of the single operator exchange fluid jet thrombectomy device.
Figure 4:
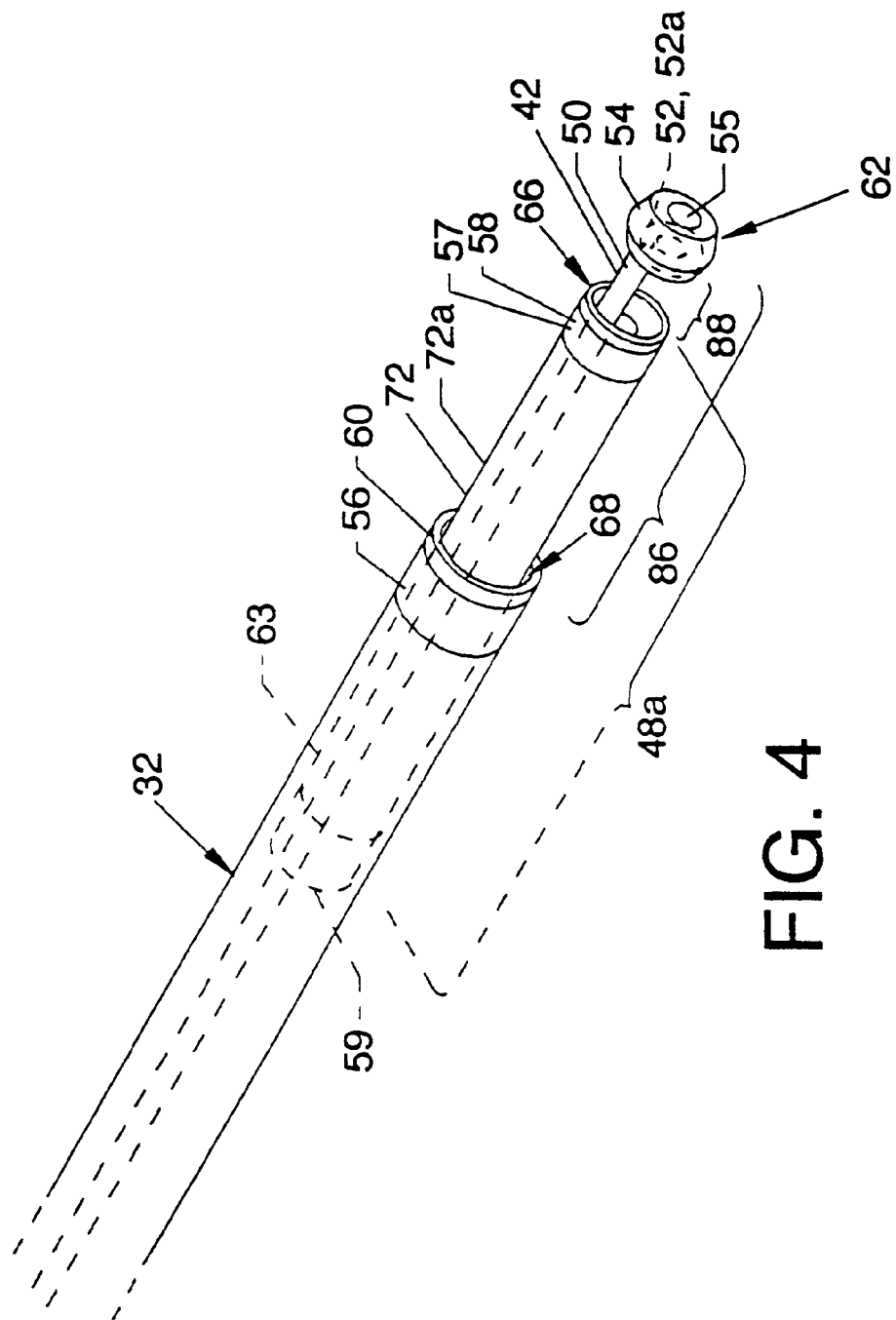
FIG. 4 illustrates an isometric view of the distal end of the first tube or guide catheter with a portion of the inner catheter assembly protruding therefrom.
Figure 19:
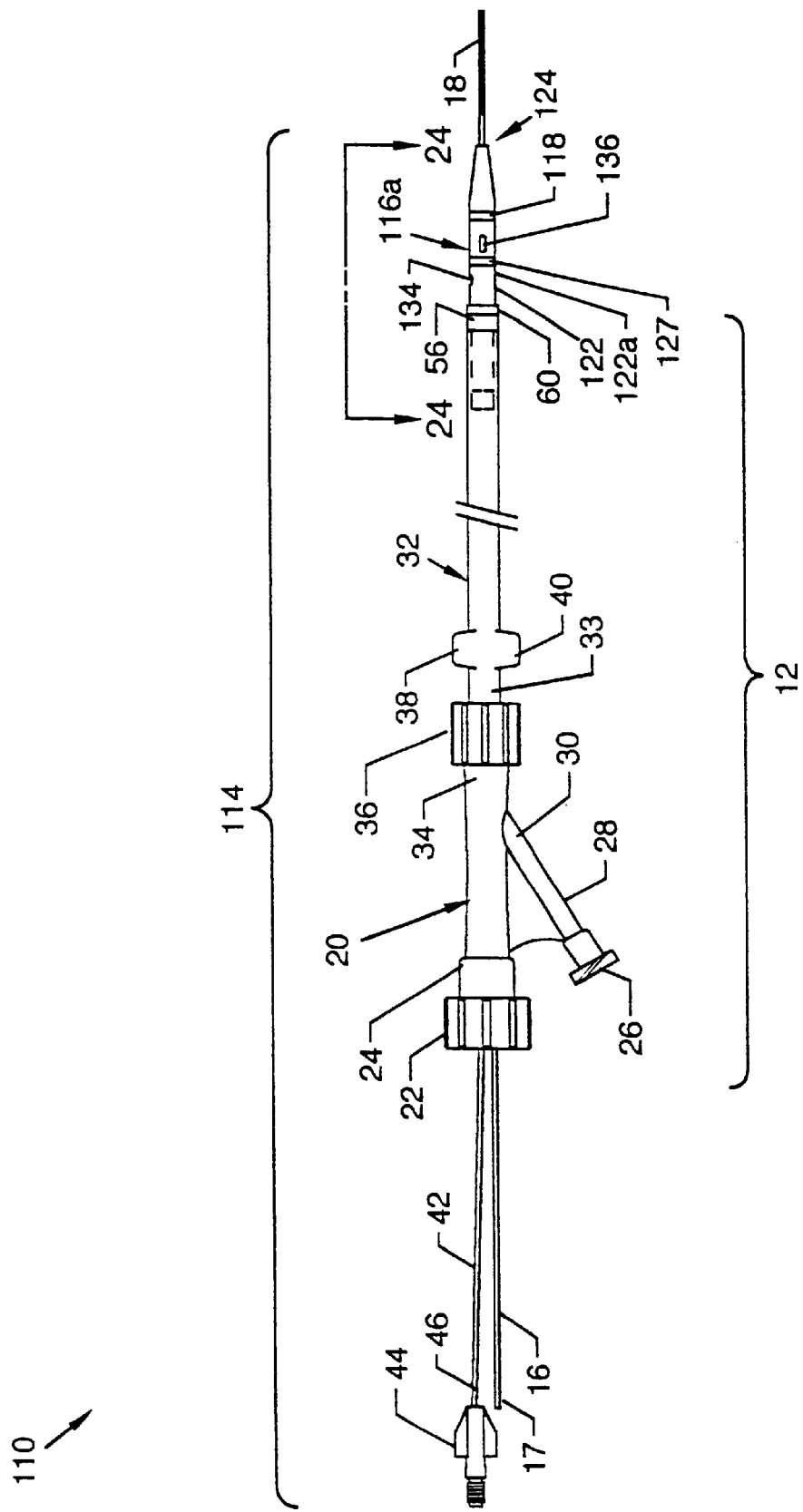
FIG. 19, a fourth alternative embodiment, illustrates a side view of a single operator exchange fluid jet thrombectomy device incorporating an inner catheter assembly having a crossflow capability.
Figure 20:
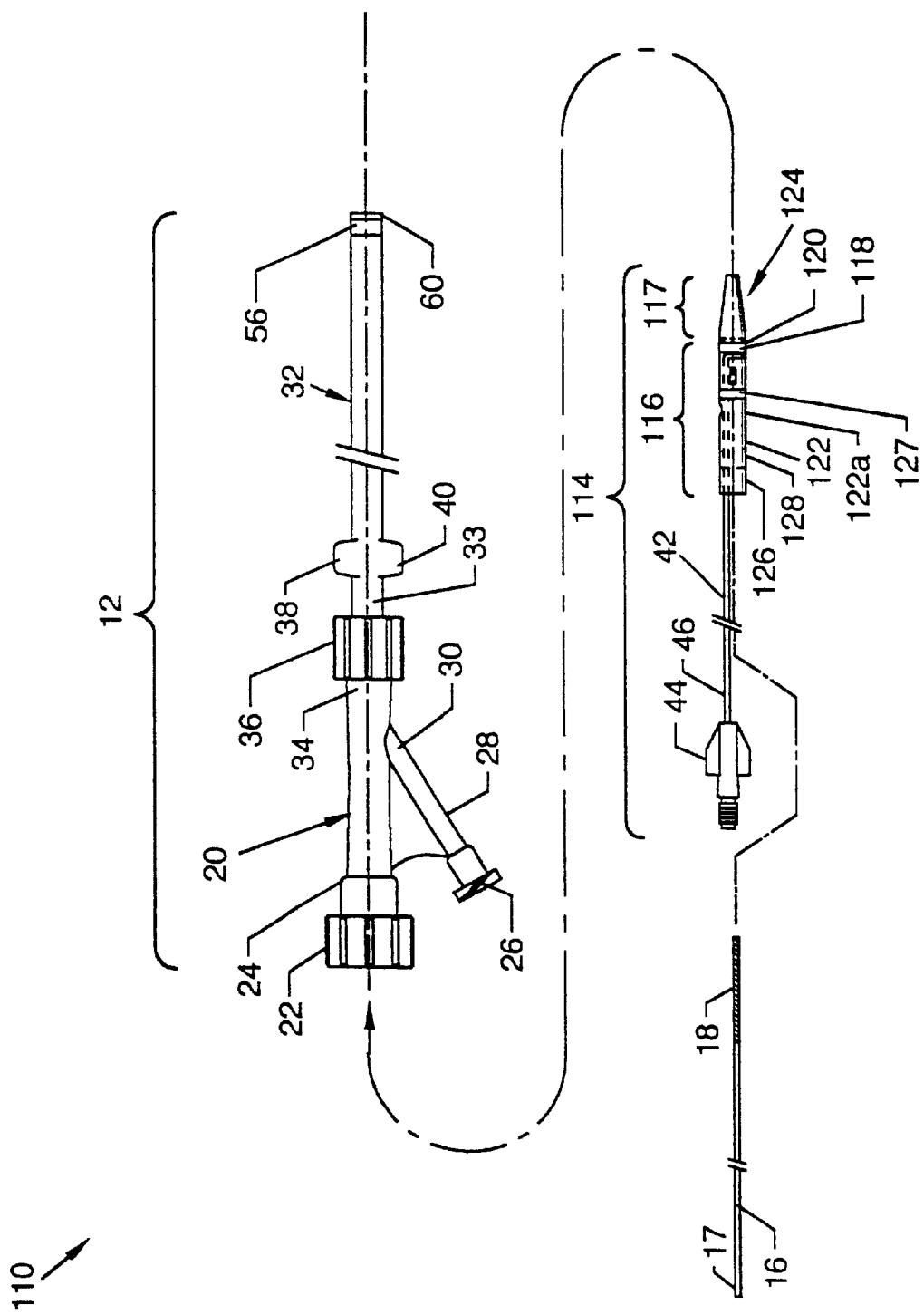
FIG. 20 illustrates a semi-exploded side view of the single operator exchange fluid jet thrombectomy device of FIG. 19.

FIG. 2 illustrates a side view of a single operator exchange fluid jet thrombectomy device 10 useful for the removal of thrombus, and FIG. 3 illustrates a semi-exploded side view of the single operator exchange fluid jet thrombectomy device 10. The single operator exchange fluid jet thrombectomy device 10 includes two major assemblies: namely, an outer catheter assembly 12, which is a core assembly, and an inner catheter assembly 14 configured to function as a rheolytic thrombectomy catheter, which can be exchanged with other styles or designs of inner catheter assemblies, as desired, such as shown in FIGS. 19 and 20, to fit substantially within the outer catheter assembly 12. The outer catheter assembly 12 is preferably a standard guide catheter, but may also be a catheter specifically designed for this application. The outer catheter assembly 12 design should have proper torque, stiffness, and shape to place the device in the thrombus containing blood vessel. The inner catheter assembly 14, when in use, aligns substantially concentrically to and mostly within the outer catheter assembly 12 and extends beyond both ends of the outer catheter assembly 12. A guidewire 16 including a flexible tip 18 at one end and a proximal end 17 opposing the flexible tip 18 is shown in substantially concentric alignment to both the outer catheter assembly 12 and the inner catheter assembly 14. Externally visible components, or portions of components, of the outer catheter assembly 12 and of the inner catheter assembly 14 of the single operator exchange fluid jet thrombectomy device 10, as illustrated in FIGS. 2 and 3, also include a manifold 20, also known as a Y-adapter, a hemostasis nut/stop 22 secured in the proximal end 24 of the manifold 20, a Luer connection 26 located at the proximal end 28 of an angled manifold branch 30 extending from the manifold 20, and a first tube or guide catheter 32, having a Luer connection 35 at a proximal end 33, secured to distal end 34 of the manifold 20 by Luer fitting 36. Opposing manipulating tabs 38 and 40 are also provided near the proximal end 33 of the first tube or guide catheter 32. The externally visible components of the inner assembly 14, illustrated in FIG. 2, also include a high pressure second tube 42, a transitional filter housing/high pressure connection/stop assembly 44 concentrically aligned to and secured over and about the proximal end 46 of the second tube 42, a flow director 48a comprised substantially of an exhaust tube in general and generally referred to as exhaust tube 72, which is further and specifically referred to and specified as either a compliant expandable exhaust tube 72a, a non-compliant expandable exhaust tube 72b, or a non-expandable, non-compliant close fit exhaust tube 72c aligned over and about the distal end 50 (FIG. 4) of the second tube 42, an optional jet cap 54 having a central passage 55 (FIG. 4) aligned to and secured over and about a jet emanator 52 which could be and which is shown as a toroidal loop 52a having a passage 53 (FIG. 5) at the distal end 50 of the second tube 42, a radio-opaque marker 56 aligned over and about a distal end 60 of the first tube or guide catheter 32 and a radio-opaque marker 58 located at the distal end 57 of the exhaust tube 72, which could be and which is shown as a compliant expandable exhaust tube 72a, to mark the substantially co-located distal end 50 of the second tube 42 and distal end 62 of the inner catheter assembly 14 including the jet emanator 52 and optional jet cap 54. An optional radio-opaque marker 59 can also be located and attached to or be integral to the proximal end 63 of the exhaust tube 72 and included, along with radio-opaque marker 58, as an optional integral part of the flow director 48a. An inner body 66, part of the flow director 48a, frictionally engages the distal end 57 of the exhaust tube 72 of the flow director 48a, as later described in detail. The high pressure second tube 42 can be drawn and tapered in incremental steps to provide degrees of flexibility along its length. For purposes of example and illustration, the second tube 42 can include an initial and proximal outer diameter of 0.018 inch or smaller, and can include a plurality of incrementally stepped down portions each of lesser outer diameter, where the last portion is stepped down to an outer diameter of 0.008 inch at the distal end 50 (FIG. 4). The second tube 42 becomes increasingly more flexible from the proximal end 46 towards the distal end 50 due to the incremental diameter decrease along its length. Increasing flexibility along the length of the second tube 42 allows for easier flexed penetration into tortuous vascular paths. Although the second tube 42 is stepped down in increments, the second tube 42 can also be fashioned of a constantly decreasing outer diameter to provide increasing flexibility along its length and shall not be construed to be limiting to the scope of the invention.

Figure 5:
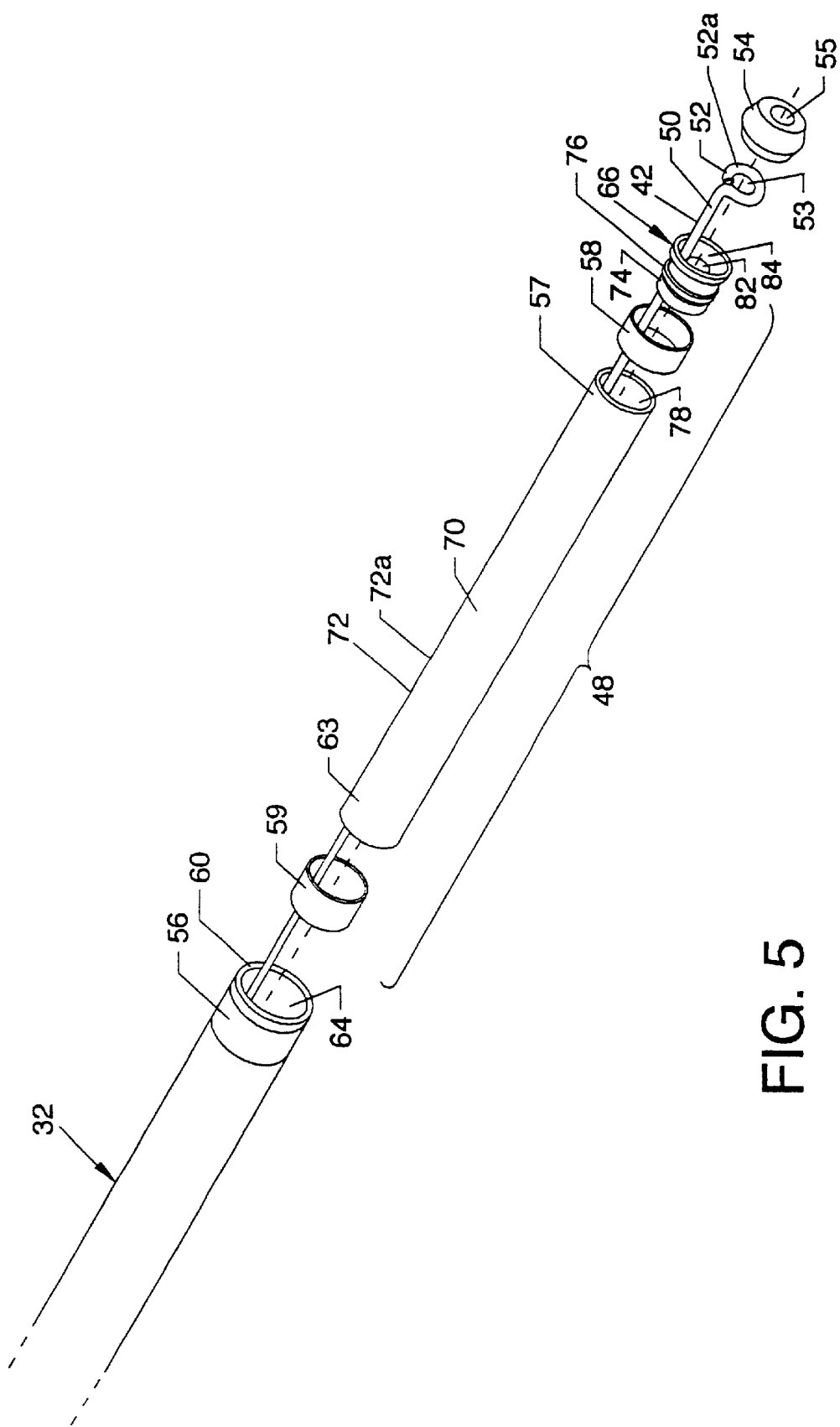
FIG. 5 illustrates an exploded view of the components of FIG. 4.
Figure 7:
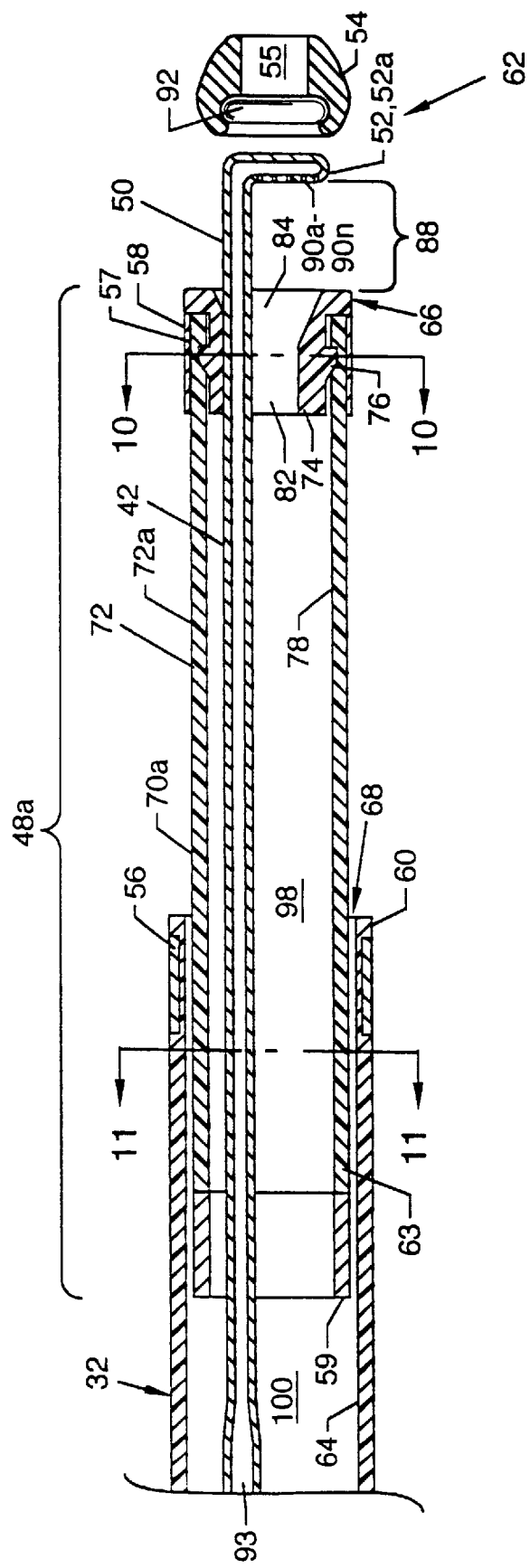
FIG. 7 illustrates a cross section view of the distal end of the first tube or guide catheter and the flow director in the unpressurized mode, along the line 7—7 of FIG. 2.

FIG. 4 illustrates an isometric view of the distal end 60 of the first tube or guide catheter 32 with a portion of the inner catheter assembly 14 protruding therefrom, and FIG. 5 illustrates an exploded view of the components of FIG. 4. Illustrated in particular is the relationship of the components aligned in the distal end 60 of the first tube or guide catheter 32 during use of the invention, where an exhaust tube 72 in the form of a compliant expandable exhaust tube 72a is utilized. Guidewire 16 is not shown for purposes of brevity and clarity. The second tube 42 extends proximally through the flow director 48a, and collectively the second tube 42 and the flow director 48a extend proximally through the first tube or guide catheter 32. As illustrated in the unpressurized mode in FIG. 4 and as also illustrated in the unpressurized mode in FIG. 7, it is noted that an annulus 68 is formed between the interior annular surface 64 of the first tube or guide catheter 32 and an outer annular surface 70a of an exhaust tube 72. During normal pressurized operation, an exhaust tube 72, in this case a compliant expandable exhaust tube 72a, expands to cause the outer annular surface 70a of an exhaust tube 72 to expand and impinge the interior annular surface 64 of the first tube or guide catheter 32, thereby closing the annulus 68, as later described in detail. The inner body 66 includes a reduced radius neck 74 interrupted by an annular barb 76 both of which are accommodated by the interior annular surface 78 at the distal end 57 of exhaust tube 72. The reduced radius neck 74 also includes a slotted cutout 80 (FIG. 10) for mounting, such as by welds 81 and 83 or other suitable means, of the distal end 50 of the second tube 42. Also included, and as shown in FIGS. 5 and 7, in the interior of the inner body 66 is a passage 82 having a ramped annular surface 84. A space 88 is located between the inner body 66 and the jet emanator 52 where the thrombus is macerated and then pushed through the flow director 48a and into the first tube or guide catheter 32 for removal from the body.

During performance of the method of the invention the outer catheter assembly 12 is advanced along a vein or other blood vessel or passage to a vascular site containing thrombus followed by the passage of the guidewire 16 through and beyond the distal end 60 of the first tube or guide catheter 32 and thence followed by advancement of the inner catheter assembly 14 along the guidewire 16 and along the interior of the outer catheter assembly 12. As the second tube 42 is positioned, during pressurized or unpressurized operation, the flow director 48a, the jet emanator 52, the optional jet cap 54, along with the second tube 42, move and position as a unit to a desired position along a variable displacement distance 86 which is the distance from the distal end 60 of the first tube or guide catheter 32 to and including the optional jet cap 54. The variable displacement distance 86 can range from a minimum distance where the jet emanator 52, or the optional jet cap 54, at the distal end 50 of the second tube 42 is positioned just inside the distal end 60 of the first tube or guide catheter 32, where no thrombus ablation occurs, to a maximum distance where the jet emanator 52, or the optional jet cap 54, has advanced to a position well beyond the distal end 60 of the first tube or guide catheter 32, thus positioning the proximal end 63 of an exhaust tube 72 along a region proximal to the distal end 60 of the first tube or guide catheter 32, whereby a major portion of the exhaust tube 72, the entire inner body 66, the jet emanator 52, and the optional jet cap 54 are distally located with reference to the distal end 60 of the first tube or guide catheter 32. At or near this extended position, further distal movement is prevented by impingement of the transitional filter housing/high pressure connection/stop assembly 44 with the hemostasis nut/stop 22, which are shown in FIG. 2.

Figure 6:
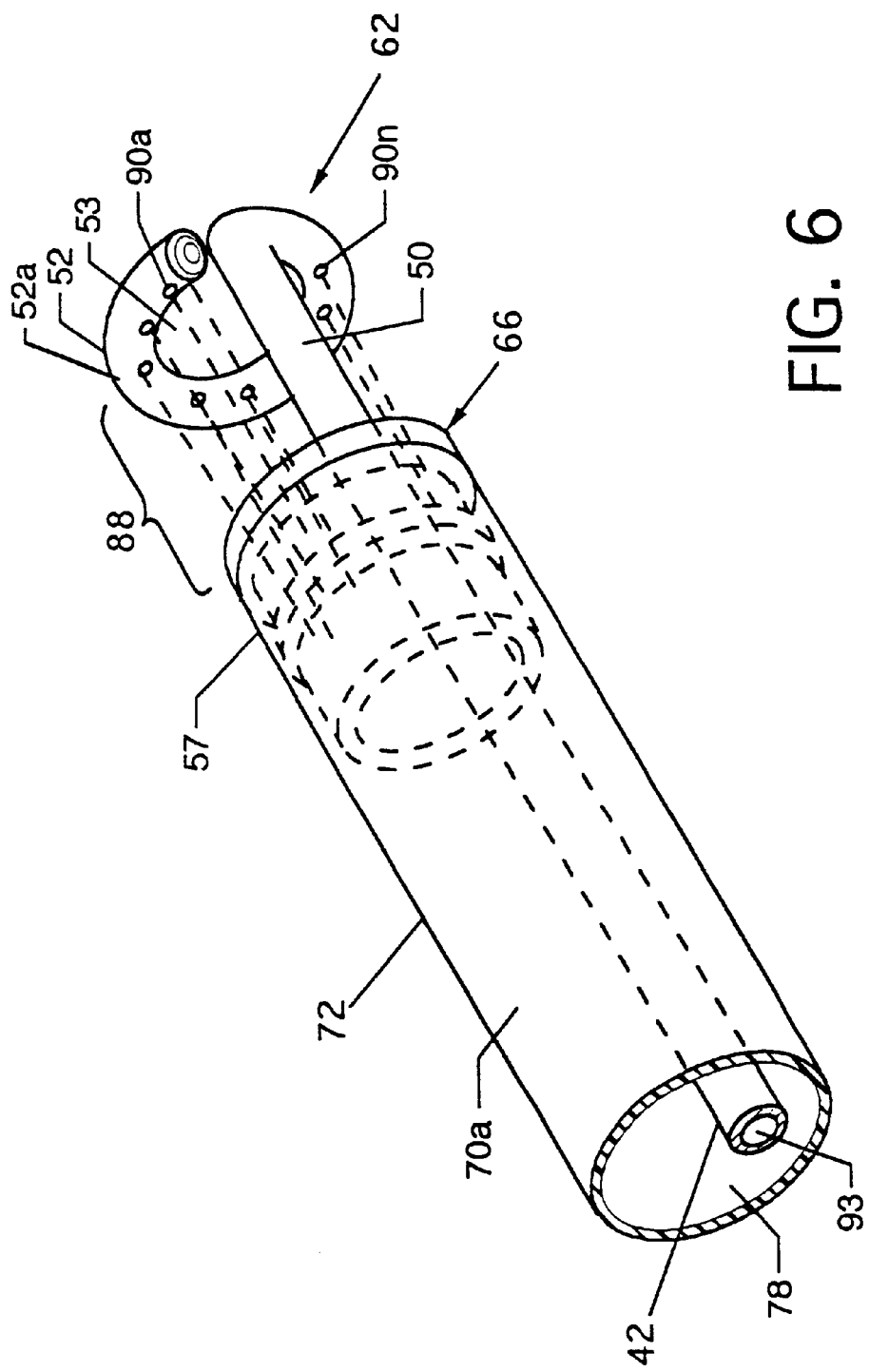
FIG. 6 illustrates an isometric view of one jet emanator means, a toroidal loop.

FIG. 6 illustrates an isometric view of one jet emanator 52 means, being a toroidal loop 52a, which may be utilized at the distal end 50 of the second tube 42 to direct high velocity jet streams proximally along or near the longitudinal axis of the second tube 42 and an exhaust tube 72. Any jet emanator means such as the ones shown herein or the ones shown in related patent application Ser. No. 09/417,395 by the inventors which comprise a distal tubular structure of a high pressure tubular means, such as the second tube 42, through which pressurized fluid flows creating high velocity fluid jets which emanate from one or more orifices in the distal tubular structure, can be used. The distal tubular structure can be of straight, curved, L-shaped, J-shaped, U-shaped, helical, toroidal or semi-toroidal shape, or can be a chamber such as a manifold, and may be formed of a single component, such as a metal hypo-tube, or of multiple components, such as multiple hypo-tubes, welded manifold components, or molded manifold components. The distal tubular structure forming the jet emanator means may be formed as a unitary part of the high pressure tubular means such as by forming a metal hypo-tube into a toroidal shape, or one of the other shapes mentioned above, with a single orifice or multiple orifices produced by drilling or cutting. The orifices can be round, slits, or other shapes so that fluid flowing therethrough forms one or more discrete high velocity fluid jets or merges into combination jets. Alternatively, the distal tubular structure forming the jet emanator means may be a separate structure having any one of the aforementioned shapes and orifice constructions which is attached to the distal end of the high pressure tubular means. In either event, the distal tubular structure forming the jet emanator means is in fluid communication with the high pressure tubular means. In any circumstance, highly pressurized fluid(s) first passes through a lumen of the high pressure tubular means enroute to the variously shaped and configured distally located jet emanator means.

As previously mentioned, FIG. 6 illustrates an isometric view of the jet emanator 52 in the form of a toroidal loop 52a which is located at the distal end 50 of the second tube 42, the jet emanator 52 being sometimes referred to as a jet body. Illustrated in particular are a plurality of proximally directed jet orifices 90a–90n located on the proximal surface of the toroidal loop 52a which direct high velocity jet streams proximally, as shown by dashed lines, along or near the longitudinal axis of the second tube 42 and the exhaust tube 72 which, of course, can be one of several styles described. The toroidal loop 52a includes a circular passage 53 along the inner circumference to provide for, to accommodate alignment of, and to permit passage along a guidewire, such as the guidewire 16 shown partially in FIG. 18. Multiple jet orifices 90a–90n located at points along the toroidal loop 52a can advantageously direct high velocity jet streams on multiple sides of the guidewire 16 when it is positioned in the passage 53 to avoid having guidewire 16 block or hamper the macerating effect of the jet streams on thrombotic matter.

Figure 8:
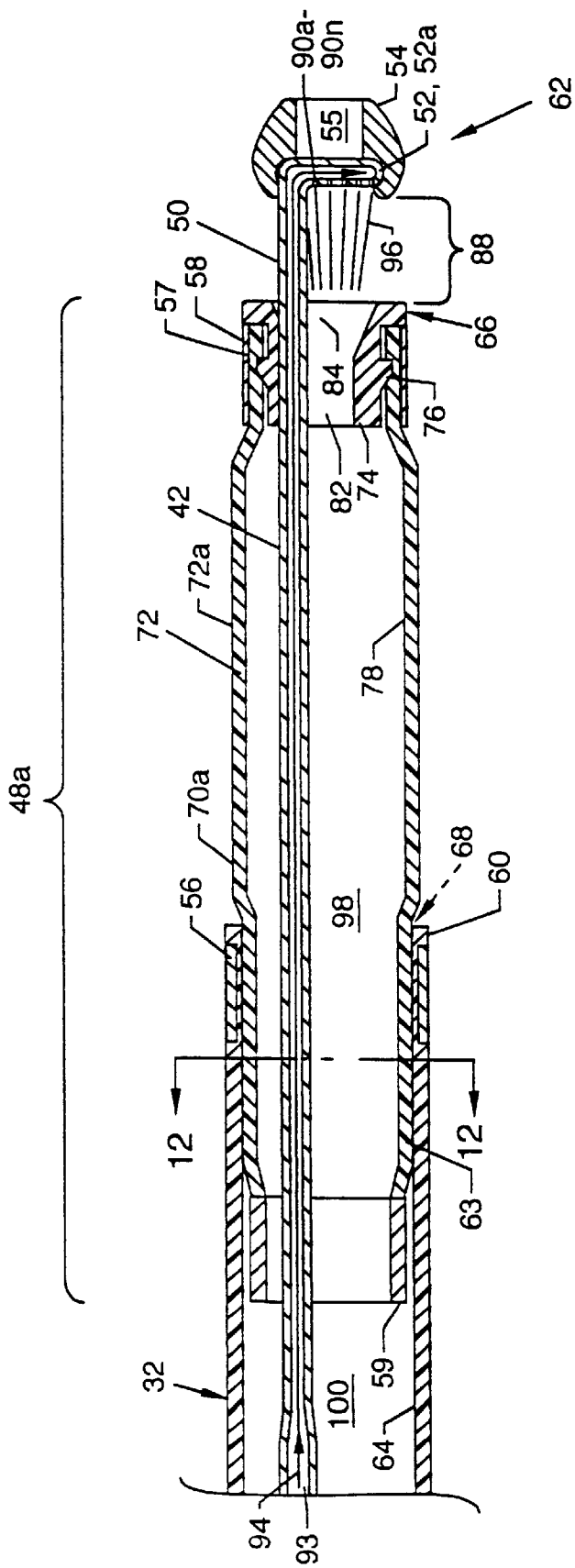
FIG. 8 illustrates a cross section view of the elements of FIG. 7 in the pressurized mode.
Figure 9:
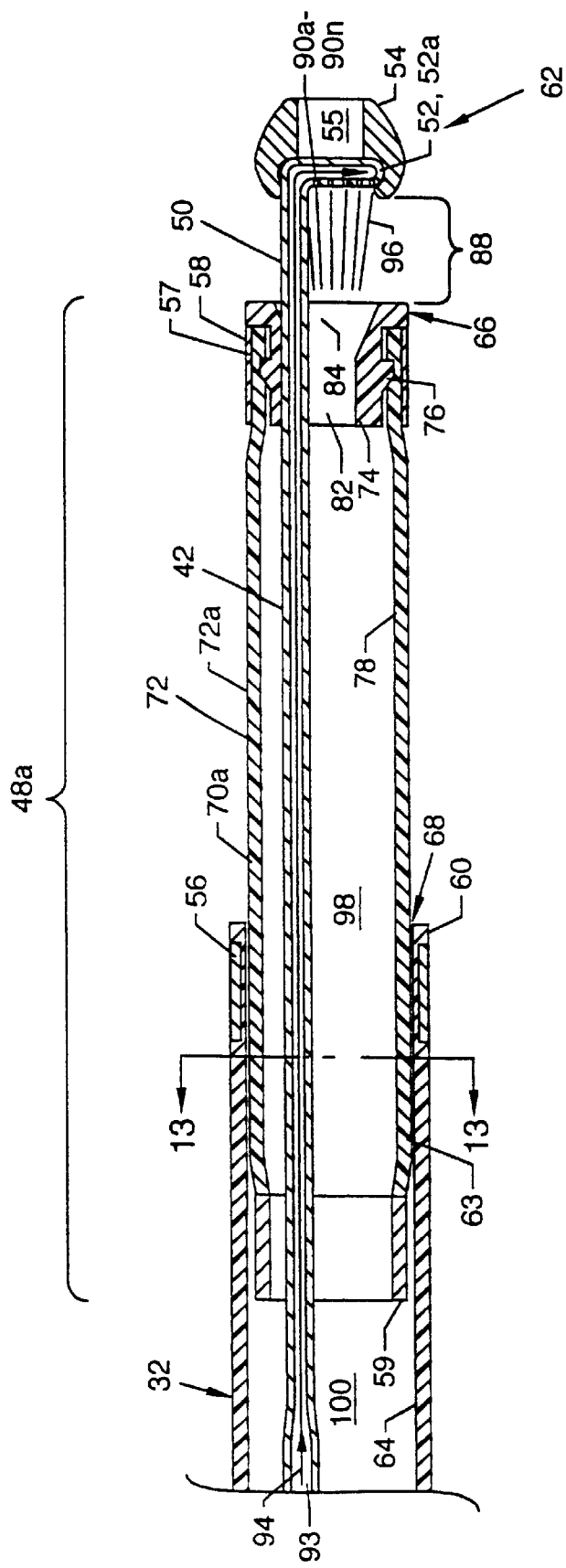
FIG. 9 illustrates a cross section view of the elements of FIG. 7 in the partially pressurized mode.

FIGS. 7, 8 and 9 substantially illustrate the mutual accommodation and the alignment of the distal portions of the outer catheter assembly 12 and inner catheter assembly 14, where exhaust tube 72 is in the form of a compliant expandable exhaust tube 72a.

FIG. 7 illustrates a cross section view of the distal end 60 of the first tube or guide catheter 32 and the flow director 48a in the unpressurized mode, including the second tube 42 and the flow director 48a in extended concentric alignment with the first tube or guide catheter 32 and associated components, along line 7—7 of FIG. 2. Illustrated in particular is the relationship of the interior annular surface 64 of the first tube or guide catheter 32 and the outer annular surface 70a of an exhaust tube 72, in the form of a compliant expandable exhaust tube 72a, which form the annulus 68 which is elongated. Typically, the compliant expandable exhaust tube 72a can be fashioned of, but not limited to, materials such as urethane or silicone, for example. A horizontally aligned slotted cutout 80 (FIG. 10) in the upper region of the inner body 66 accommodates the distal end 50 of the second tube 42 which suitably secures and seals therein. Also illustrated is the optional jet cap 54 which secures at the distal end 50 of the second tube 42 over and about the jet emanator 52. The optional jet cap 54 includes passage 55 which intersects a proximally facing annular capturing cavity 92 which accommodatingly accepts and fits and secures to the toroidal loop 52a, a jet emanator 52. Jet orifices 90a–90n located on toroidal loop 52a at the distal end 50 of the second tube 42 are directed rearwardly and slightly towards the longitudinal axis of the exhaust tube 72 and of the inner body 66. The predetermined and suitable space 88 is located between the proximal region of a jet emanator 52, and, in general, the distal end 57 of the exhaust tube 72, and, more specifically, the distal end of the ramped annular surface 84 of the inner body 66. The maximum distal position of the space 88 with relation to the distal end 50 of the second tube 42 can be determined, if so constructed using a suitable length second tube 42, by the relationship of the distal end of the transitional filter housing/high pressure connection/stop assembly 44 (FIG. 2) and the hemostasis nut/stop 22 which contact each other to limit the distal movement of the second tube 42. The location of space 88 can also be determined by observation of the relationship of one or more of the following components, including the radio-opaque marker 56 at the distal end 60 of the first tube or guide catheter 32, the radio-opaque marker 59, the radio-opaque marker 58, the inner body 66, the jet cap 54, or of other components by known observation methods. The second tube 42 can be fashioned of material such as, but not limited to, stainless steel or nickel titanium alloys.

FIG. 8 illustrates a cross section view of the elements of FIG. 7, including the second tube 42 and the flow director 48a in extended concentric alignment with the first tube or guide catheter 32 and associated components in the pressurized mode. Subsequent to proper positioning of the appropriate component of the invention in a vessel or other body member in the unpressurized mode, saline 94, under high pressure, is injected through the inner catheter assembly 14 through a high pressure lumen 93 of the second tube 42 and delivered to the distal end 50 to emanate as saline jet flow 96 from the jet orifices 90a–90n of the toroidal loop 52a. The pressurized saline jet flow 96 is directed partially into the ramped annular surface 84 and the passage 82 of the inner body 66 and partially into the lumen 98 of the exhaust tube 72 to pressurize the exhaust tube 72 causing the exhaust tube 72 in the form of a compliant expandable exhaust tube 72a to expand and force the outer annular surface 70 of the exhaust tube 72 to seal against the interior annular surface 64 of the first tube or guide catheter 32. The saline jet flow 96 also flows to entrain thrombotic tissue adjacent to or lying within the space 88 to break up and erode the thrombotic tissue. Positive pressurized flow of the pressurized saline and the entrained particles of thrombotic tissue is prevented from back flowing out of the previously open annulus 68 which has been subsequently closed by the seal between the inner catheter assembly 14 within the outer catheter assembly 12 and is allowed to travel under full pressurized force along the lumen 98 of the exhaust tube 72 and along a lumen 100 central to the first tube or guide catheter 32 and thence through a catheter lumen interior to the manifold 20 and outwardly through the angled manifold branch 30. The ability to insert and maneuver the inner catheter assembly 14 within the outer catheter assembly 12 freely and unhampered and then to subsequently effect a seal between the inner catheter assembly 14 and the outer catheter assembly 12 while maintaining maneuverability contributes to the novelty, efficiency, and usefulness of the method of the invention.

FIG. 9 illustrates a cross section view of the elements of FIG. 7, including the second tube 42 and the flow director 48a in extended concentric alignment with the first tube or guide catheter 32 and associated components in a partially pressurized mode or when the expandable exhaust tube is deliberately undersized to prevent a complete seal from being made. This figure illustrates the partially pressurized mode where it is desirable to have the annulus 68 reduced in size from that shown in FIG. 7. Such reduction allows more freedom of longitudinal and rotational movement and maneuverability between the inner catheter assembly 14 and the outer catheter assembly 12 while still maintaining a suitable seal. Freedom of rotational movement is desirable to permit greater flexibility with respect to full and effective radial positioning of the space 88. Sufficient saline pressure may still be maintained and any pressure loss through the reduced size annulus 68 is negligible.

Figure 10:
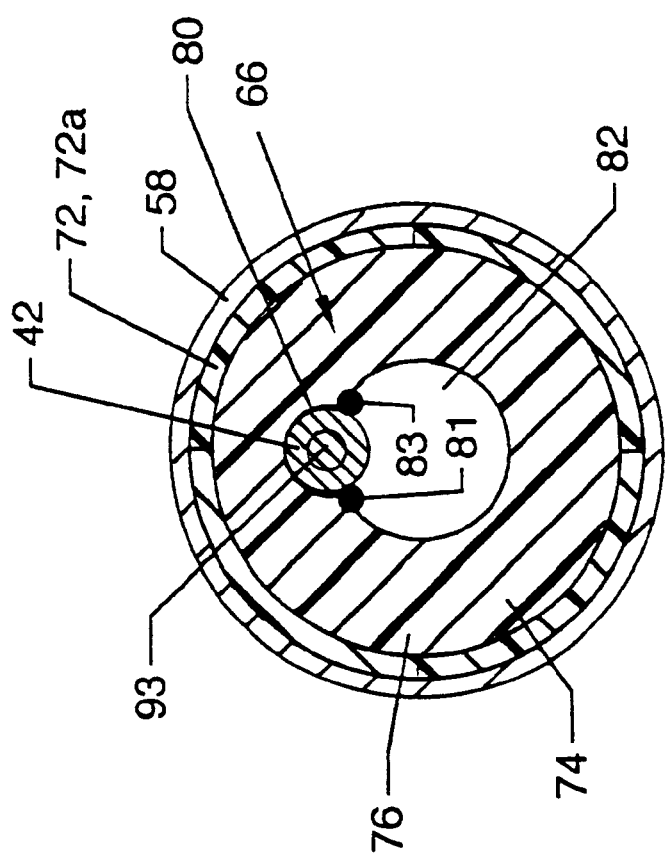
FIG. 10 illustrates a cross section view of the junction of the inner body and the expandable exhaust tube along line 10—10 of FIG. 7.

FIG. 10 illustrates a cross section view of the junction of the inner body 66 and the exhaust tube 72 along line 10—10 of FIG. 7. Illustrated in particular is the mounting and the securing of the second tube 42 to opposing sides of the slotted cutout 80 in the reduced radius neck 74 and/or ramped annular surface 84 of the inner body 66 by welds 81 and 83. Positioning and securing of the second tube 42 in the upper region of the inner body 66 ensures alignment of the optional jet cap 54 and a jet emanator 52 with the inner body 66.

Figure 11:
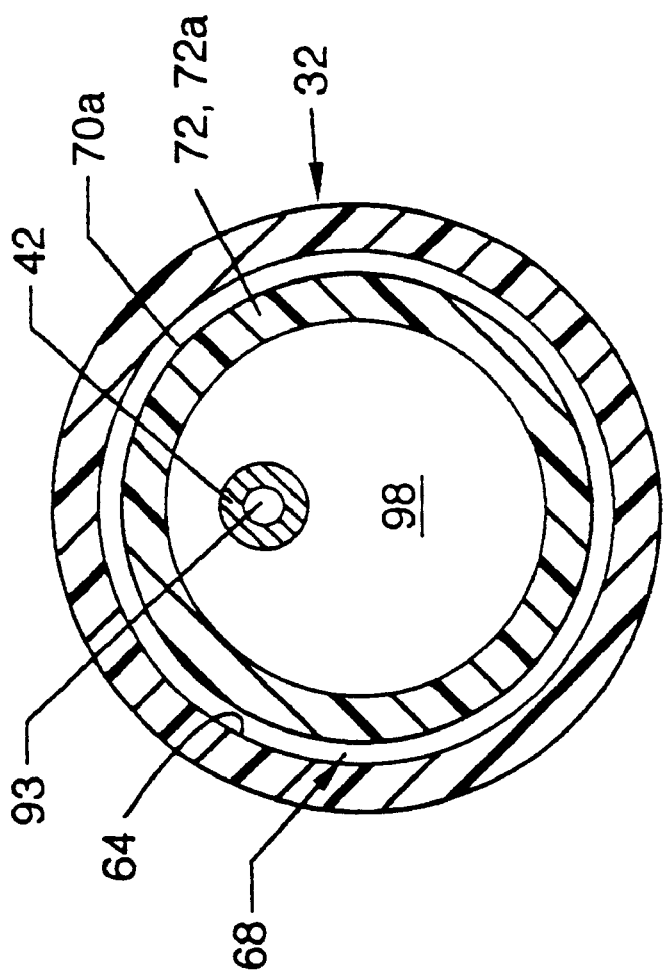
FIG. 11 illustrates a cross section view at the distal end of the first tube or guide catheter along line 11—11 of FIG. 7 in the unpressurized mode.

FIG. 11 illustrates a cross section view at the distal end 60 of the first tube or guide catheter 32 along line 11—11 of FIG. 7 in the unpressurized mode. Illustrated in particular is the annulus 68 between the interior annular surface 64 and the outer annular surface 70. Annulus 68 allows for ready and adequate passage of the flow director 48a through the first tube or guide catheter 32 subsequent to positioning of the outer catheter assembly 12 (FIG. 3).

Figure 12:
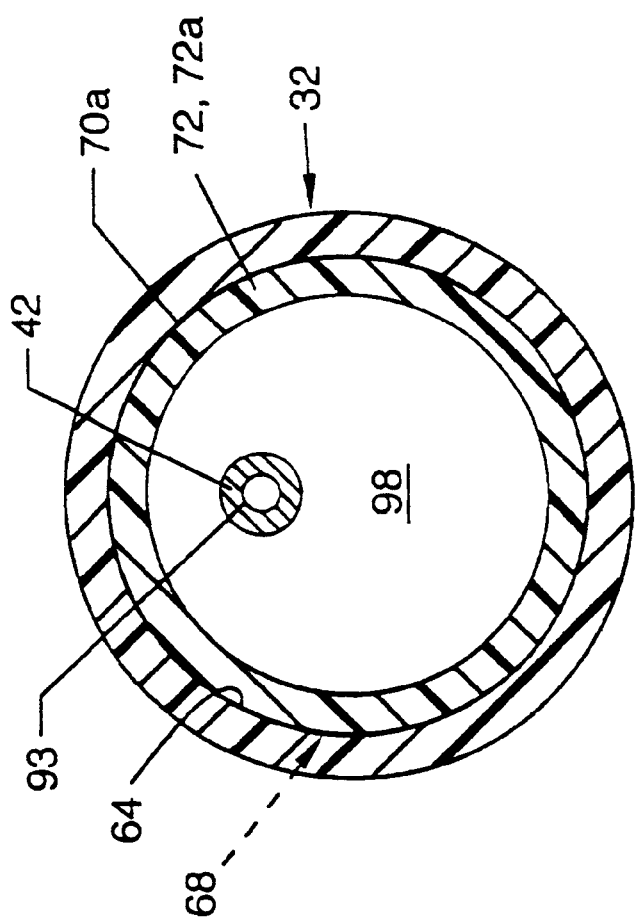
FIG. 12 illustrates a cross section view at the distal end of the first tube or guide catheter along line 12—12 of FIG. 8 in the pressurized mode.

FIG. 12 illustrates a cross section view at the distal end 60 of the first tube or guide catheter 32 along line 12—12 of FIG. 8 in the pressurized mode. Illustrated in particular is the closing or elimination of the annulus 68 (FIG. 7) between the interior annular surface 64 and the outer annular surface 70a. Closing of the annulus 68 allows for sealing of the flow director 48a against the interior annular surface 64 to maintain full pressurization.

Figure 13:
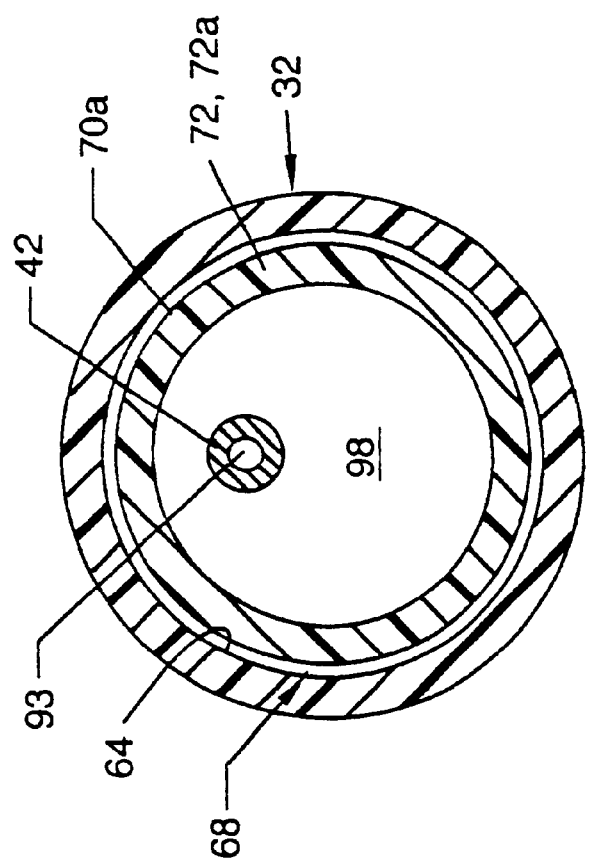
FIG. 13 illustrates a cross section view at the distal end of the first tube or guide catheter along line 13—13 of FIG. 9 in the partially pressurized mode.

FIG. 13 illustrates a cross section view at the distal end 60 of the first tube or guide catheter 32 along line 13—13 of FIG. 9 in the partially pressurized mode or non-sealing design. Illustrated in particular is the reduction in size of the annulus 68 (FIG. 7) between the interior annular surface 64 and the outer annular surface 70a.

Figure 14:
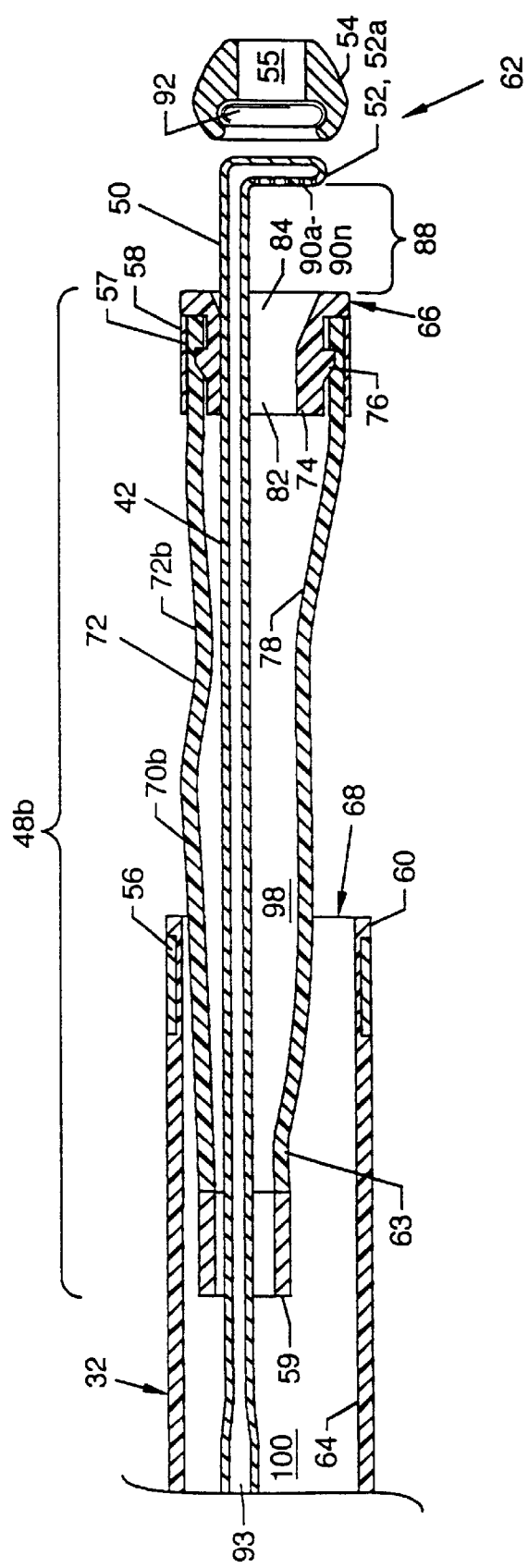
FIG. 14, a first alternative embodiment, illustrates a cross section view of the elements of FIG. 7 featuring an optional non-compliant expandable exhaust tube.

FIG. 14, a first alternative embodiment, illustrates a cross section view of the elements such as described in FIG. 7, including the second tube 42 and an optional flow director 48b in loose and non-regular alignment with the first tube or guide catheter 32 and associated components. This embodiment operates much the same as previous embodiments, but differs from the previous embodiments in that an optional flow director 48b is provided which includes the components of the flow director 48a with the exception of an exhaust tube 72 in the form of an optional non-compliant expandable exhaust tube 72b. The non-compliant expandable exhaust tube 72b can be fashioned of material, such as, but not limited to, flexible polyethylene or polyethylene terephthalate, for example, and can be expanded from an irregular or baggy appearing tubular structure to a regular appearing shaped structure, such as shown in FIG. 15.

Figure 15:
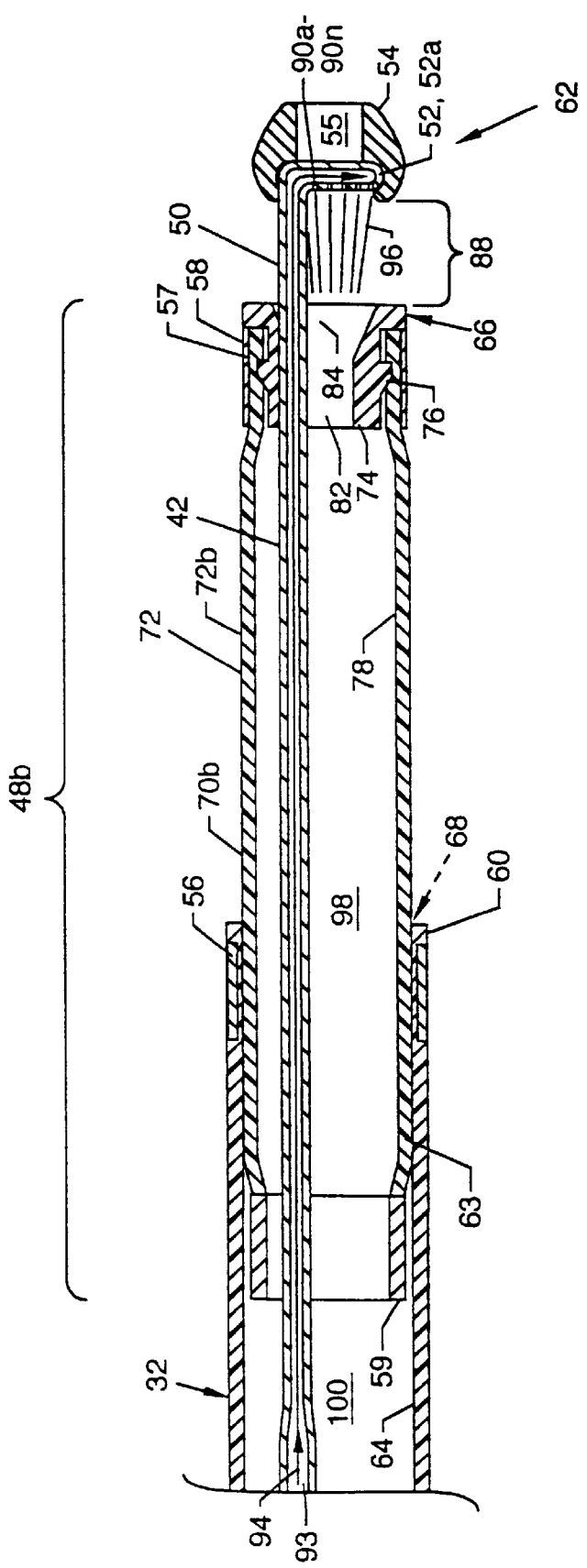
FIG. 15 illustrates the non-compliant expandable exhaust tube of FIG. 14 in the inflated mode to close a previously open annulus.

FIG. 15 illustrates a cross section view of the elements of FIG. 14 in the pressurized mode where the exhaust tube 72 in the form of a non-compliant expandable exhaust tube 72b is pressurized by high pressure saline 94 emanating as saline jet flow 96 from a jet emanator 52, depicted more specifically as a toroidal loop 52a, thereby causing the non-compliant expandable exhaust tube 72b to expandingly assume a regular shape and structure which forces the outer surface 70b (now annular) to closingly seal against the interior annular surface 64 of the first tube or guide catheter 32 to close the previously open annulus 68.

Figure 16:
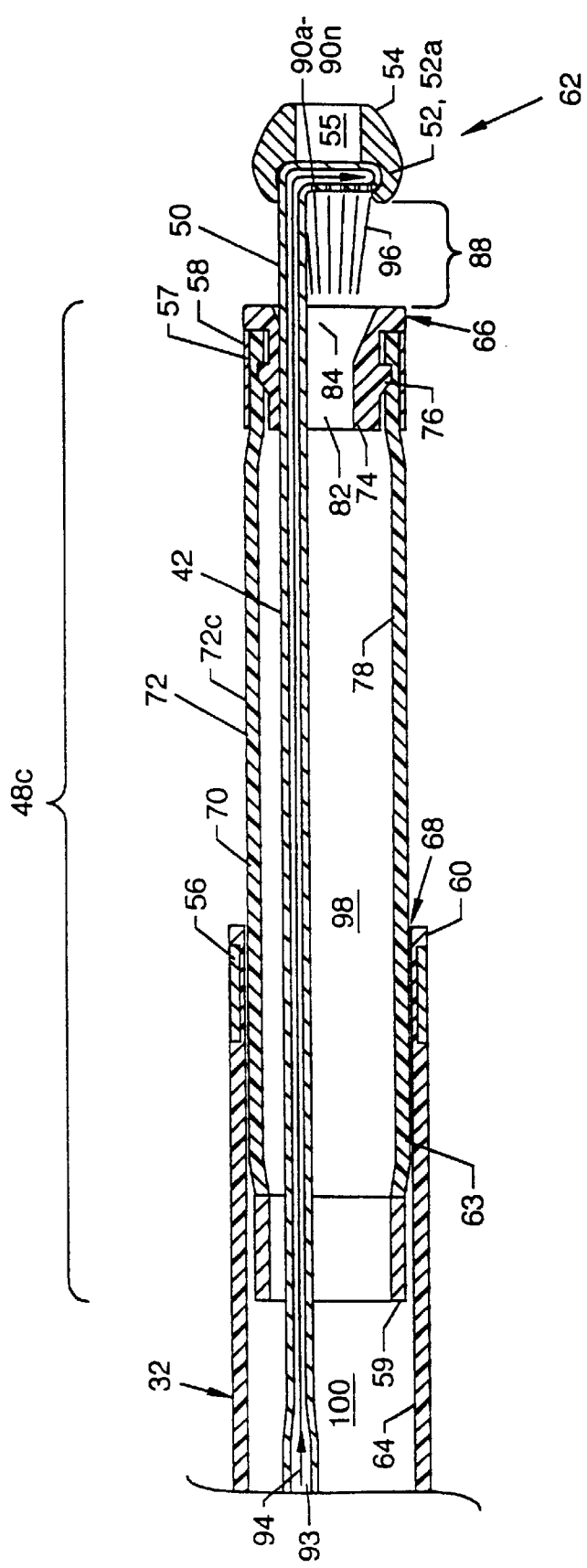
FIG. 16, a second alternative embodiment, illustrates a cross section view of the elements of FIG. 7 featuring an optional non-expandable, non-compliant fit tube.

FIG. 16, a second alternative embodiment, illustrates a cross section view of the elements such as depicted in FIG. 7, including the second tube 42 and an optional flow director 48c in extended concentric alignment with the first tube or guide catheter 32 and associated components. This embodiment operates much the same as previous embodiments, but differs from the previous embodiments in that an optional flow director 48c is provided which includes the components of the flow director 48a with the exception of an exhaust tube 72 in the form of an optional non-expandable, non-compliant close fit exhaust tube 72c. The non-expandable, non-compliant close fit exhaust tube 72c can be fashioned of material, such as, but not limited to, PEBAX or nylon copolymer, for example, and is of a regular shaped structure, such as, but not limited to, a tube. This figure illustrates the pressurized mode where it is desirable to have the annulus 68 not entirely closed. Such an arrangement allows more freedom of longitudinal and rotational movement and maneuverability between the inner catheter assembly 14 and the outer catheter assembly 12 while still maintaining a suitable seal. Freedom of rotational and longitudinal movement is desirable to permit greater flexibility with respect to full and effective positioning of the space 88. Sufficient saline pressure may still be maintained and any pressure loss through the reduced size annulus 68 is negligible.

Figure 17:
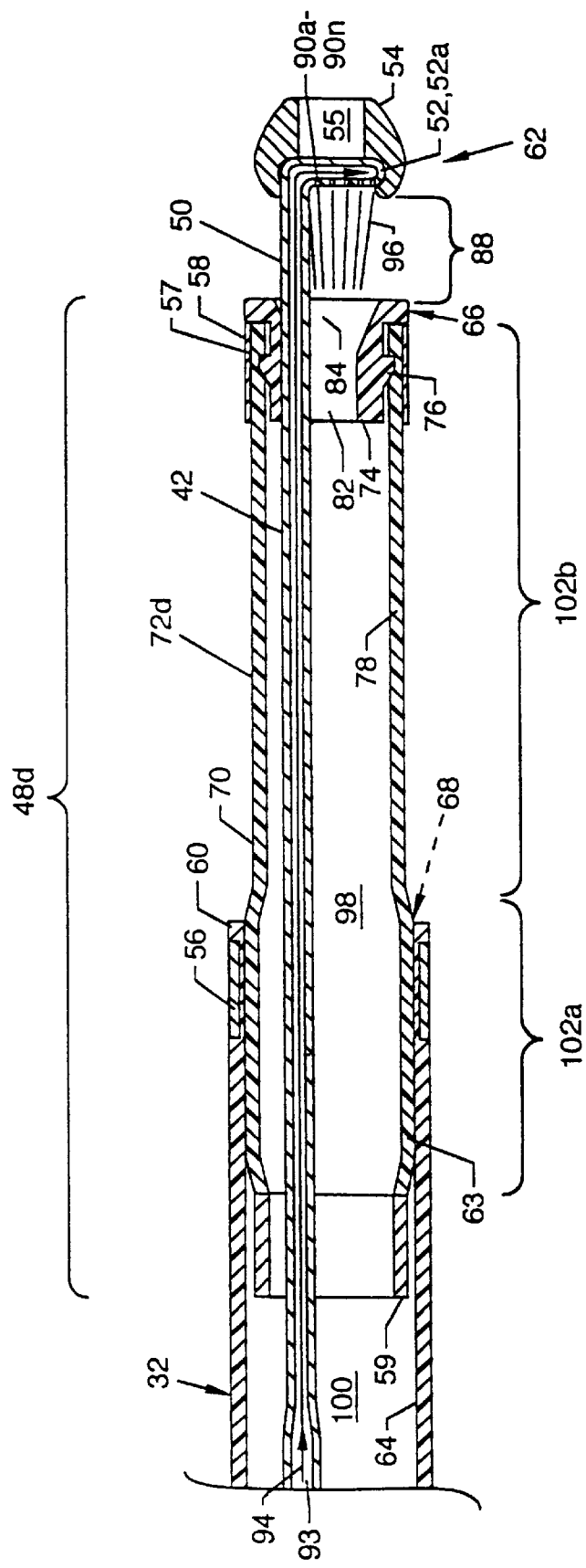
FIG. 17, a third alternative embodiment, illustrates a cross section view of the elements of FIG. 7 featuring a compliant/non-compliant exhaust tube where one segment is more flexible than an adjacent segment.

FIG. 17, a third alternative embodiment, illustrates a cross section view of the elements of FIG. 7, including the second tube 42 and an optional flow director 48d in extended concentric alignment with the first tube or guide catheter 32 and associated components. This embodiment operates much the same as previous embodiments, but differs from the previous embodiments in that an optional flow director 48d is provided which includes the components of the flow director 48a of FIG. 7 with the exception of an exhaust tube 72 in the form of an optional compliant/non-compliant exhaust tube 72d having continuous segments of different durometer characteristics whereby one segment is of different flexibility than an adjacent segment. Segment 102a is of a durometer reading consistent with the compliant expandable exhaust tube 72a, previously described, which allows expansion of the segment 102a, such as previously described. Segment 102b, however, is of a durometer reading which is consistent with the non-compliant expandable exhaust tube 72b such that expansion of the segment 102b is prevented or limited by its own structure to maintain a constant or near constant diameter. Alternatively, the segments 102a and 102b could be of separate construction and joined such as by gluing, ultrasonic welding, fusing, or any suitable method to provide the compliant/non-compliant exhaust tube 72d.

MODE OF OPERATION

Figure 18:
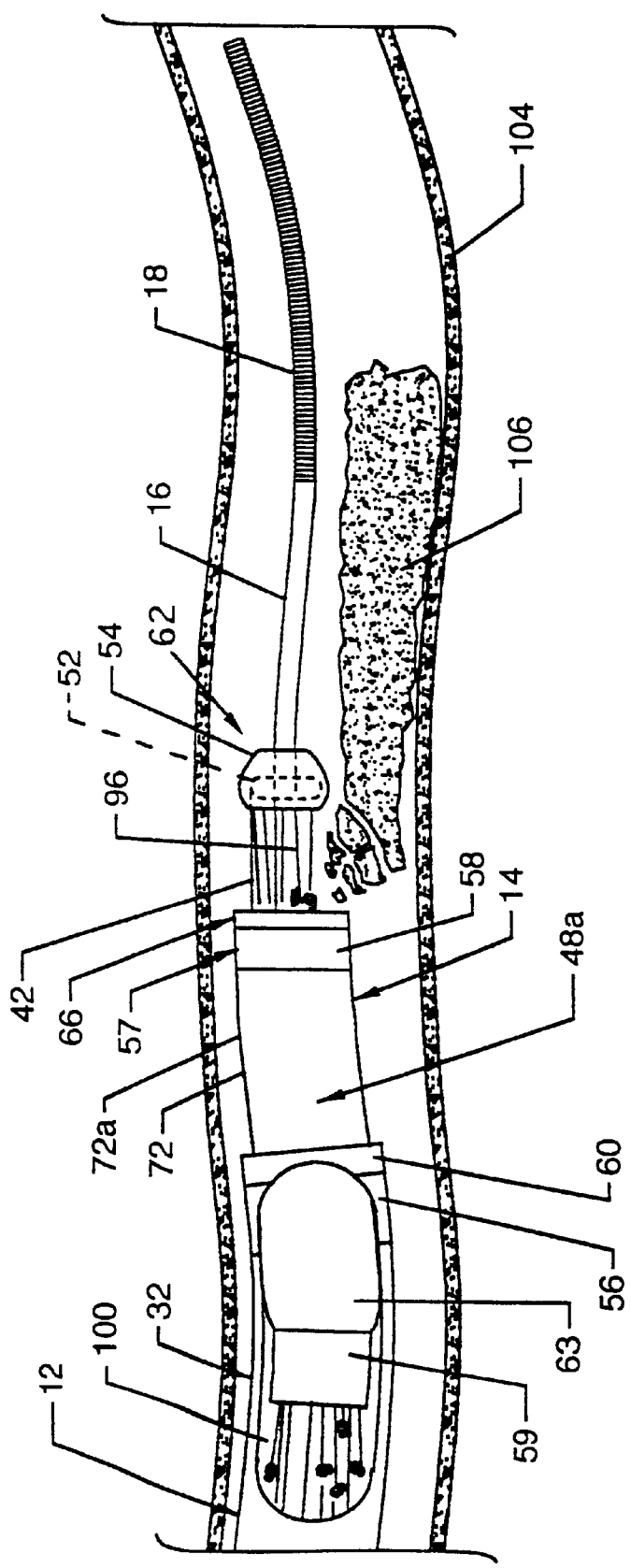
FIG. 18 illustrates a cross section view and in partial cutaway of the distal end of the single operator exchange fluid jet thrombectomy device in operation in a blood vessel.

FIG. 18 illustrates a cross section view in partial cutaway of the distal end of the single operator exchange fluid jet thrombectomy device 10 in operation in a blood vessel 104. FIG. 18, with reference to elements previously described in relation to FIGS. 1–13, best illustrates the mode of operation of the single operator exchange fluid jet thrombectomy device 10 in the performance of the method of the present invention, with particular attention to the distal end 60 of the first tube or guide catheter 32, the flow director 48a, the second tube 42, the jet emanator 52 and the optional jet cap 54 and guidewire 16 positioned in a blood vessel 104, artery or the like at the site of a thrombotic deposit or lesion 106.

The first tube or guide catheter 32, which is flexible and which serves as a flexible evacuation tube, is first advanced to reach a location proximal of the thrombotic deposit or lesion 106. With the distal end 60 of the first tube or guide catheter 32 positioned near the thrombotic deposit or lesion 106, the flexible tip 18 of the guidewire 16 is then introduced into the first tube or guide catheter 32 via the manifold 20 and thence the guidewire 16 is advanced through and past the distal end 60 of the first tube or guide catheter 32 and then along a blood vessel 104 or vein in the patient's body. The guidewire 16 is advanced through the vasculature to and beyond the site of the thrombotic deposit or lesion 106. For a distal coronary vessel or a vessel of the brain, typically the guidewire has a diameter which can range from 0.010–0.018 inch. This procedure can also be applied to larger vessels which require larger diameter guidewires up to 0.038 inch. Once the guidewire 16 has been advanced along the blood vessel 104 and has reached or has been advanced through the thrombotic deposit or lesion 106, the inner catheter assembly 14 can be brought into engagement with the catheter assembly 12. Such engagement is initiated by accommodation of the guidewire 16 by the passage 53 of the jet emanator 52 and the passage 55 of the optional jet cap 54, if incorporated. The inner catheter assembly 14 is then advanced distally whereby the proximal end 17 of the guidewire 16 enters the space 88 and the components of the flow director 48a to subsequently extend proximally from the flow director 48a. Further advancement of the inner catheter assembly 14 along the guidewire 16 brings the jet emanator 52 and optional jet cap 54 and the flow director 48a of the inner catheter assembly 14 and the second tube 42 into aligned accommodation initially by the manifold 20 and then by the first tube or guide catheter 32. The jet emanator 52, the optional jet cap 54, the flow director 48a, which can have a lubricous coating to aid in deployment through the lumen 100 of the first tube or guide catheter 32, and the second tube 42 are then advanced within the lumen 100 of the first tube or guide catheter 32 to a position along the variable displacement distance 86 where the distal end 57 of the exhaust tube 72, in this case in the form of a compliant expandable exhaust tube 72a, and including the inner body 66 are positioned as desired beyond the distal end 60 of the first tube or guide catheter 32, whereby the exhaust tube 72 is aligned to the distal end 60 of the first tube or guide catheter 32. The passage 82 of the inner body 66, the lumen 98 of the exhaust tube 72, and the lumen 100 of the first tube or guide catheter 32 serve as an evacuation tube. The single operator exchange fluid jet thrombectomy device 10 can then be activated by providing high pressure liquid, preferably saline, to the proximal end 33 of the first tube or guide catheter 32 via the manifold 20.

High pressure saline 94, or other liquid, from the manifold 20 is provided and flows through the high pressure lumen 93 of the second tube 42 to enter orifices 90a–90n of the jet emanator 52. The high pressure saline exits the jet emanator 52 as high velocity saline jet flow 96 directed toward the open ramped annular surface 84 and enters into the passage 82 of the inner body 66 at the distal end 57 of the exhaust tube 72. The high pressure saline jet flow operates to close the annulus 68 to ensure positive flow without leak-back through an annulus such as annulus 68, as previously described, and to dislodge tissue from the thrombotic deposit or lesion 106 and entrain the tissue into the saline jet flow 96 where it is broken up into smaller fragments and carried proximally.

Impingement of the saline jet flow 96 into the flow director 48a and the first tube or guide catheter 32 creates a stagnation pressure within the lumen 98 of the exhaust tube 72 and the lumen 100 of the first tube or guide catheter 32 (evacuation lumen) that drives the debris particles of thrombotic deposit or lesion 106 toward the proximal end 33 of the first tube or guide catheter 32.

Subsequent to initial activation, the inner catheter assembly 14 can be advanced over the guidewire 16 through tortuous turns to reach the thrombotic deposits or lesions 106 beyond the region of initial ablative action for further ablative action.

A positive displacement piston pump (not illustrated) can be used to provide liquid, preferably saline, under pressure to the proximal end of the second tube 42. A pressure ranging from 50–50,000 psi will provide the energy to create a useful high velocity saline jet flow 96 as the saline exits the jet orifices 90a–90n located at the proximal surface of the jet emanator 52. The flow rate of saline can be controlled by adjusting the pumping rate of the positive displacement piston pump. The proximal end 33 of the first tube or guide catheter 32 interfaces with a metering device through the Luer connection 26 at the manifold branch 30, for example, a roller pump, prior to discharge of the evacuated thrombotic debris into a collection bag for disposal. The rate of evacuation can be controlled by adjusting the rate of the roller pump. The rate of saline inflow can be balanced with the rate of removal of thrombotic debris by simultaneous adjustment of the piston pump and the roller pump. The rate of saline inflow can be less than, equal to, or greater than the rate of removal of thrombotic debris. The rate of thrombus removal can be set to slightly exceed the rate of saline inflow to reduce the likelihood for distal embolization of thrombotic tissue.

Because numerous modifications may be made to the method without departing from the spirit thereof, the scope of the method is not to be limited to the embodiments illustrated and described that are involved in the method. Rather, the scope of the method is to be determined by the appended claims and their equivalents.

Figure 24:
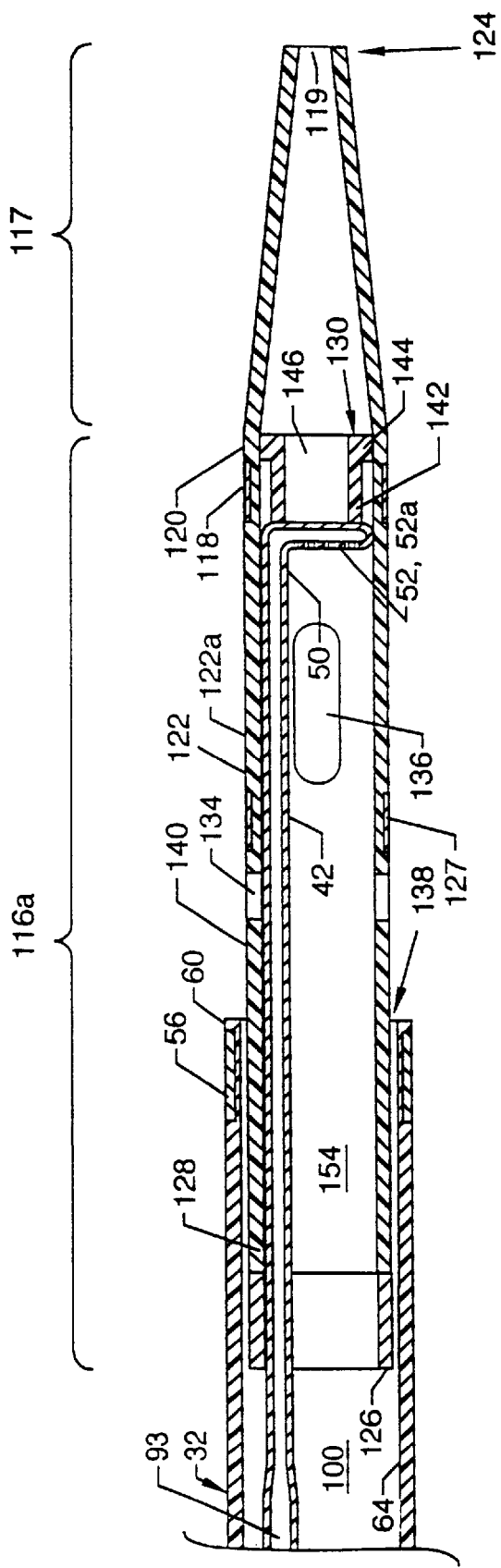
FIG. 24 illustrates a cross section view of the distal end of the first tube or guide catheter and the crossflow/flow director in the unpressurized mode, along line 24—24 of FIG. 19.

FIG. 19, a fourth alternative embodiment, illustrates a side view of a single operator exchange fluid jet thrombectomy device 110 useful for the removal of thrombus, and FIG. 20 illustrates a semi-exploded side view of the single operator exchange fluid jet thrombectomy device 110. The single operator exchange fluid jet thrombectomy device 110 includes two major assemblies: namely, an outer catheter assembly 12, as previously described in detail and which is a core assembly, and an inner catheter assembly 114 configured to function as a crossflow thrombectomy catheter, which has been substituted or exchanged for the previously described inner catheter assembly 14 and which is shown as an example of inner catheter assemblies which can be exchanged with other styles or designs of inner catheter assemblies as desired to fit substantially within and to be incorporated with the outer catheter assembly 12. The inner catheter assembly 114, when in use, aligns substantially concentrically to and mostly within the outer catheter assembly 12 and extends beyond both ends of the outer catheter assembly 12. Guidewire 16 including a flexible tip 18 at one end and a proximal end 17 opposing the flexible tip 18 is shown in substantially concentric alignment to both the outer catheter assembly 12 and the inner catheter assembly 114. Externally visible components, or portions of components, of the outer catheter assembly 12 correspond to the previous descriptions. Much of the structure of the previously described inner catheter assembly 14 is incorporated and utilized in the inner catheter assembly 114. Externally visible components or portions of components of the inner catheter assembly 114 of the single operator exchange fluid jet thrombectomy device 110 include the high pressure second tube 42, the transitional filter housing/high pressure connection/stop assembly 44 concentrically aligned to and secured over and about the proximal end 46 of the second tube 42, a crossflow/flow director 116a having a lumen 154 (FIG. 24) and comprised substantially of an exhaust tube 122 in the form of a compliant expandable exhaust tube 122a aligned over and about the distal end 50 (FIG. 4) of the high pressure second tube 42, a flexible tapered tip 117 having a passage 119 (FIG. 21) and being contiguous with and extending distally from the exhaust tube 122 of the crossflow/flow director 116a, the end of the flexible tapered tip 117 at the passage 119 being the distal end 124 of the inner catheter assembly 114, a jet emanator 52 having a passage 53 (FIG. 22) at the distal end 50 of the second tube 42, and a radio-opaque marker 118 located along and at the distal end 120 of the crossflow/flow director 116a and aligned adjacent to and in close proximity to the jet emanator 52 to mark the substantially co-located distal end 50 of the second tube 42 and distal end 120 of the crossflow/flow director 116a. An optional radio-opaque marker 126 can also be located and attached to or be integral to the proximal end 128 of the crossflow/flow director 116a and included, along with radio-opaque marker 118, as an optional integral part of the crossflow/flow director 116a. An inner body 130 of either metal or plastic (FIG. 22), part of the crossflow/flow director 116a, frictionally engages the distal end 120 of the crossflow/flow director 116a interior of the exhaust tube 122 of the crossflow/flow director 116a, as shown in FIG. 24. Also featured on the exhaust tube 122 of the crossflow/flow director 116a are one or more outflow orifices 134 and one or more inflow orifices 136 for creating a crossflow so that the inner catheter assembly will function as a crossflow thrombectomy catheter. An optional radio-opaque marker 127 can be included on the exhaust tube 122 of the crossflow/flow director 116a between one or more outflow orifices 134 and one or more inflow orifices 136.

Figure 21:
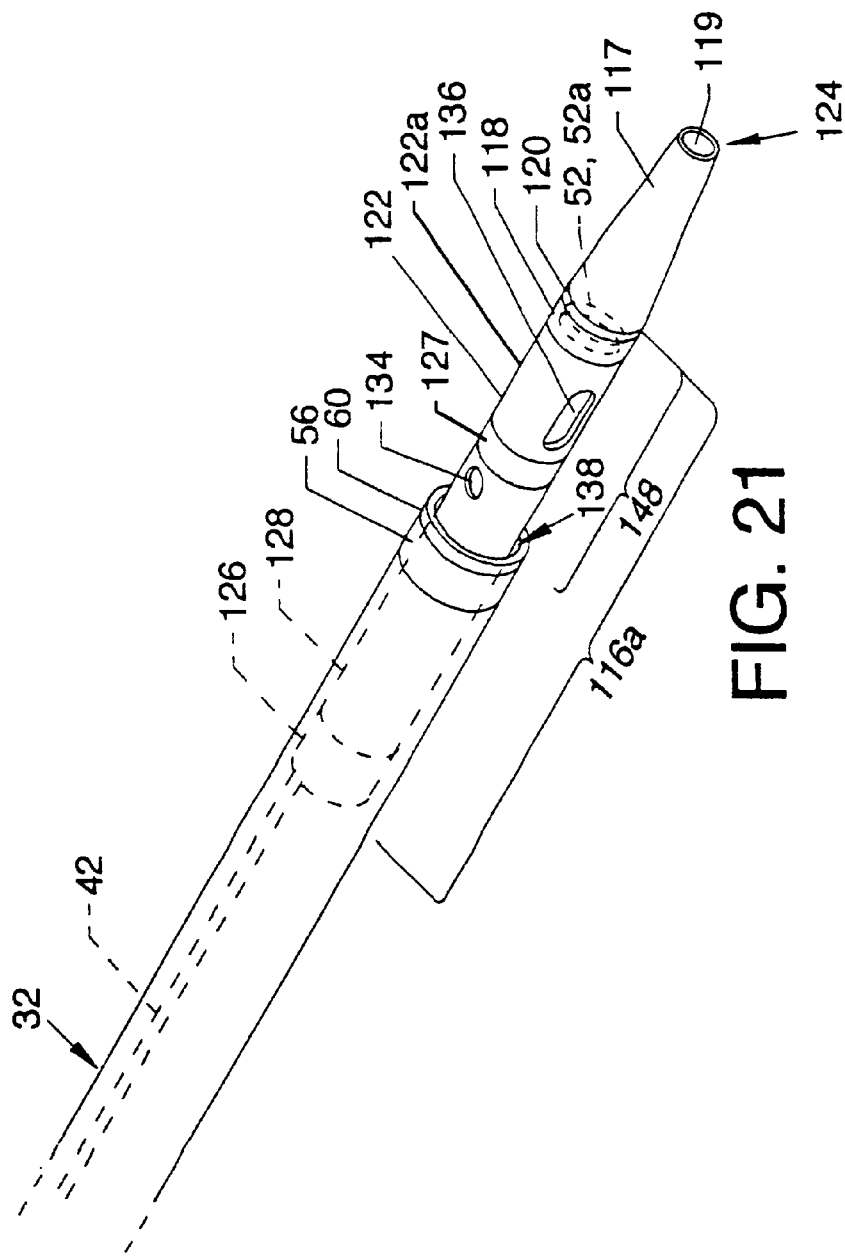
FIG. 21 illustrates an isometric view of the distal end of the first tube or guide catheter with a portion of the inner catheter assembly of FIG. 20 protruding therefrom.
Figure 22:
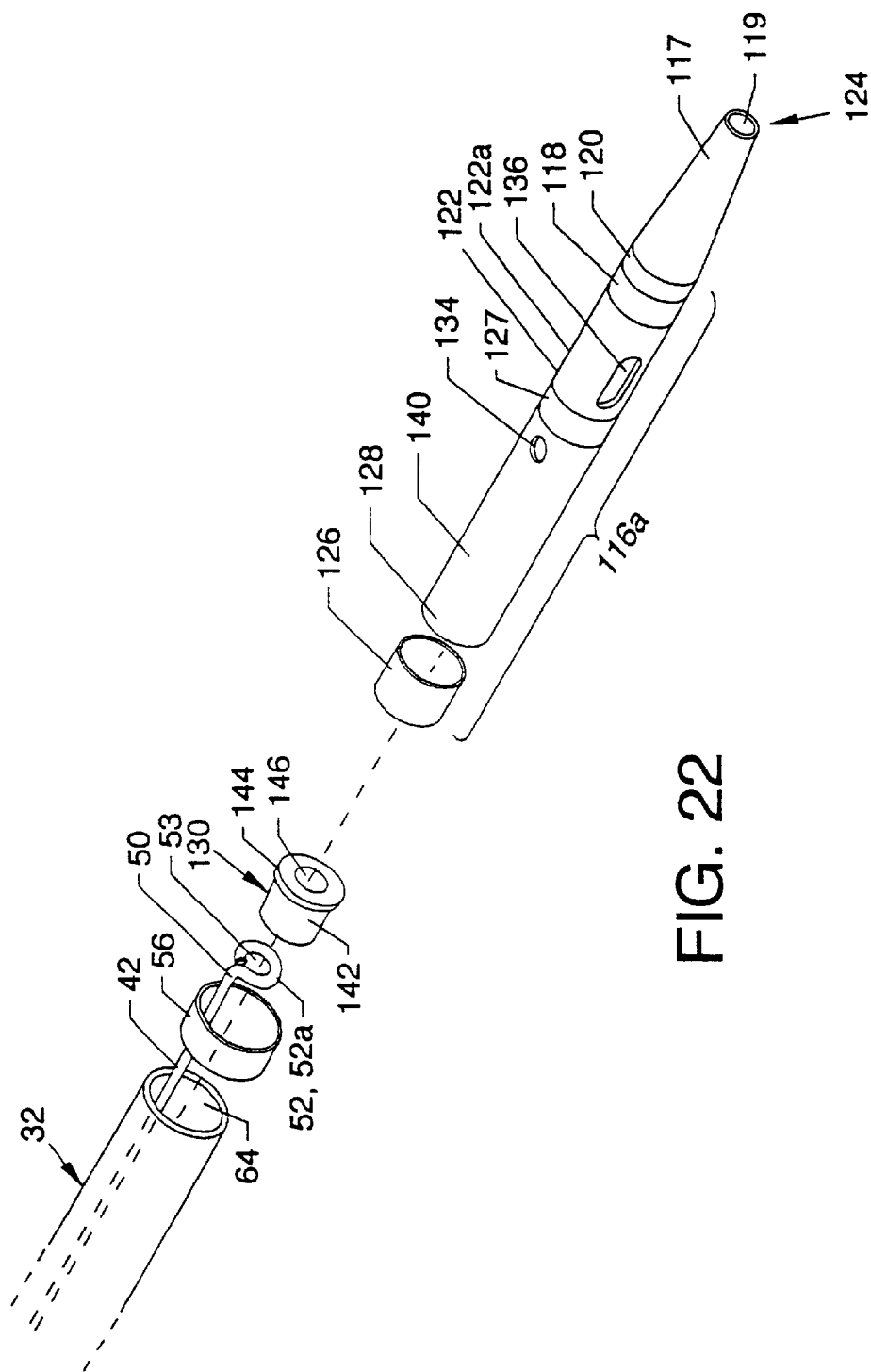
FIG. 22 illustrates an exploded view of the components of FIG. 21.

FIG. 21 illustrates an isometric view of the distal end 60 of the first tube or guide catheter 32 with a portion of the inner catheter assembly 114 protruding therefrom, and FIG. 22 illustrates an exploded view of the components of FIG. 21. Illustrated in particular is the relationship of the components aligned in the distal end 60 of the first tube or guide catheter 32 during use of the invention. Guidewire 16 is not shown for purposes of brevity and clarity. The second tube 42 extends proximally through the crossflow/flow director 116a, and collectively the second tube 42 and the crossflow/flow director 116a extend proximally through the first tube or guide catheter 32. As illustrated in the unpressurized mode and as also illustrated in FIG. 24, it is noted that an annulus 138 is formed between the interior annular surface 64 of the first tube or guide catheter 32 and an outer annular surface 140 of the exhaust tube 122, which is in the form of a compliant expandable exhaust tube 122a. The inner body 130 includes a reduced radius neck 142 extending proximally from a larger radius shoulder 144 and also includes a passage 146 for accommodation of the guidewire 16. The jet emanator 52, in the form of a toroidal loop 52a, aligns to and secures, such as by welding, gluing or other suitable means, to the proximal region of the inner body 130, as shown in FIG. 24. Swaging of the radio-opaque marker 118 over the exhaust tube 122 and inner body 130 secures the assembly in order to keep the distance from the jet emanator 52 and inflow orifices 136 constant for optimal thrombectomy function. During normal pressurized operation, the exhaust tube 122 expands to cause the outer annular surface 140 of the exhaust tube 122 to expand and impinge the interior annular surface 64 of the first tube or guide catheter 32, thereby closing and eliminating the annulus 138, much the same as previously described for use of the inner catheter assembly 14 with the outer catheter assembly 12 and as later shown in FIG. 25. Also, pressurized saline flow passes from the outflow orifice(s) 134 to dislodge thrombotic materials which are returned to the interior of lumen 154 of the crossflow/flow director 116a through the inflow orifice(s) 136 where the thrombus is macerated and then pushed through the crossflow/flow director 116a and into the first tube or guide catheter 32 for removal from the body.

During performance of the method of the invention the outer catheter assembly 12 is advanced along a vein or other blood vessel or passage proximal to a vascular site containing thrombus followed by the passage of the guidewire 16 through and beyond the distal end 60 of the first tube or guide catheter 32 and thence followed by advancement of the inner catheter assembly 114 along the guidewire 16 and along the interior of the outer catheter assembly 12. As the second tube 42 is positioned, during pressurized or unpressurized operation, the crossflow/flow director 116a, the jet emanator 52, along with the second tube 42, move and position as a unit to a desired position along a variable displacement distance 148 which is the distance from the distal end 60 of the first tube or guide catheter 32 to and including the distal end 120 of the crossflow/flow director 116a. The variable displacement distance 148 can range from a minimum distance where the jet emanator 52 at the distal end 50 of the second tube 42 (distal end 120 of the crossflow/flow director 116a) is positioned just inside the distal end 60 of the first tube or guide catheter 32, where no thrombus ablation occurs, to a maximum distance where the jet emanator 52 has advanced to a position well beyond the distal end 60 of the first tube or guide catheter 32, thus positioning the proximal end 128 of the crossflow/flow director 116a along a region proximal to the distal end 60 of the first tube or guide catheter 32, whereby a major portion of the exhaust tube 122, the entire inner body 130, and the jet emanator 52 are distally located with reference to the distal end 60 of the first tube or guide catheter 32. Incremental advancement distally of the crossflow/flow director 116a distally reveals the inflow orifice(s) 136 and the outflow orifice(s) 134 sequentially. In some cases, it would be advantageous to operate with the outflow orifices 134 blocked when treating a soft unstable thrombus to remove easily embolized material, and then operate with the outflow orifices 134 exposed to remove the more strongly adherent thrombus or other tissue. At or near this extended position, further distal movement is prevented by impingement of the transitional filter housing/high pressure connection/stop assembly 44 with the hemostasis nut/stop 22, which are shown in FIG. 19.

Figure 23:
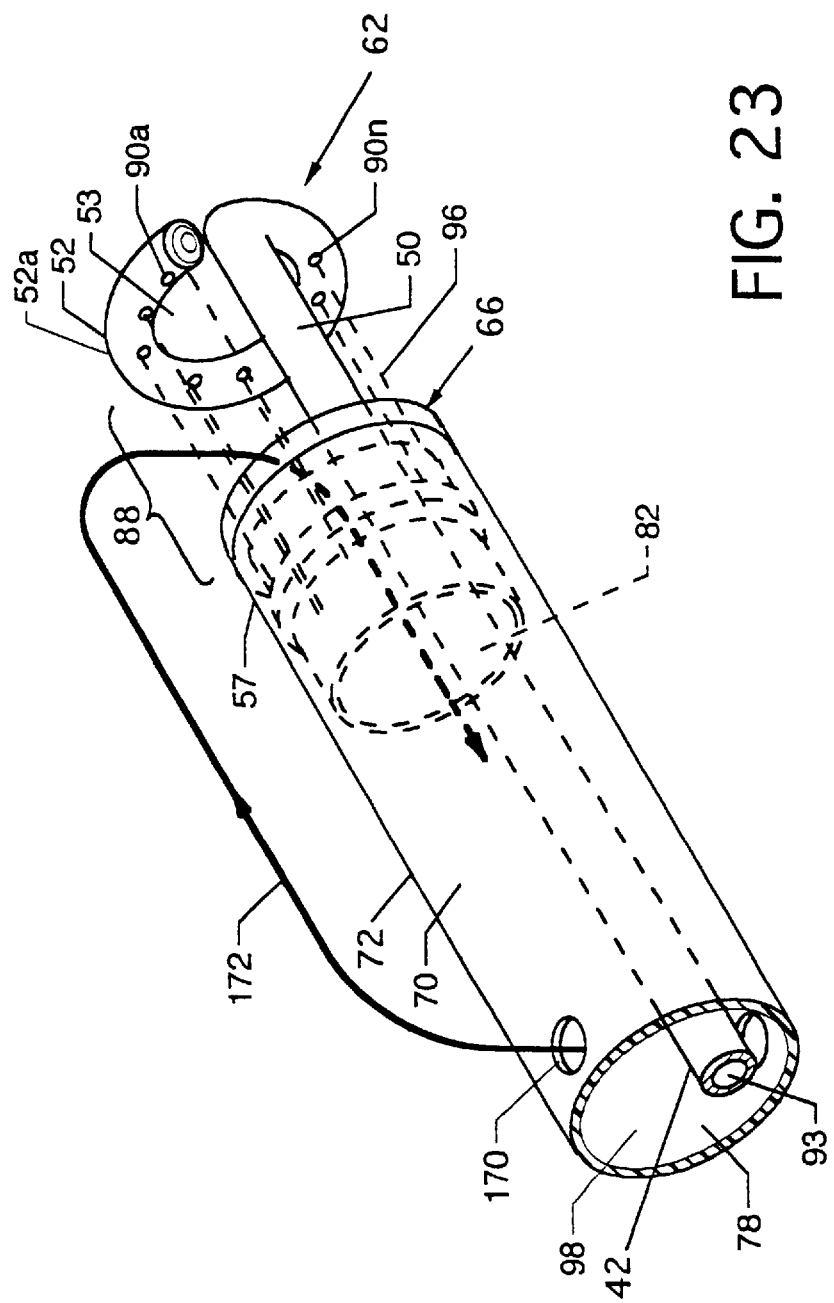
FIG. 23, a fifth alternative embodiment, illustrates a view of the elements of FIG. 6 including one or more outflow orifices.

FIG. 23, a fifth alternative embodiment, illustrates a view of the elements of FIG. 6 including one or more optional outflow orifice(s) 170 for incorporation of saline crossflow with the inner catheter assembly 14 of the single operator exchange fluid jet thrombectomy device shown in FIG. 2. High pressure saline jet flow 96 emanating from the jet emanator 52 initially enters passage 82, flows through passage 82 into the exhaust tube 72 to outflow orifice(s) 170, exits radially to form a crossflow jet 172 to impinge and entrain thrombotic deposits or lesions, and thence is directed distally and drawn again through passage 82 of the inner body 66, which functions as an inflow orifice, where the thrombotic deposits or lesions are macerated by the high pressure saline jet flow 96 to be further entrained by the high pressure saline jet flow 96 for travel along the lumen 98 of the exhaust tube 72. Thus, maceration including the attributes of saline crossflow jets, such as crossflow jet 172, and the attributes of maceration occurring at the space 88 are combined.

Figure 25:
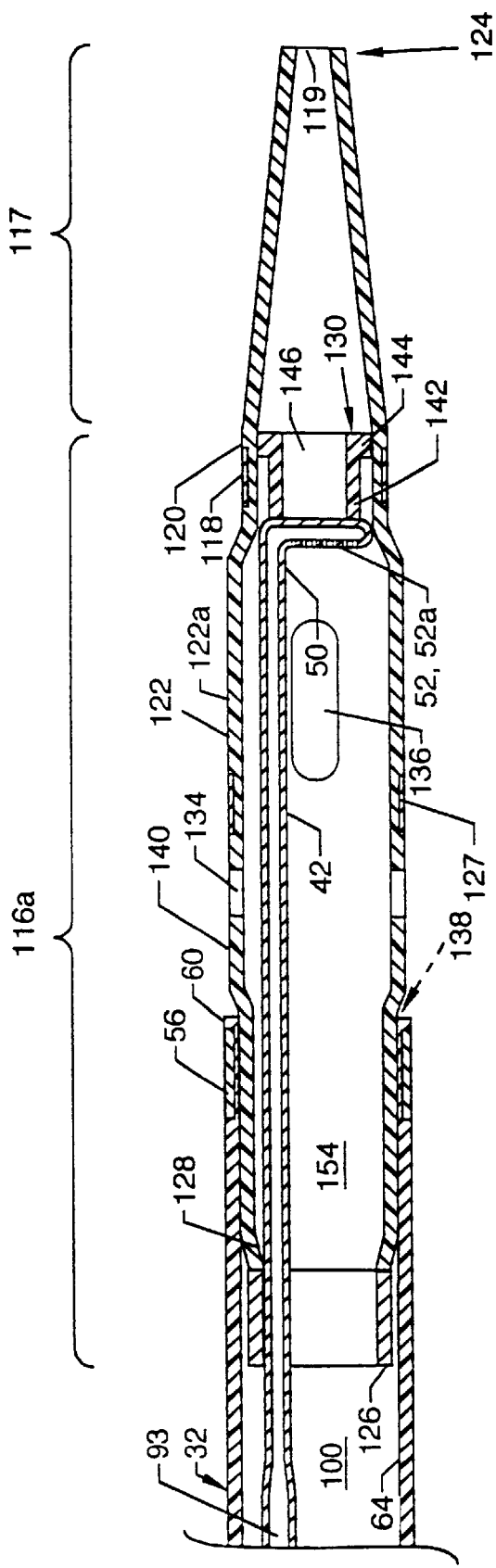
FIG. 25 illustrates a cross section view of the elements of FIG. 24 in the pressurized mode.

FIGS. 24 and 25 substantially illustrate the mutual accommodation and the alignment of the distal portions of the outer catheter assembly 12 and inner catheter assembly 114.

FIG. 24 illustrates a cross section view of the distal end 60 of the first tube or guide catheter 32 and the crossflow/flow director 116a in the unpressurized mode, including the second tube 42 and the crossflow/flow director 116a in extended concentric alignment with the first tube or guide catheter 32 and associated components, along line 24—24 of FIG. 19. Illustrated in particular is the relationship of the interior annular surface 64 of the first tube or guide catheter 32 and the outer annular surface 140 of the exhaust tube 122, in the form of a compliant expandable exhaust tube 122a, which form the annulus 138 which is elongated. Jet orifices 90a–90n (FIG. 6) located at jet emanator 52 at the distal end 50 of the second tube 42 are directed rearwardly and slightly towards the longitudinal axis of the exhaust tube 122.

The maximum distal position of the distal end 50 of the second tube 42 with respect to the distal end 60 of the first tube or guide catheter 32 can be determined by using a suitable length second tube 42. The distal end of the transitional filter housing/high pressure connection/stop assembly 44 (FIG. 19) and the hemostasis nut/stop 22 (FIG. 19) can contact each other to limit the distal movement of the second tube 42 and the attached crossflow/flow director 116a. The location of the crossflow/flow director 116a and its position with respect to the distal end 60 of the first tube or guide catheter 32 can also be determined by observation of the relationship of one or more of the following components, including the radio-opaque marker 56 at the distal end 60 of the first tube or guide catheter 232, the radio-opaque markers 126 and 127, the radio-opaque marker 118, the inner body 130, the flexible tapered tip 117, or of other components by known observation methods.

FIG. 25 illustrates a cross section view of the elements of FIG. 24, including the second tube 42 and the crossflow/flow director 116a in extended concentric alignment with the first tube or guide catheter 32 and associated components, in the pressurized mode. Subsequent to proper positioning of the appropriate component involved in the method in a vessel or other body member in the unpressurized mode, saline 150, under high pressure, is injected through the inner catheter assembly 114 through the high pressure lumen 93 of the second tube 42 and delivered to the distal end 50 to emanate as saline jet flow 152 from the jet orifices 90a–90n of the jet emanator 52. The pressurized saline jet flow 152 is directed proximally into the lumen 154 of the crossflow/flow director 116a where it (1) operates to pressurize the exhaust tube 122 causing the exhaust tube 122, in the form of a compliant expandable exhaust tube 122a, to expand and force the outer annular surface 140 of the exhaust tube 122 to closingly seal against the interior annular surface 64 of the first tube or guide catheter 32, (2) exits one or more outflow orifices 134 to break up and erode the thrombotic tissue, and (3) entrains loosened thrombotic tissue adjacent to and about the exposed portion of the crossflow/flow director 116a and to return the loosened thrombotic material through one or more inflow orifices 136. Positive pressurized flow of the pressurized saline prevents saline from back flowing out of the previously open annulus 138 which has been pressurized to the closed position by creation of a seal between the inner catheter assembly 114 within the outer catheter assembly 12 and allows the saline to travel while carrying the entrained particles of thrombotic tissue under full pressurized force along the lumen 154 of the crossflow/flow director 116a and along a lumen 100 central to the first tube or guide catheter 32 and thence through a catheter lumen interior to the manifold 20 and outwardly through the angled manifold branch 30 where its flow may or may not be regulated. The ability to insert and maneuver the inner catheter assembly 114 within the outer catheter assembly 12 freely and unhampered and then to subsequently effect a seal between the inner catheter assembly 114 and the outer catheter assembly 12 while maintaining maneuverability contributes to the novelty, efficiency, and usefulness of the method of the invention.

Figure 26:
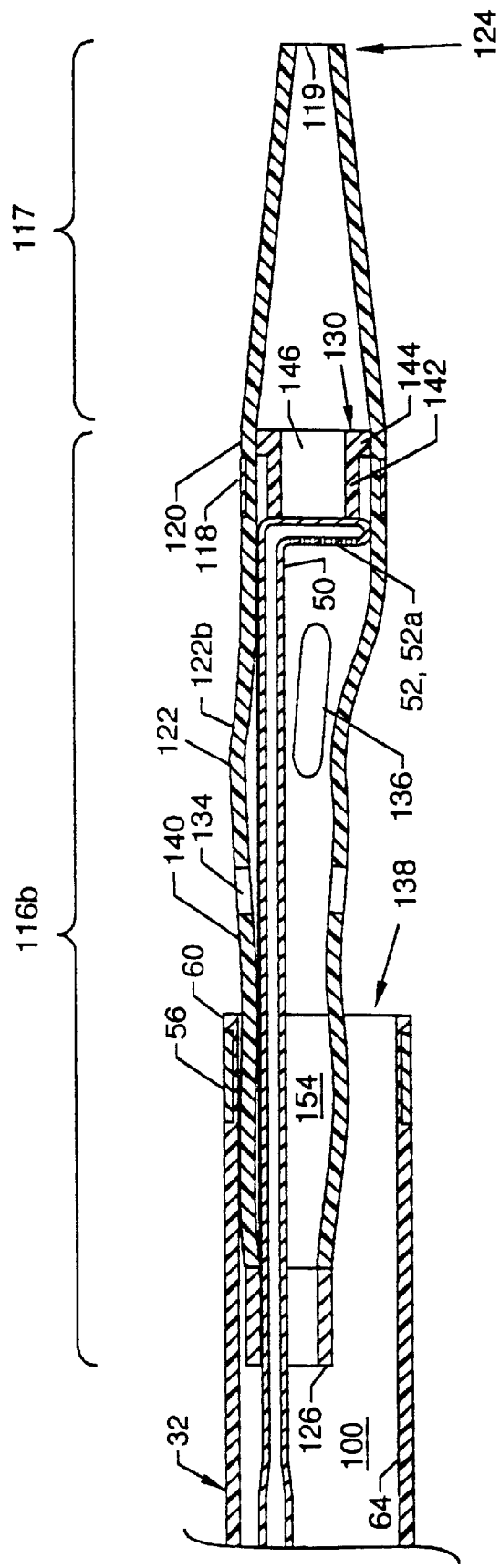
FIG. 26, a sixth alternative embodiment, illustrates a cross section view of the elements of FIG. 24 featuring a non-compliant expandable exhaust tube.

FIG. 26, a sixth alternative embodiment, illustrates a cross section view of the elements of FIG. 24, including the second tube 42 and an optional crossflow/flow director 116b in loose and non-regular alignment with the first tube or guide catheter 32 and associated components. This embodiment operates much the same as a previous embodiment(s), but differs from the previous embodiments in that an optional crossflow/flow director 116b is provided which includes the components of the crossflow/flow director 116a with the exception of an exhaust tube 122 in the form of a non-compliant expandable exhaust tube 122b. The non-compliant expandable exhaust tube 122b can be fashioned of material, such as, but not limited to, flexible polyethylene or polyethylene terephthalate, for example, and can be expanded from an irregular or baggy appearing tubular structure to a regular appearing shaped structure, such as shown in FIG. 27.

Figure 27:
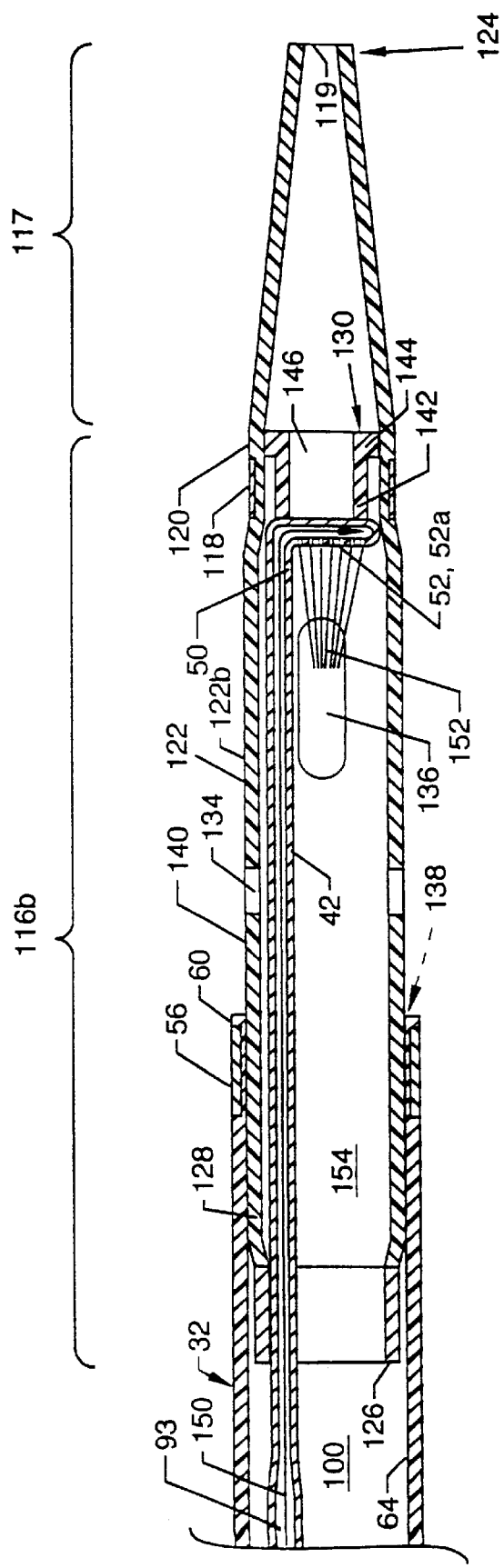
FIG. 27 illustrates the non-compliant expandable exhaust tube of FIG. 26 in the inflated mode to close the previously open annulus.

FIG. 27 illustrates a cross section view of the elements of FIG. 26 in the pressurized mode where the exhaust tube 122 in the form of a non-compliant expandable exhaust tube 122b is pressurized by high pressure saline 150 emanating as saline jet flow 152 from a jet emanator 52, depicted specifically as a toroidal loop 52a, thereby causing the non-compliant expandable exhaust tube 122b to expandingly assume a regular shape and structure which forces the outer surface 140 (now annular) to closingly seal against the interior annular surface 64 of the first tube or guide catheter 32 to close the previously open annulus 138.

Figure 28:
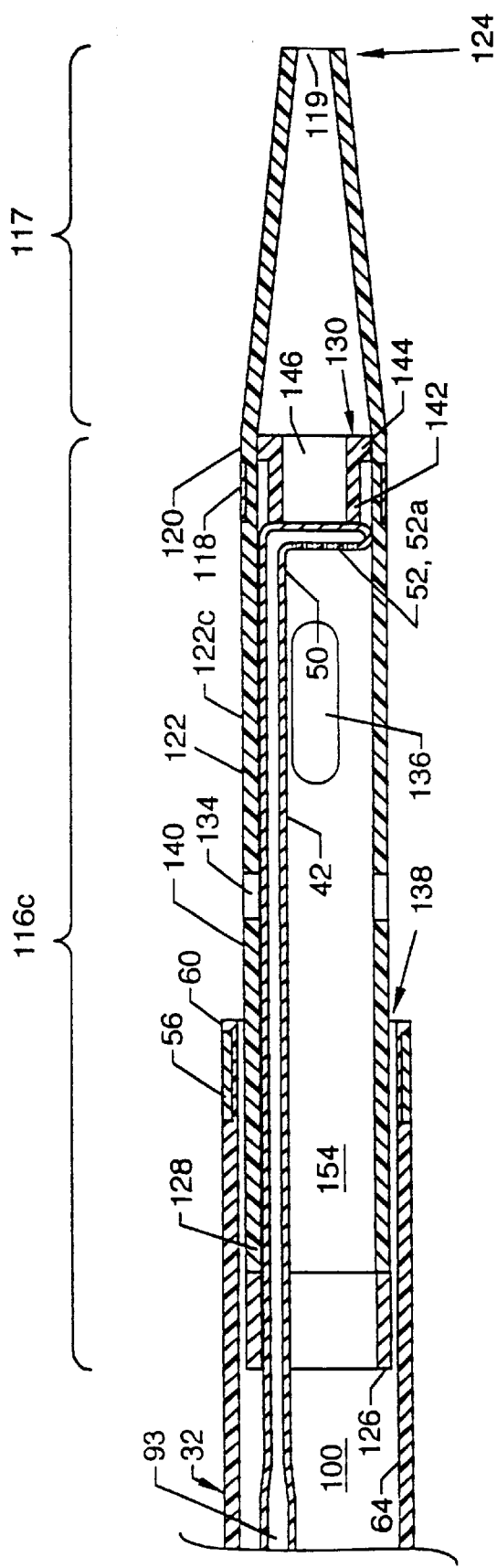
FIG. 28, a seventh alternative embodiment, illustrates a cross section view of the elements of FIG. 24 featuring an optional non-expandable, non-compliant close fit exhaust tube.

FIG. 28, a seventh alternative embodiment, illustrates a cross section view of the elements of FIG. 24, including the second tube 42 and an optional flow director 116c in extended concentric alignment with the first tube or guide catheter 32 and associated components. This embodiment operates much the same as previous embodiments, but differs from the previous embodiments in that an optional flow director 116c is provided which includes the components of the flow director 116a with the exception of an exhaust tube 122 in the form of an optional non-expandable, non-compliant close fit exhaust tube 122c. The non-expandable, non-compliant close fit exhaust tube 122c can be fashioned of material, such as, but not limited to, PEBAX or nylon copolymer, for example, and is of a regular shaped structure, such as, but not limited to, a tube. This figure illustrates the pressurized mode where it is desirable to have the annulus 138 not entirely closed. Such an arrangement allows more freedom of longitudinal and rotational movement and maneuverability between the inner catheter assembly 114 and the outer catheter assembly 12 while still maintaining a suitable seal. Freedom of rotational movement is desirable to permit greater flexibility with respect to full and effective radial positioning of the inner catheter assembly 114. Sufficient saline pressure may still be maintained and any pressure loss through the reduced size annulus 138 is negligible.

Figure 29:
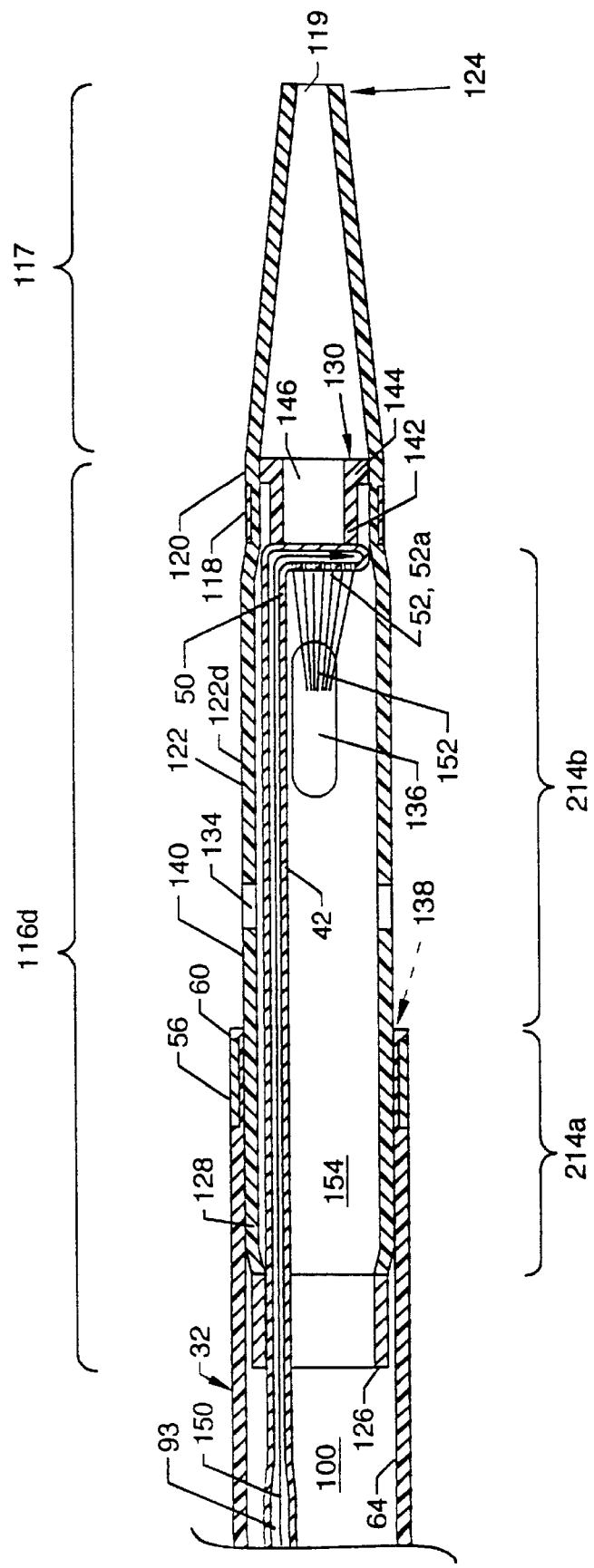
FIG. 29, an eighth alternative embodiment, illustrates a cross section view of the elements of FIG. 24 featuring an optional compliant/non-compliant exhaust tube.

FIG. 29, an eighth alternative embodiment, illustrates a cross section view of the elements of FIG. 24, including the second tube 42 and an optional flow director 116d in extended concentric alignment with the first tube or guide catheter 32 and associated components. This embodiment operates much the same as previous embodiments, but differs from the previous embodiments in that an optional flow director 116d is provided which includes the components of the flow director 116a of FIG. 24 with the exception of an exhaust tube 122 in the form of an optional compliant/non-compliant exhaust tube 122d having continuous segments of different durometer characteristics whereby one segment is more flexible than an adjacent segment. Segment 214a is of a durometer reading consistent with the compliant expandable exhaust tube 122a previously described which allows expansion of the segment 214a, such as previously described. Segment 214b, however, is of a durometer reading which is consistent with the non-compliant expandable exhaust tube 122b such that expansion of the segment 214b is prevented or limited by its own structure to maintain a constant or near constant diameter. Alternatively, the segments 214a and 214b could be of separate construction and joined such as by gluing, ultrasonic welding, fusing, or any suitable method to provide complaint/non-compliant the exhaust tube 122d.

MODE OF OPERATION

Figure 30:
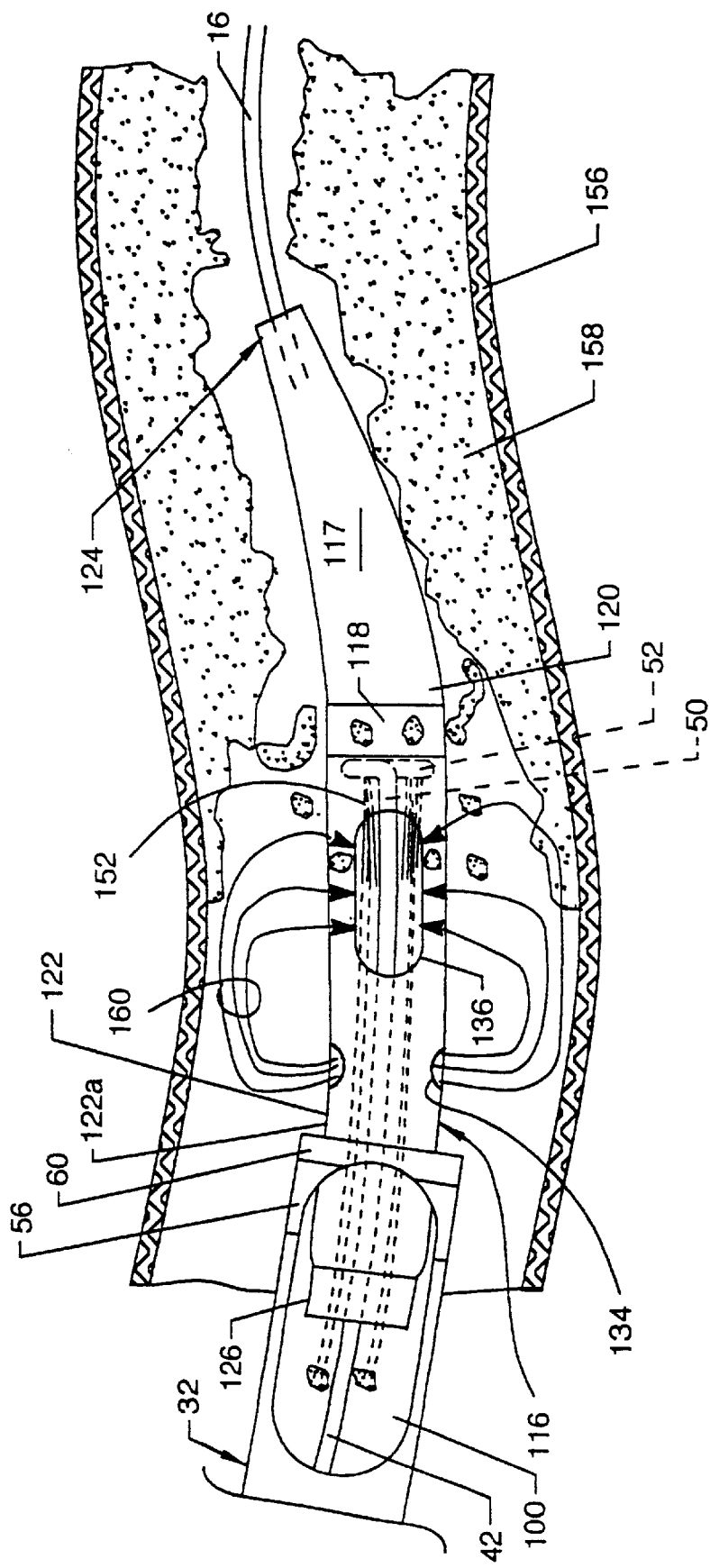
FIG. 30 illustrates a view in cross section and in partial cutaway of the mode of operation of the single operator exchange fluid jet thrombectomy device utilizing the inner catheter assembly of FIG. 24.

FIG. 30 illustrates a cross section view in partial cutaway of the mode of operation of the single operator exchange fluid jet thrombectomy device 110 in the performance of the method of the present invention, with particular attention to the distal end 120 of the crossflow/flow director 116a and the flexible tapered tip 117 positioned in a blood vessel 156, artery or the like at the site of a thrombotic deposit or lesion 158. High velocity jet flow 152 of saline (or other suitable fluid) is shown being emitted in a proximal direction from the jet emanator 52 to sealingly expand the exhaust tube 122 of the crossflow/flow director 116a and to impinge upon and carry away thrombotic deposits or lesions 158. Other jet emanators can be incorporated at the distal end 50 of the second tube 42 as an alternative to the jet emanator 52 illustrated in this figure to emanate or emit one or more high velocity jet flow(s) 152 distally along or near the longitudinal axis of the second tube 42 and the exhaust tube 122 to accomplish the same purpose as that described for the jet emanator 52. The high velocity jet flow(s) 152 of saline pass outwardly through the outflow orifice(s) 134 in a radial direction creating crossflow jet(s) 160 (lower velocity jet(s)) directed outwardly toward the wall of the blood vessel 156 and are influenced by the low pressure at the inflow orifice(s) 136 to cause the crossflow jet(s) 160 to flow circumferentially and distally to impinge on, provide drag forces on, and break up thrombotic deposits or lesions 158 and to, by entrainment, urge and carry along the particles of thrombotic deposits or lesions 158 through the inflow orifice(s) 136, a relatively low pressure region, into the high velocity jet flows 152 where the thrombus is further macerated into microscopic particles, and into the exhaust lumen 154 (FIG. 24). The entrainment through the inflow orifice(s) 136 is based on entrainment by the high velocity jet flow(s) 152. The outflow is driven by internal pressure which is created by the high velocity jet flow(s) 152 and the fluid entrained through the inflow orifice(s) 136. Enhanced clot removal is attainable because of the recirculation pattern established between inflow and outflow orifices 136 and 134, which creates a flow field that maximizes drag force on wall-adhered thrombus. Since the entrained thrombus is macerated into microscopic particles, those particles that exit the outflow orifices 134 are not of sufficient size to significantly block the distal circulation, and will be re-entrained into the inflow orifices 136 at a high rate.

Figure 31:
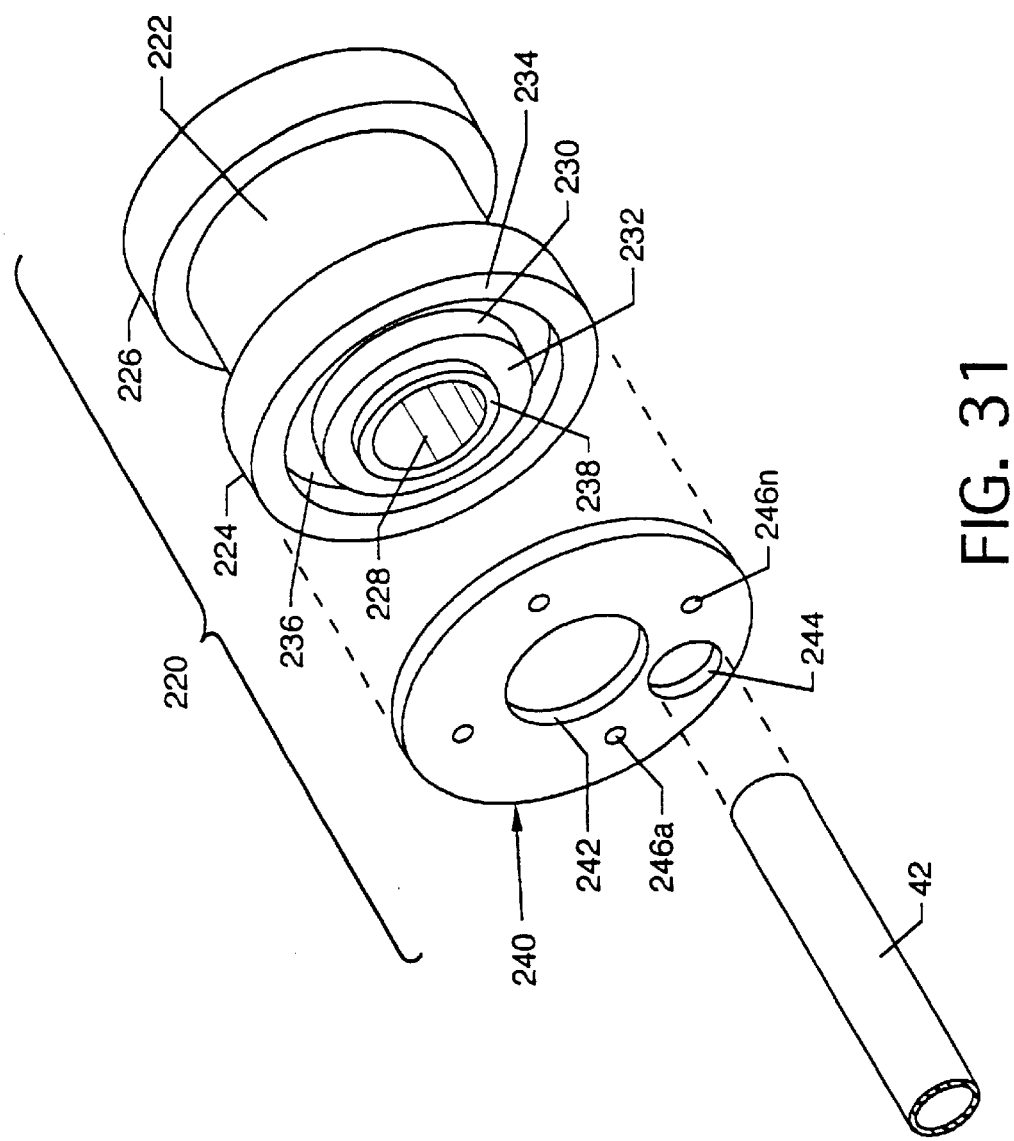
FIG. 31, a ninth alternative embodiment, illustrates an exploded view of a jet emanator in the form of a jet cap.
Figure 32:
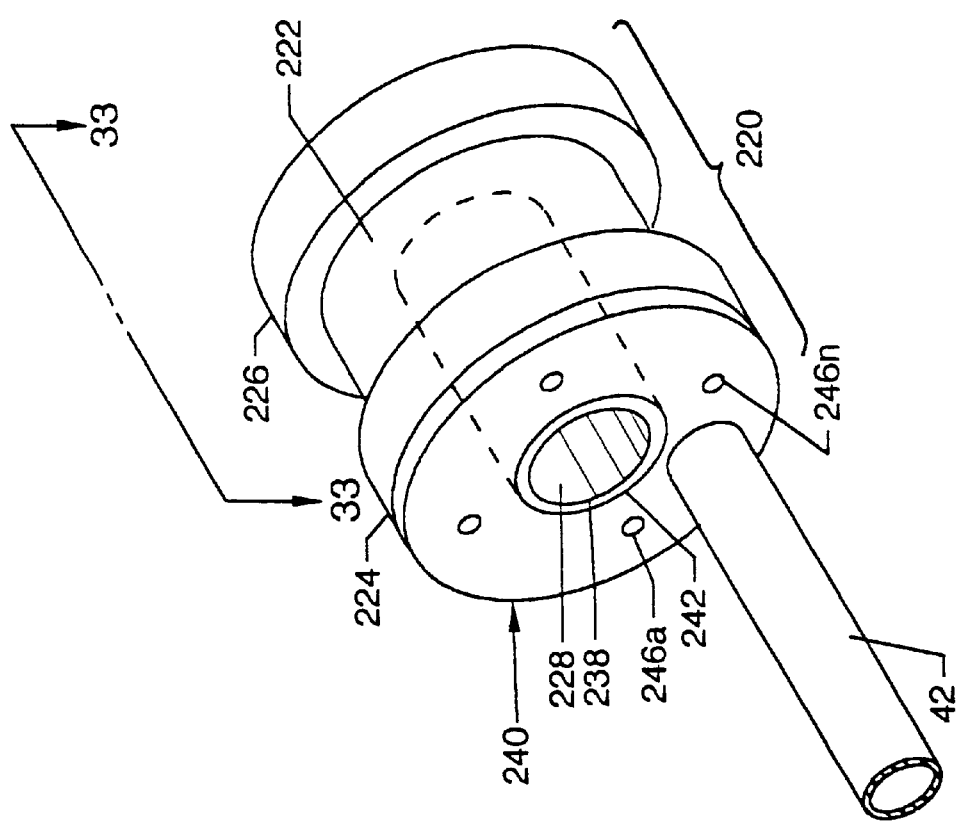
FIG. 32 illustrates an assembled view of the elements of FIG. 31.

FIGS. 31 and 32, a ninth alternative embodiment, illustrate an exploded view and an assembled view of a jet emanator in the form of a jet cap 220, which can be utilized in the inner catheter assembly 114 of the single operator fluid jet exchange thrombectomy device 110. The jet cap 220 is substantially a combination of an emanator and an inner body and the jet cap 220 can be utilized in lieu of the jet emanator 52, more specifically designated as a toroidal loop 52a, and the inner body 130. One portion of the jet cap 220 includes a main cylindrical-like body 222 having opposing annular rings 224 and 226 extending from the ends thereof, a guidewire lumen 228 extending through the main body 222, an annular extension 230 extending outwardly from one end of the main body 222 and having an annular surface 232 which lies in the same plane as an annular surface 234 of the annular ring 224, an annulus 236 between one end of the main body 222, the annular ring 224 and the annular extension 230, and an annular extension 238 extending outwardly from and beyond the annular surface 232 of the annular extension 230. Another portion of the jet cap 220 includes a round plate 240 including a central hole 242, a receptor hole 224 for accommodation of a second tube 42 and a plurality of jet orifices 246a–246n aligned concentric to the central hole 242.

Figure 33:
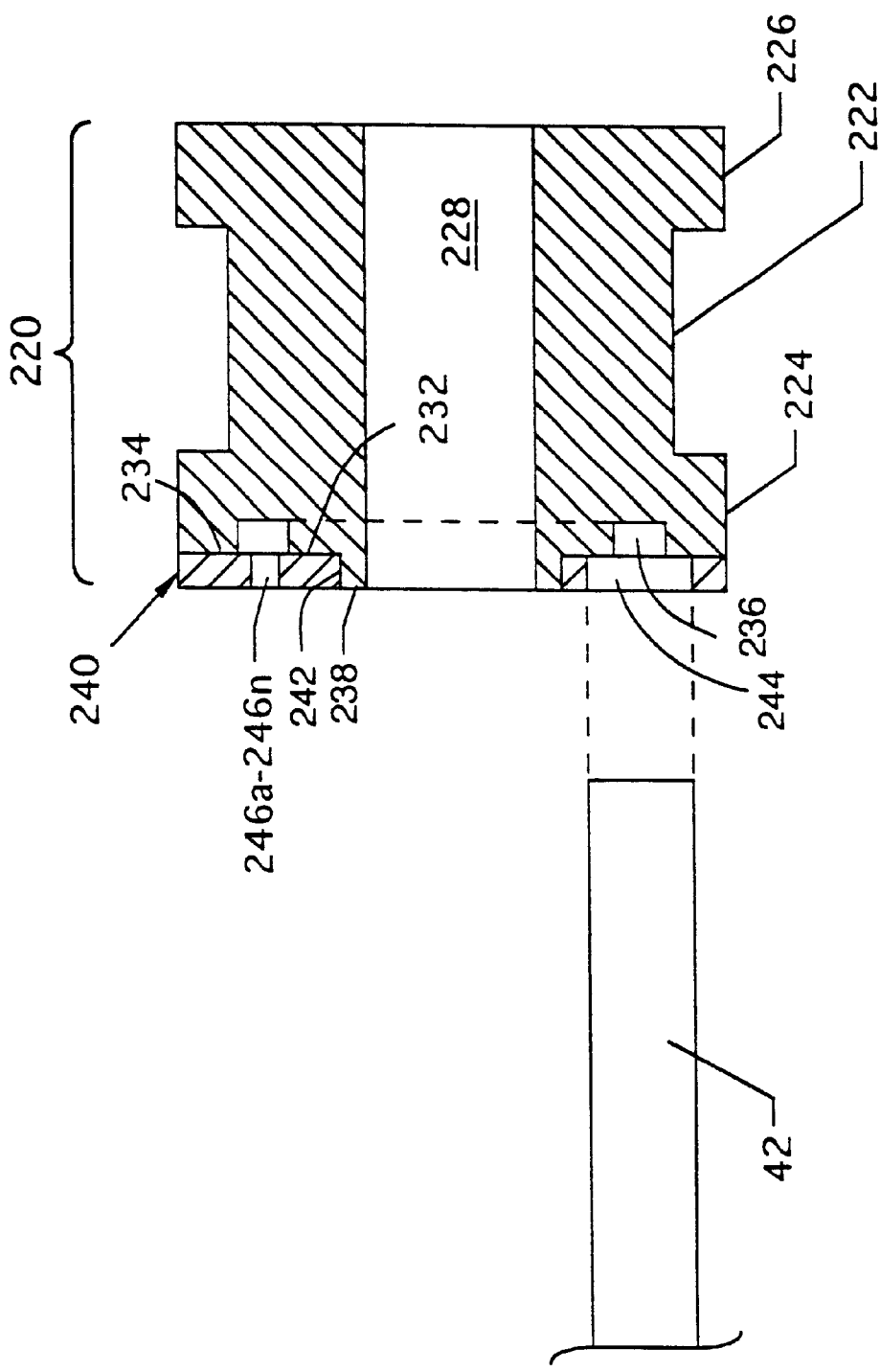
FIG. 33 illustrates a cross section view of the jet cap along line 33—33 of FIG. 32.

FIG. 33 illustrates a cross section view of the jet cap 220 along line 33—33 of FIG. 32, where all numerals correspond to those elements previously described. The central hole 242 of the round plate 240 utilizes the annular extension 238 to align the round plate 240 to the annular surface 232 and the annular surface 234 of the annular ring 224 and is suitably secured thereto. Such close alignment seals to the annulus 236 which forms a circular chamber for the distribution of high pressure saline through the sealed annulus 236. Annular rings 224 and 226 can engage and are fixed in the interior annular surface 64 of an exhaust tube 122. High pressure saline is delivered to the second tube 42, which suitably secures in the receptor hole 244 located on the round plate 240 and as such is distributed through the sealed annulus 236 to emanate high pressure saline jet flow through the rearwardly directed jet orifices 246a–246n.

Figure 34:
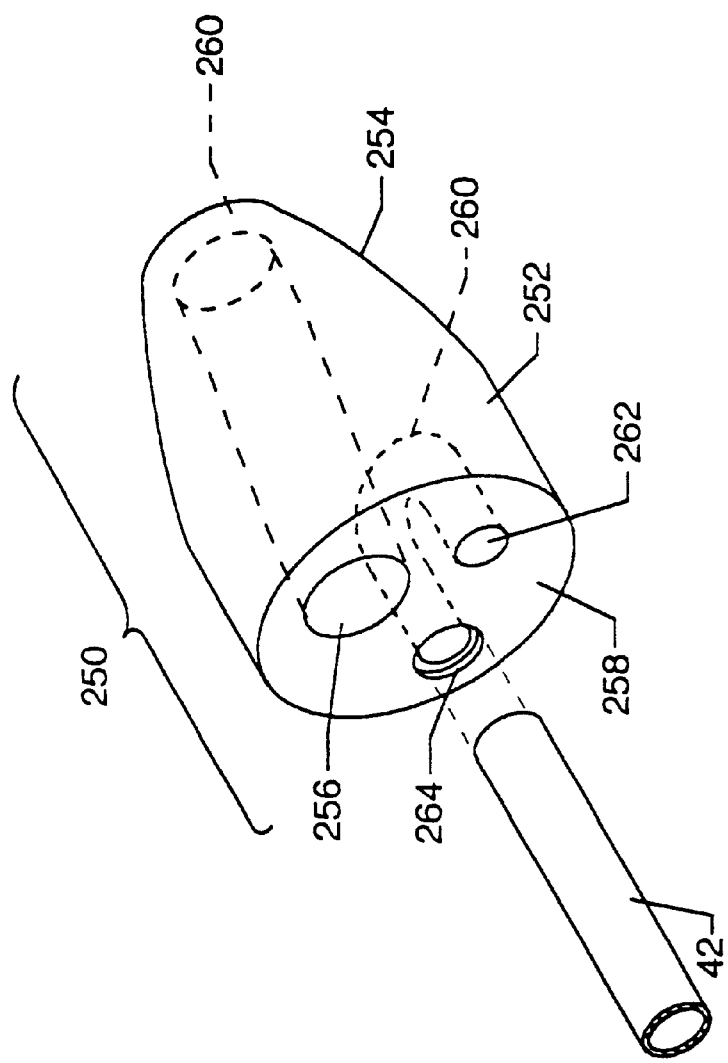
FIG. 34, a tenth alternative embodiment, illustrates an isometric view of a jet cap having formed passages.

FIG. 34, a tenth alternative embodiment, illustrates an isometric jet emanator in the form of a jet cap 250 having formed passages contained therein. The formed passage jet cap 250 has a one-piece body 252 which includes a rounded taper 254 tapering downwardly in the distal direction. A guidewire lumen 256 extends longitudinally through the body 252 extending between a, proximal surface 258 and a distal surface 259. A U-shaped passageway 260, for the conveyance of high pressure saline, is located interior to the body 252 and terminates at one end as a jet orifice 262 at the proximal surface 258 and at a receptor hole 264 for the accommodation of a second tube 42 at the proximal surface 258. In the illustration, a second tube 42 is shown for delivery of high pressure saline to the passageway 260.

Figure 35:
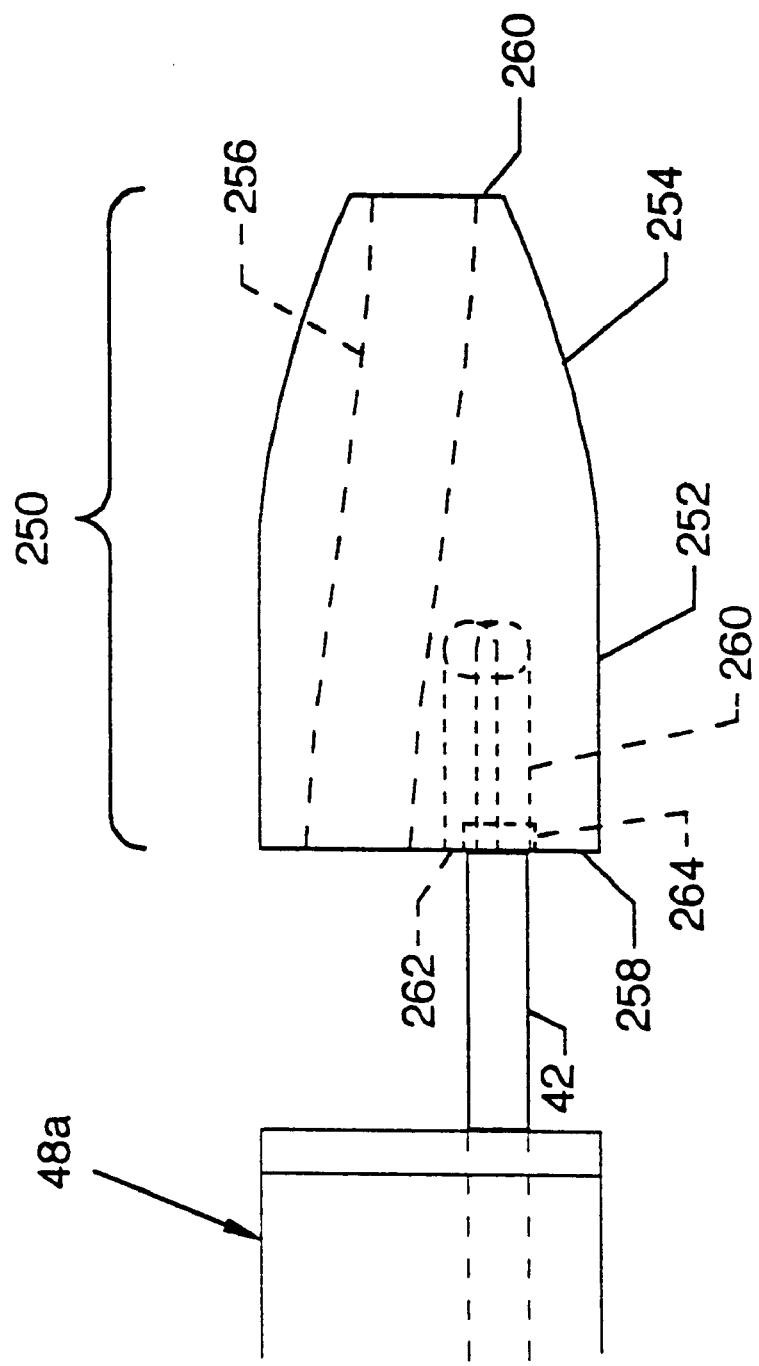
FIG. 35 illustrates a side view of the formed passage jet cap in use as an emanator.

FIG. 35 illustrates a side view of the formed passage jet cap 250 in use as an emanator, such as in use with a flow director 48a of a single operator fluid jet exchange thrombectomy device. The formed passage jet cap 250 can also be incorporated (not illustrated) with additional proximally located structure having inflow and outflow orifices, such as inflow orifice(s) 136 and outflow orifice(s) 134 shown previously, to function with a crossflow/flow director for configuration and use as a single operator jet exchange thrombectomy device having crossflow capabilities.

Figure 36:
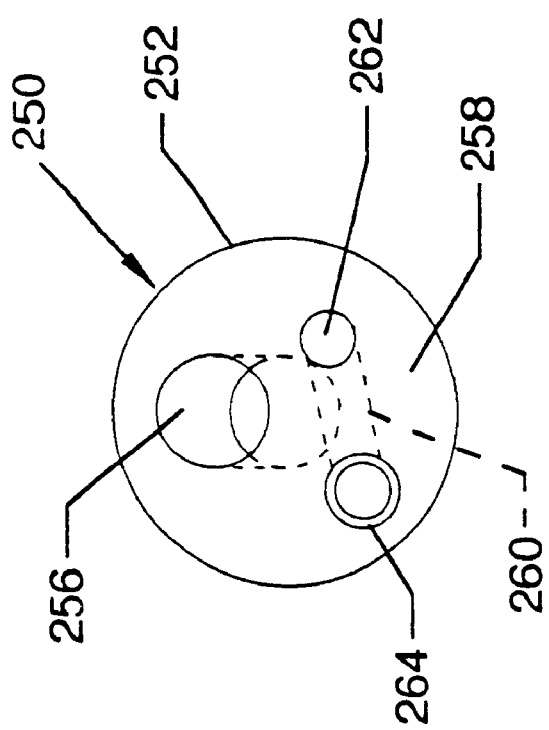
FIG. 36 illustrates a proximal view of the formed passage jet cap.

FIG. 36 illustrates a proximal end view of the formed passage jet cap 250.

Figure 37:
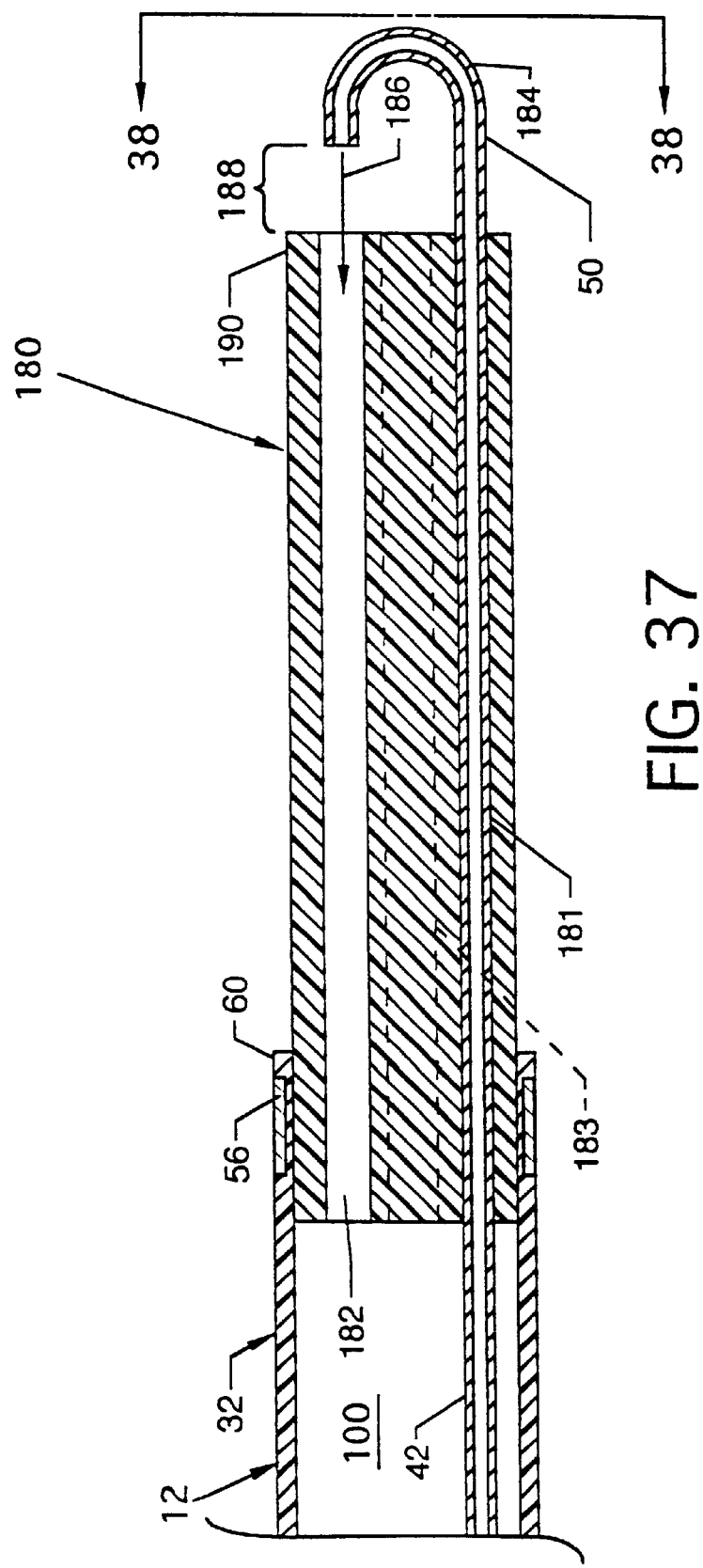
FIG. 37, an eleventh alternative embodiment, illustrates a cross section view of an inner body along line 37—37 of FIG. 38.
Figure 38:
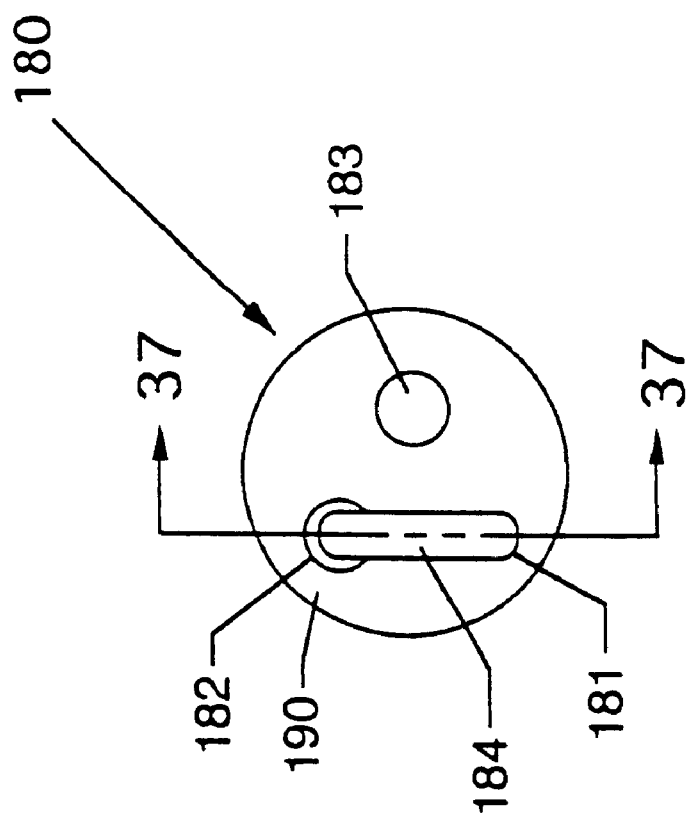
FIG. 38 illustrates an end view of the inner body along line 38—38 of FIG. 37.

FIG. 37, an eleventh alternative embodiment, illustrates a cross section view of an inner body 180 along line 37—37 of FIG. 38, and FIG. 38 illustrates an end view of the inner body 180 along line 38—38 of FIG. 37, which can be substituted at one end of the inner catheter assembly 14. More specifically, the inner body 180 can be substituted for the flow director 48a at the distal end 50 of the second tube 42. The inner body 180, which is cylindrically shaped, can be of plastic or other suitable material and includes a bore 181 for fixed accommodation of the second tube 42 extending longitudinally through the inner body 180 as well as a guidewire passage 183 extending longitudinally through the inner body 180. The inner body 180 also includes a longitudinally aligned exhaust lumen 182 extending through the inner body 180 to communicate with the lumen 100 of the first tube or guide catheter 32. A jet emanator 184, which is curved, extends from the distal end 50 of the second tube 42 and is directed to align and to introduce a high pressure saline jet 186 with the exhaust lumen 182. The high pressure saline jet 186 transits a space 188 between the curved jet emanator 184 and the distal end 190 of inner body 180 to contact and break away thrombotic material or lesions which are subsequently entrained therein to be evacuated via the exhaust lumen 182 and lumen 100 of the first tube or guide catheter 32 of the outer catheter assembly 12.

Figure 39:
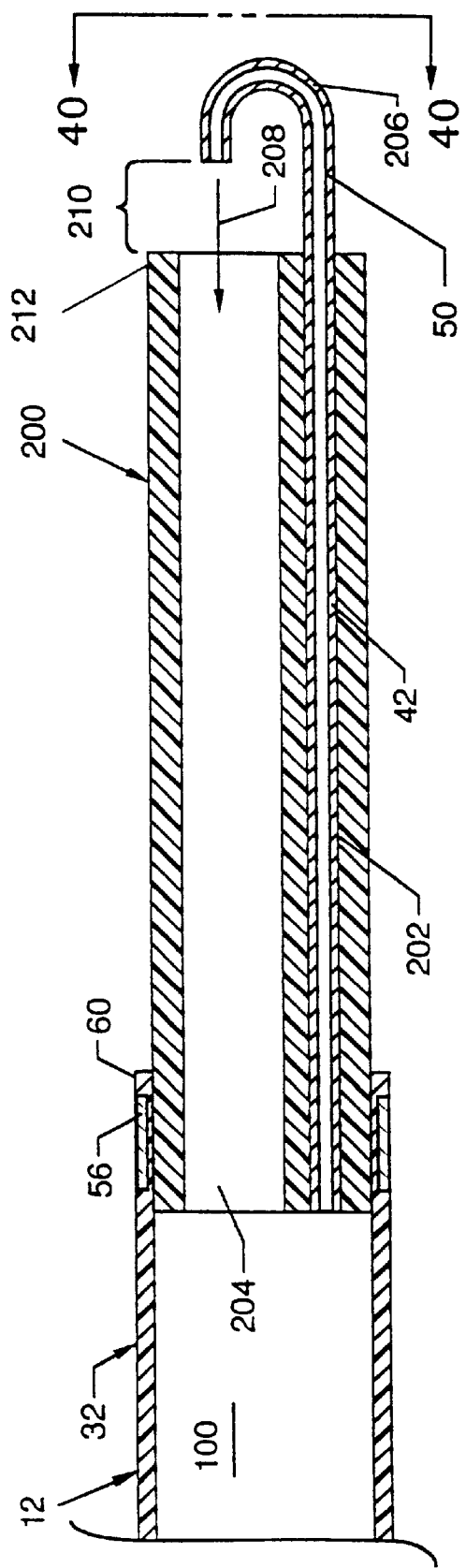
FIG. 39, a twelfth alternative embodiment, illustrates a cross section view of an inner body along line 39—39 of FIG. 40.
Figure 40:
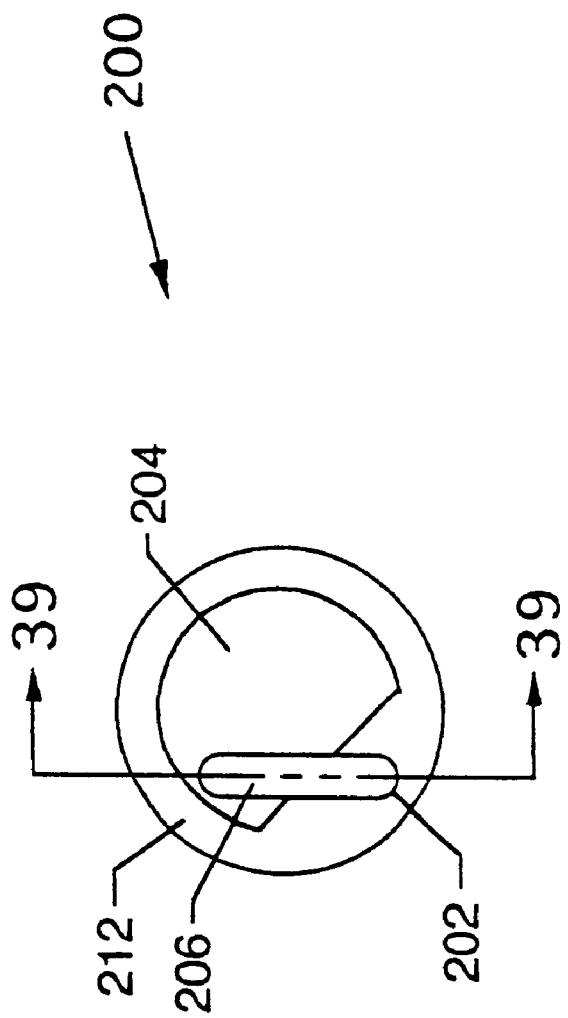
FIG. 40 illustrates an end view of the inner body along line 40—40 of FIG. 39.

FIG. 39, a twelfth alternative embodiment, illustrates a cross section view of an inner body 200 along line 39—39 of FIG. 40, and FIG. 40 illustrates an end view of the inner body 200 along line 40—40 of FIG. 39, which can be substituted at one end of the inner catheter assembly 14. More specifically, the inner body 200 can be substituted for the flow director 48a at the distal end 50 of the second tube 42. The inner body 200, which is cylindrically shaped, can be of plastic or other suitable material and includes a bore 202 for fixed accommodation of the second tube 42 extending longitudinally through the inner body 200, as well as a large multipurpose lumen 204 extending longitudinally through the inner body 200. The multipurpose lumen 204 serves as an exhaust lumen and as a passage for accommodation of a guidewire. The multipurpose lumen 204 communicates with the lumen 100 of the first tube or guide catheter 32. A jet emanator 206, which is curved, and which is offset from the multipurpose lumen 204, extends from the distal end 50 of the second tube 42 and is directed to align and to introduce a high pressure saline jet 208 with the multipurpose lumen 204. The high pressure saline jet 208 transits a space 210 between the curved jet emanator 206 and the distal end 212 of inner body 200 to contact and break away thrombotic material or lesions which are subsequently entrained therein to be evacuated via the multi-purpose lumen 204 and lumen 100 of the first tube or guide catheter 32 of the outer catheter assembly 12.

Figure 41:
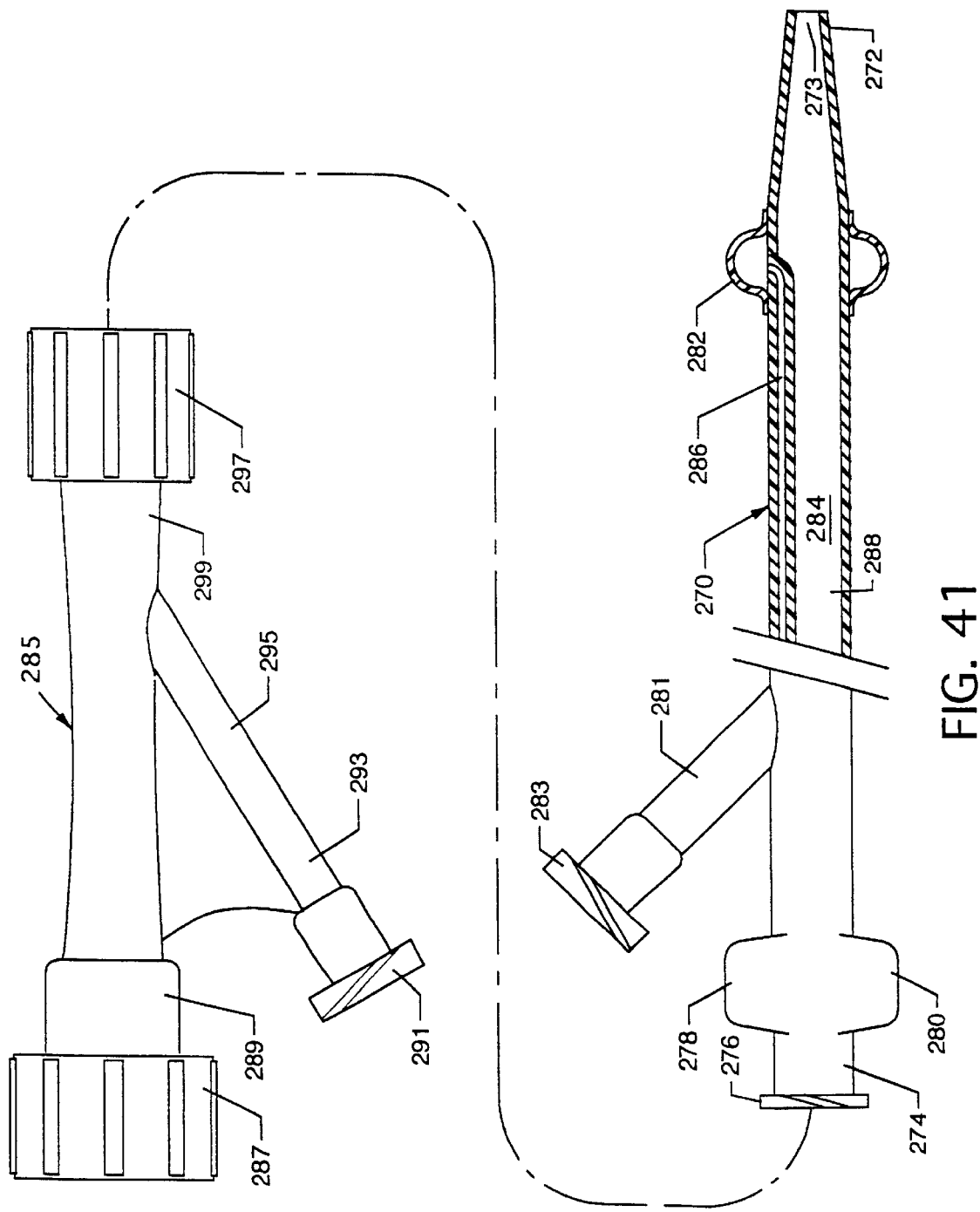
FIG. 41, a thirteenth alternative embodiment, illustrates a cross section view of a first tube or guide catheter having a distally located inflatable balloon.

FIG. 41, a thirteenth alternative embodiment, illustrates a side view of a manifold 285 and a view in partial cross section of a first tube or guide catheter 270 which can be incorporated substantially in lieu of and resembling for the most a first tube or guide catheter 32, previously illustrated, including a distal end 272 which is tapered, a passage 273 for a guidewire, a proximal end 274, a Luer connection 276, manipulating tabs 278 and 280, a manifold branch 281 extending from the first tube or guide catheter 270 and a Luer connector 283 at the end of the manifold branch 281, and other members as now described. The first tube or guide catheter 270 includes an inflatable balloon 282, shown in the inflated mode, which is suitably secured to and which is located about one end of and near the distal end 272 of the tubular structure. A lumen 284 for effluent evacuation extends along the interior of the first tube or guide catheter 270. An inflation lumen 286 partially utilizing the interior wall 288 extends partially along the length of the lumen 284 and connects with the manifold branch 281 and Luer connector 283 to communicate with and for inflation of the balloon 282. Manifold 285, similar to manifold 20 of FIG. 2, is provided including a hemostasis nut/stop 287 secured in the proximal end 289 of the manifold 285, a Luer connection 291 located at the proximal end 293 of an angled manifold branch 295 extending from the manifold 285 and a Luer fitting 297 at the distal end 299 of the manifold 285.

Figure 42:
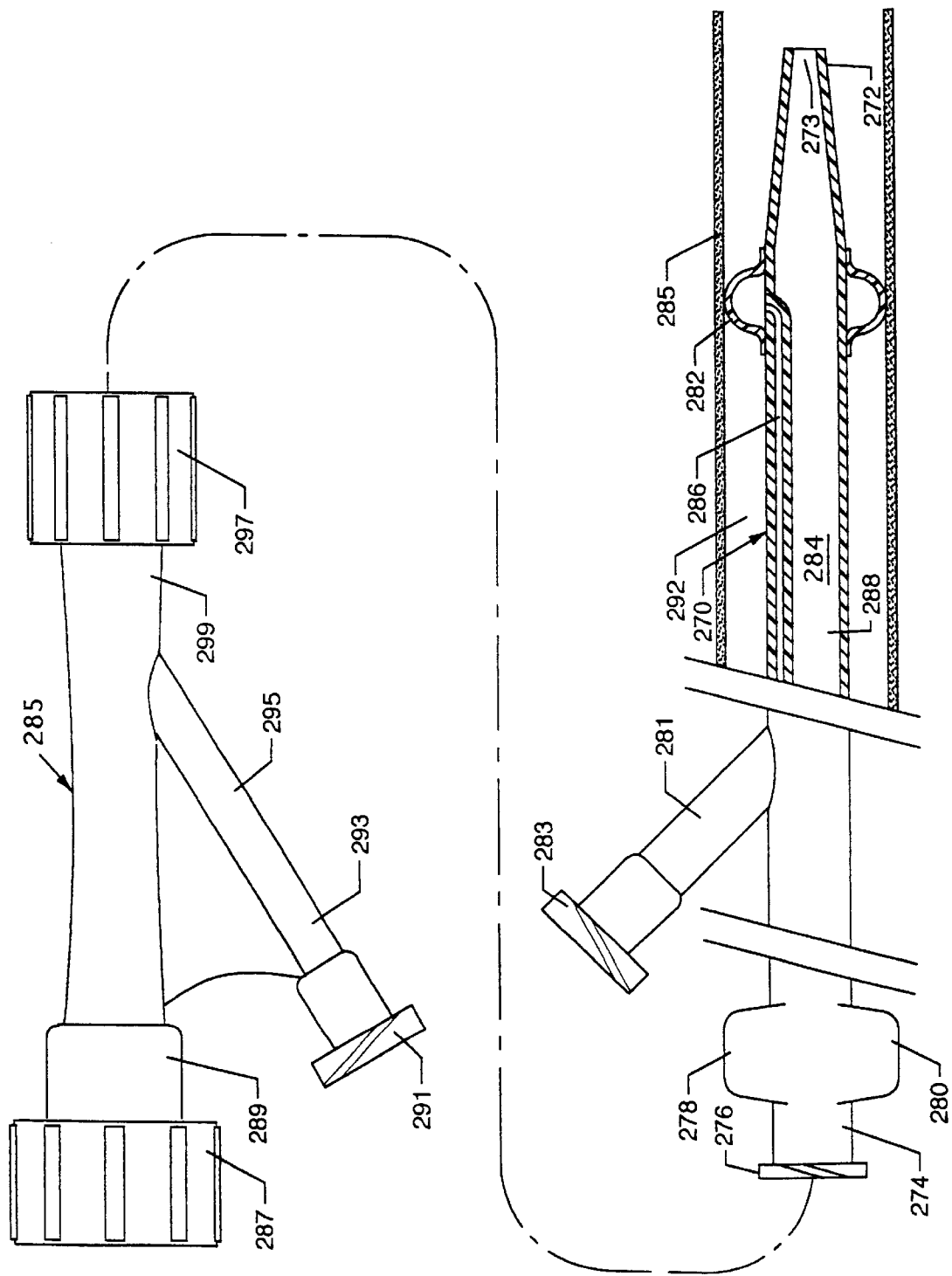
FIG. 42 illustrates the first tube or guide catheter of FIG. 41 in use in a blood vessel.

FIG. 42 illustrates the first tube or guide catheter 270 in use in a blood vessel 275. The inflatable balloon 282 which inflates to contact and seal against the blood vessel 275 provides for a region of proximal occlusion 292 with respect to the location of the inflated balloon 282, that region extending proximally from the inflated balloon 282 between the first tube or guide catheter 270 and the blood vessel 275. Such a region of proximal occlusion 292 prevents thrombotic deposits or lesions from traveling proximally along and about the exterior of the first tube or guide catheter 270 and the interior of the blood vessel 275 and ensures removal of the thrombotic deposits or lesions along and through the lumen 284. Cessation of flow also minimizes the possibility of distal embolization of thrombotic debris. Inflation of the balloon 282 provides for centering of the first tube or guide catheter 270 and a suitable jet emanator within the blood vessel 275 to provide for centrally located and evenly applied saline emanation which can also preclude having the jetted saline emitted dangerously close to the wall of the blood vessel 275. Such centering allows for more powerful suction without damage to the blood vessel wall.

Figure 43:
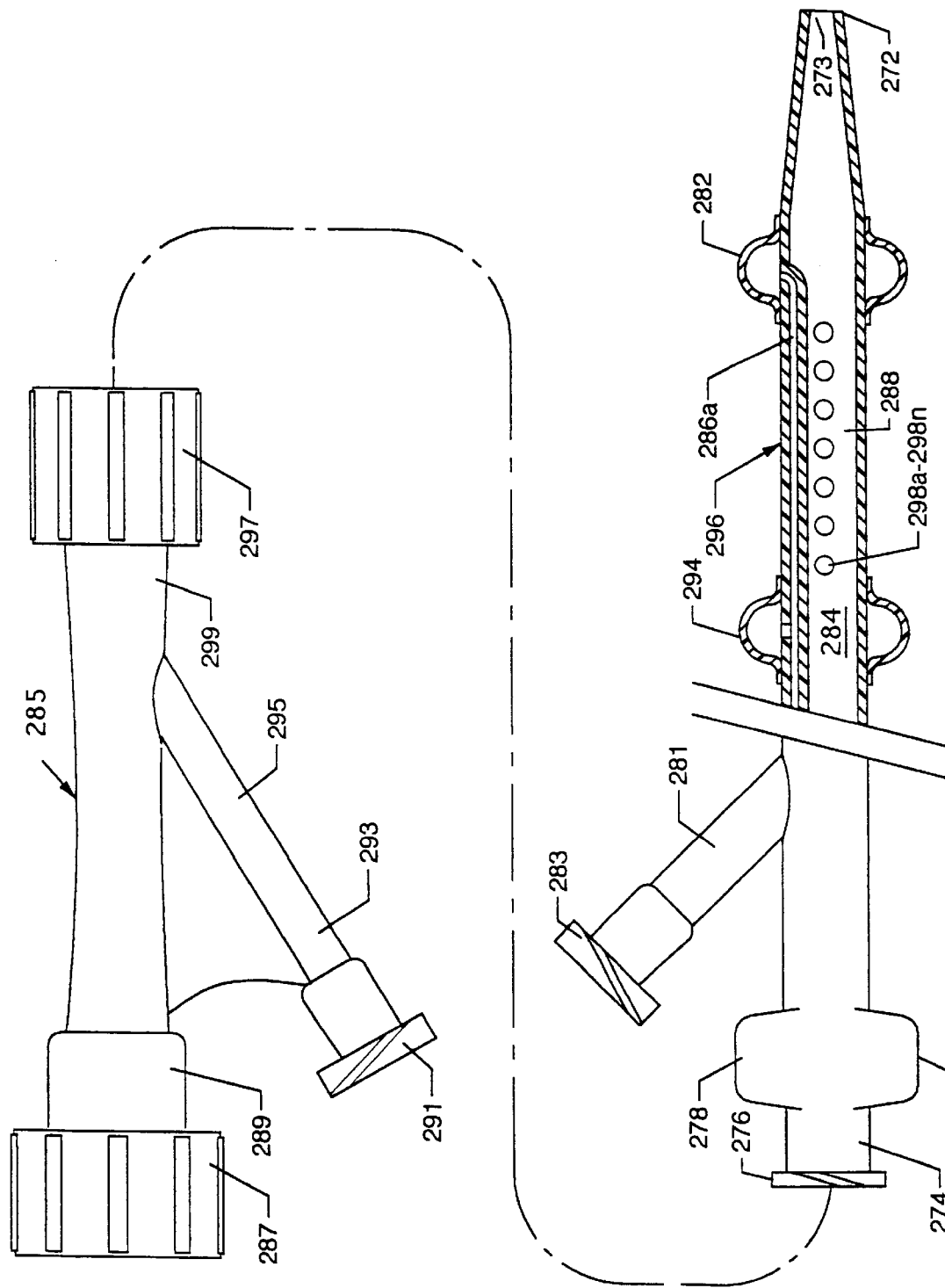
FIG. 43, a fourteenth alternative embodiment, illustrates a cross section view of a first tube or guide catheter having a distally located inflatable balloon and another inflatable balloon located proximal to the distally located inflatable balloon.

FIG. 43, a fourteenth alternative embodiment, includes the components and members described in FIG. 41, including an additional inflatable balloon 294 located proximal to the inflatable balloon 282 to provide a first tube or guide catheter 296 which can be incorporated substantially in lieu of and resembling for the most a first tube or guide catheter 32, previously illustrated, including a distal end 272 which is tapered, a passage 273 for a guidewire, a proximal end 274, a Luer connection 276, manipulating tabs 278 and 280, a manifold branch 281 extending from the first tube or guide catheter 270 and a Luer connector 283 at the end of the manifold branch 281, and other members as now described. The first tube or guide catheter 296 includes inflatable balloons 282 and 294 shown in the inflated mode, which are suitably secured to and one of which, inflatable balloon 282, is located about one end of and near the distal end 272 of the tubular structure and the other inflatable balloon 294 is located proximally and opposingly with respect to the inflatable balloon 282 on the tubular structure. A lumen 284 for effluent evacuation extends along the interior of the first tube or guide catheter 296. An inflation lumen 286a partially utilizing the interior wall 288 extends the length of the lumen 284 and connects with the manifold branch 281 and the Luer connector 283 to communicate with and for inflation of the balloons 282 and 294. A plurality of inflow orifices 298a–298n are included in the tubular structure to provide for suction of thrombus or other effluent through a flow director 300, shown representatively in dashed lines in FIG. 44.

Figure 44:
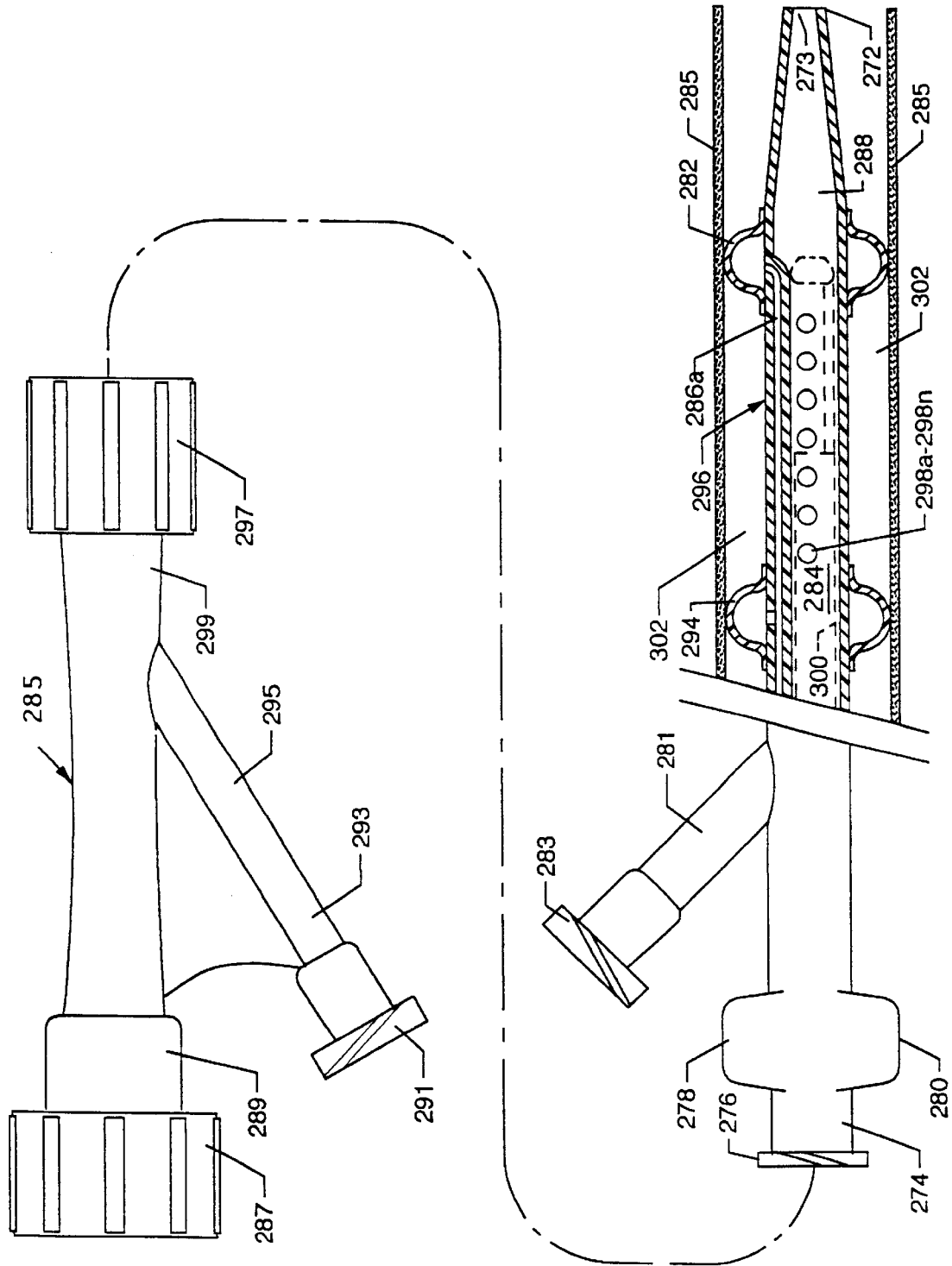
FIG. 44 illustrates the first tube or guide catheter of FIG. 43 in use in a blood vessel.

FIG. 44 illustrates the first tube or guide catheter 296 in use in a blood vessel 275. The inflatable balloons 282 and 294 which are inflated to contact and seal against the blood vessel 275 provide for a sealed region 302 extending proximally from the inflated balloon 282 and distally from the inflated balloon 294, between the first tube or guide catheter 296 and the blood vessel 275. Such a sealed region 302 of occlusion contains thrombotic deposits or lesions about the exterior of the first tube or guide catheter 296 and between the inflatable balloon 282 and 294 and ensures removal of the thrombotic deposits or lesions through the flow director 300, the position of which can be varied longitudinally. Such an arrangement is also helpful in preventing proximal and distal embolizations. Inflation of the inflatable balloons 282 and 294 provides for centering of the first tube or guide catheter 296 within the blood vessel 275 to provide for centrally located and evenly applied saline emanation which can also preclude having the jetted saline emitted dangerously close to the wall of the blood vessel 275. Such centering allows for more powerful suction without damage to the wall of the blood vessel 275.

Figure 45:
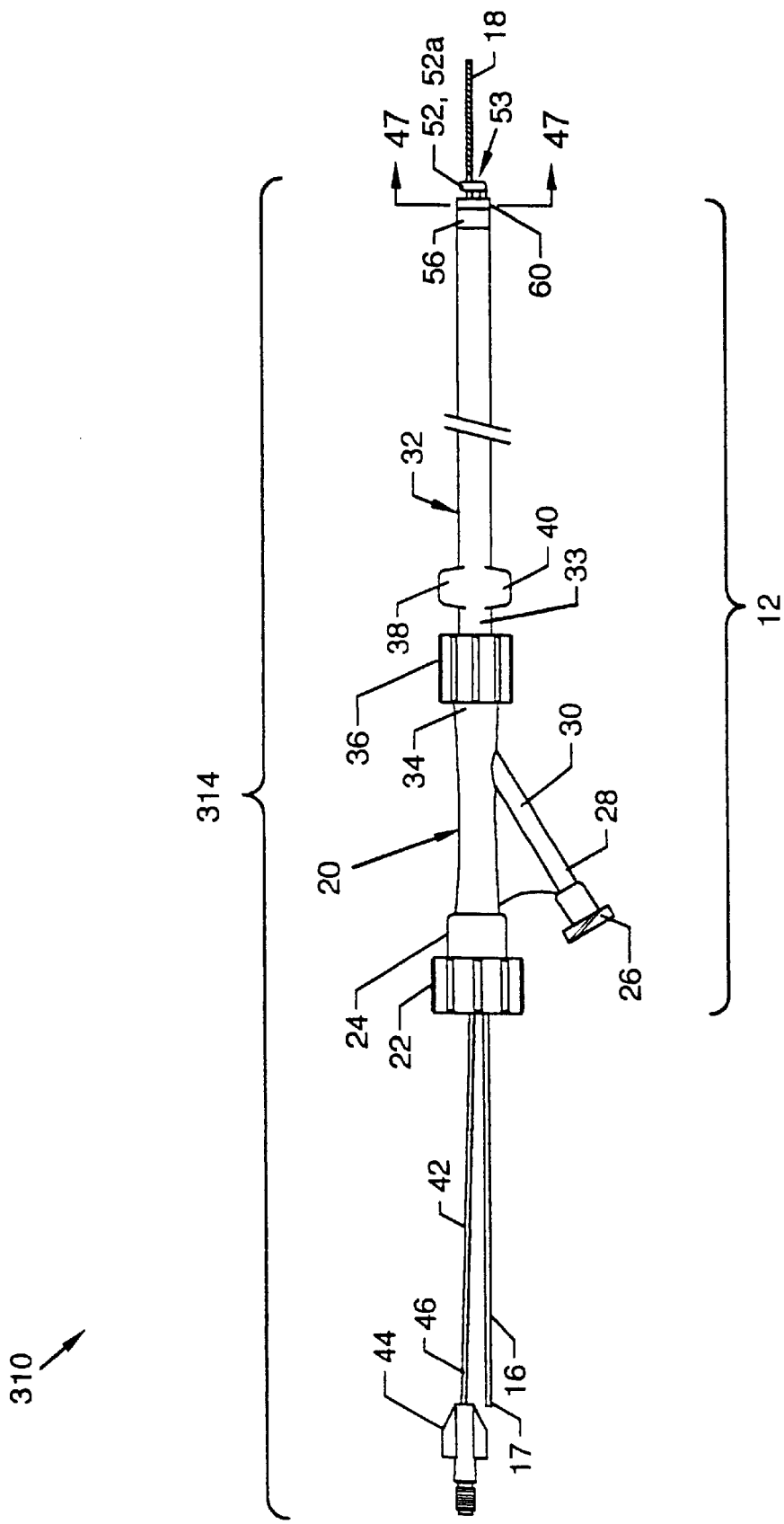
FIG. 45, a fifteenth alternative embodiment, illustrates a side view of a single operator exchange fluid jet thrombectomy device.
Figure 46:
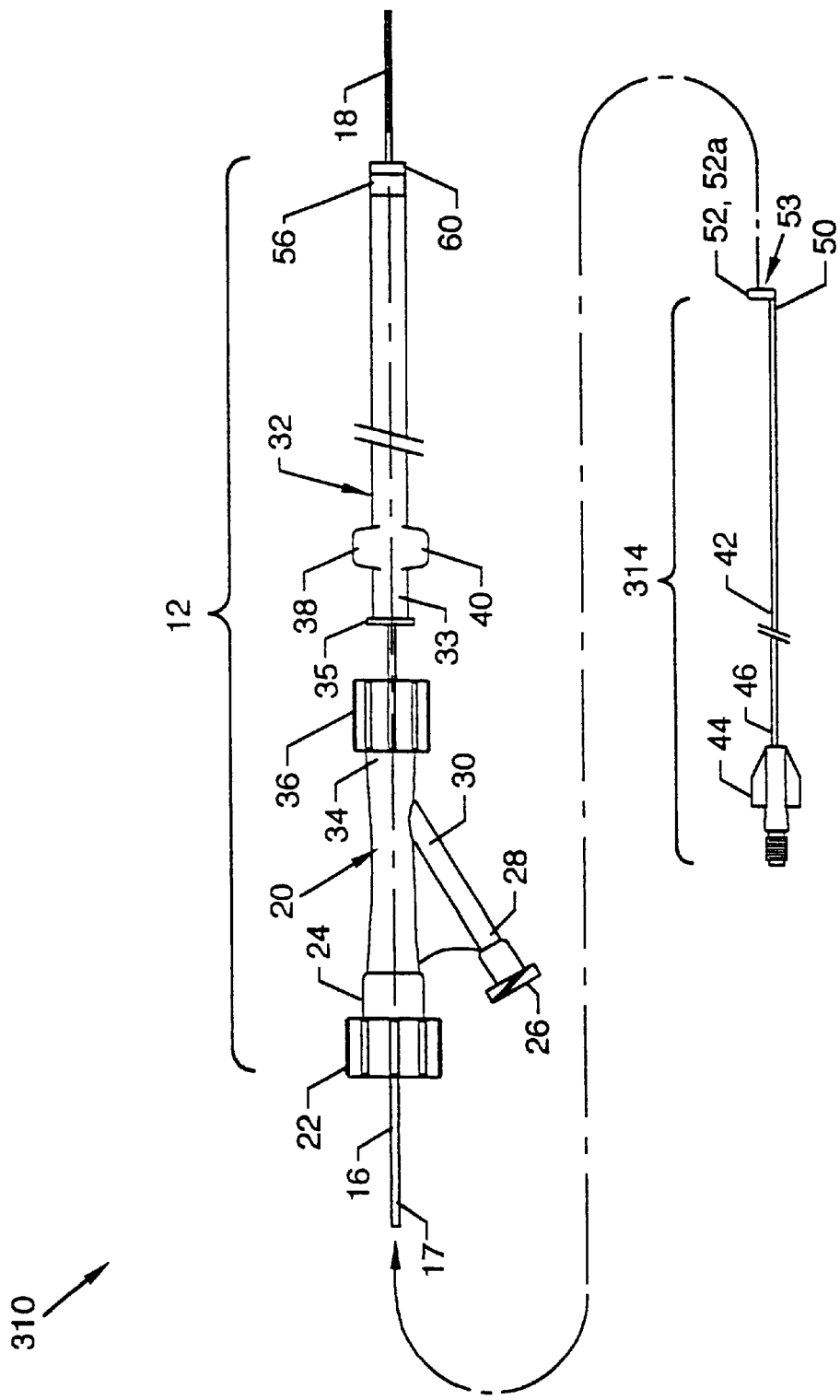
FIG. 46 illustrates a semi-exploded side view of the single operator exchange fluid jet thrombectomy device of FIG. 45.

FIG. 45, a fifteenth alternative embodiment, illustrates a side view of a single operator exchange fluid jet thrombectomy device 310 which can be incorporated for the removal of thrombus, and FIG. 46 illustrates a semi-exploded side view of the single operator exchange fluid jet thrombectomy device 310. The single operator exchange fluid jet thrombectomy device 310 includes two major assemblies: namely, an outer catheter assembly 12, as previously described in detail and which is a core assembly, and an inner catheter assembly 314 configured to function as a thrombectomy catheter, which has been substituted or exchanged for the previously described inner catheter assembly 14 and which is shown as an example of inner catheter assemblies which can be exchanged with other styles or designs of inner catheter assemblies as desired to fit substantially within and to be incorporated with the outer catheter assembly 12. The inner catheter assembly 314, when in use, aligns mostly within the outer catheter assembly 12 and extends beyond both ends of the outer catheter assembly 12, although the amount extending beyond both ends is not necessarily illustrated proportionally. Both the outer catheter assembly 12 and the inner catheter assembly 314 align over and about the guidewire 16 which includes a flexible tip 18 at one end and a proximal end 17 opposing the flexible tip 18. Externally visible components, or portions of components, of the outer catheter assembly 12 correspond to the previous descriptions. Much of the structure of the previously described inner catheter assembly 14 is incorporated and utilized in the inner catheter assembly 314. Externally visible components or portions of components of the inner catheter assembly 314 of the single operator exchange fluid jet thrombectomy device 310 include the high pressure second tube 42, the transitional filter housing/high pressure connection/stop assembly 44 concentrically aligned to and secured over and about the proximal end 46 of the second tube 42, and a jet emanator 52 consisting of a toroidal loop 52a having a passage 53 (FIG. 22) at the distal end 50 of the second tube 42. Optionally, a jet cap, such as jet cap 54 of FIG. 2, can be included over and about the jet emanator 52 consisting of a toroidal loop 52a. The inner catheter assembly 314 is 10 deployed within the outer catheter assembly 12 and is positioned to place the jet emanator 52 distal to the distal end 60 of the first tube or guide catheter 32 by a distance of 0.005 inch to 0.500 inch depending on the type of anatomy and material to be removed.

Figure 47:
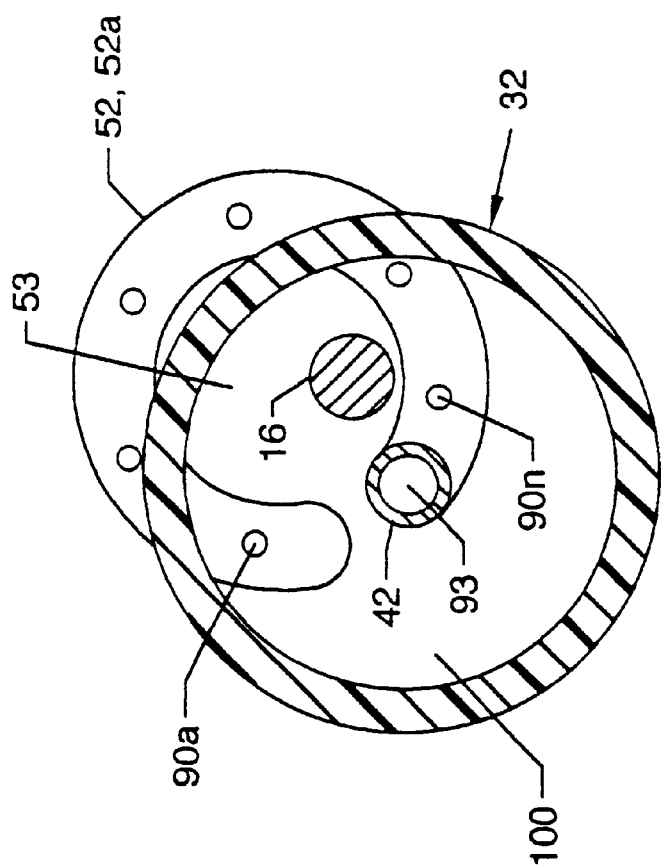
FIG. 47 illustrates a cross section view along line 47—47 of FIG. 45 of the single operator exchange fluid jet thrombectomy device.

FIG. 47 illustrates a cross sectional view along line 47—47 of FIG. 45 of the single operator exchange fluid jet thrombectomy device 310 looking distally. The alignment of the jet emanator 52, in this case, a toroidal loop 52a, is such that saline jet flow 96 emanating from at least one of the jet orifices 90a–90n will impinge the lumen 100 of the first tube or guide catheter 32 to provide stagnation pressure for effluent evacuation. Other streams of saline jet flow 96 emanating from the jet orifices 90a–90n may not impinge the lumen 100, as the device can be tailored and configured for particular anatomy and material to be removed to prevent undesirable damage from these jets. The saline jet flow emanating from the jet orifices 90a–90n creates suction and maceration forces at the distal end 60 of the first tube or guide catheter 32 for removal of undesirable material.

Figure 48:
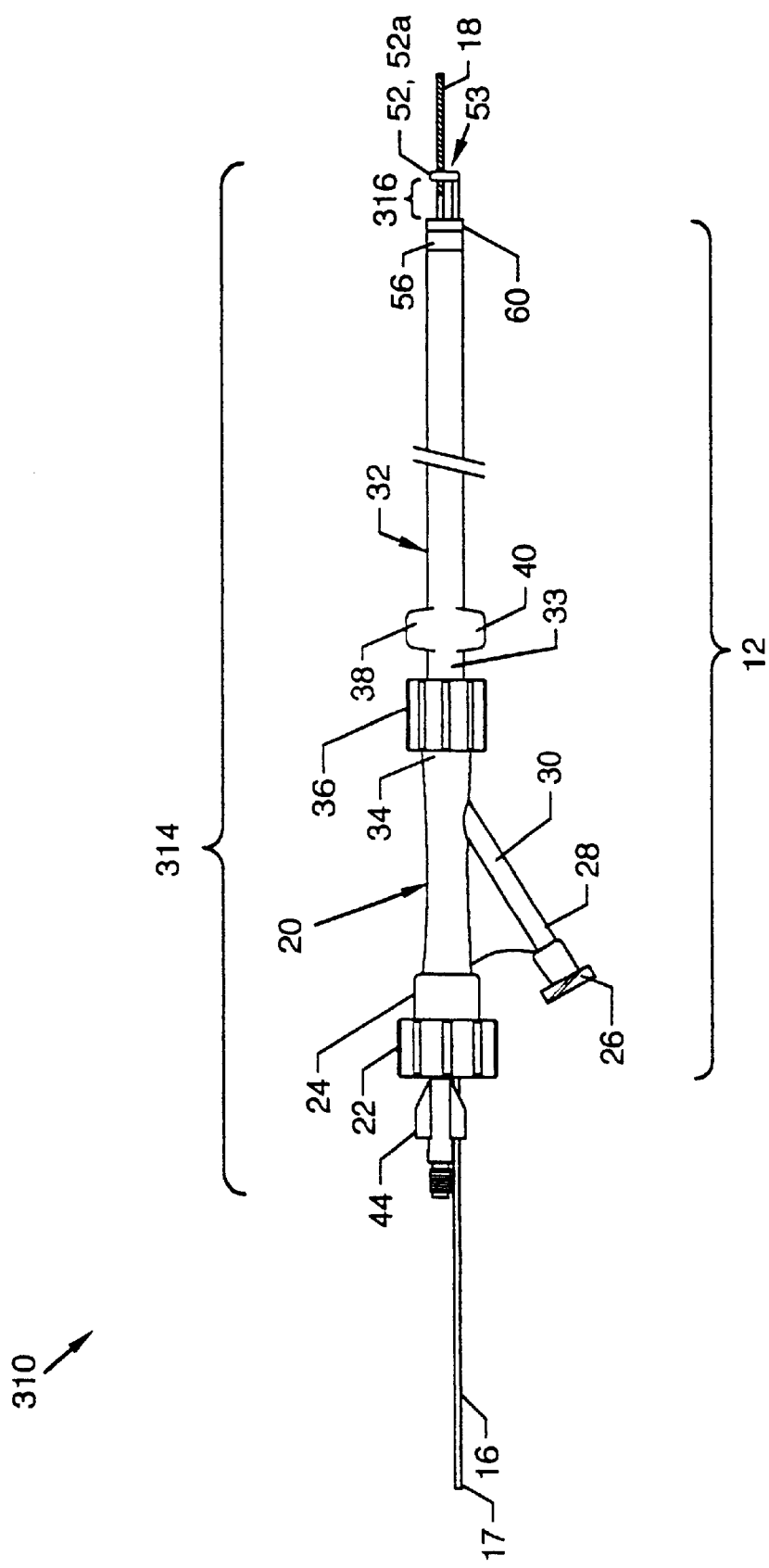
FIG. 48 illustrates the elements of FIG. 45 having a second tube of a predetermined length to limit the distance a jet emanator can travel beyond the distal end of the first tube or guide catheter.

FIG. 48 illustrates the elements of FIG. 45 where the length of the second tube 42 is of a predetermined length, whereby the transitional filter housing/high pressure connection/stop assembly 44 impinges the hemostasis nut/stop 22 to limit the distance the jet emanator 52, in this case a toroidal loop 52a, can extend distally beyond the distal end 60 of the first tube or guide catheter 32 to prevent emanation of saline jet flow from one or more of the jet orifices 90a–90n from not impinging the lumen 100 of the first tube or guide catheter 32 in order to provide a maximum safe gap 316, the distance between the jet emanator 52 and distal end 60 of the first tube or guide catheter 32, in order to avoid undesirable damage to a vessel wall.

Figure 49:
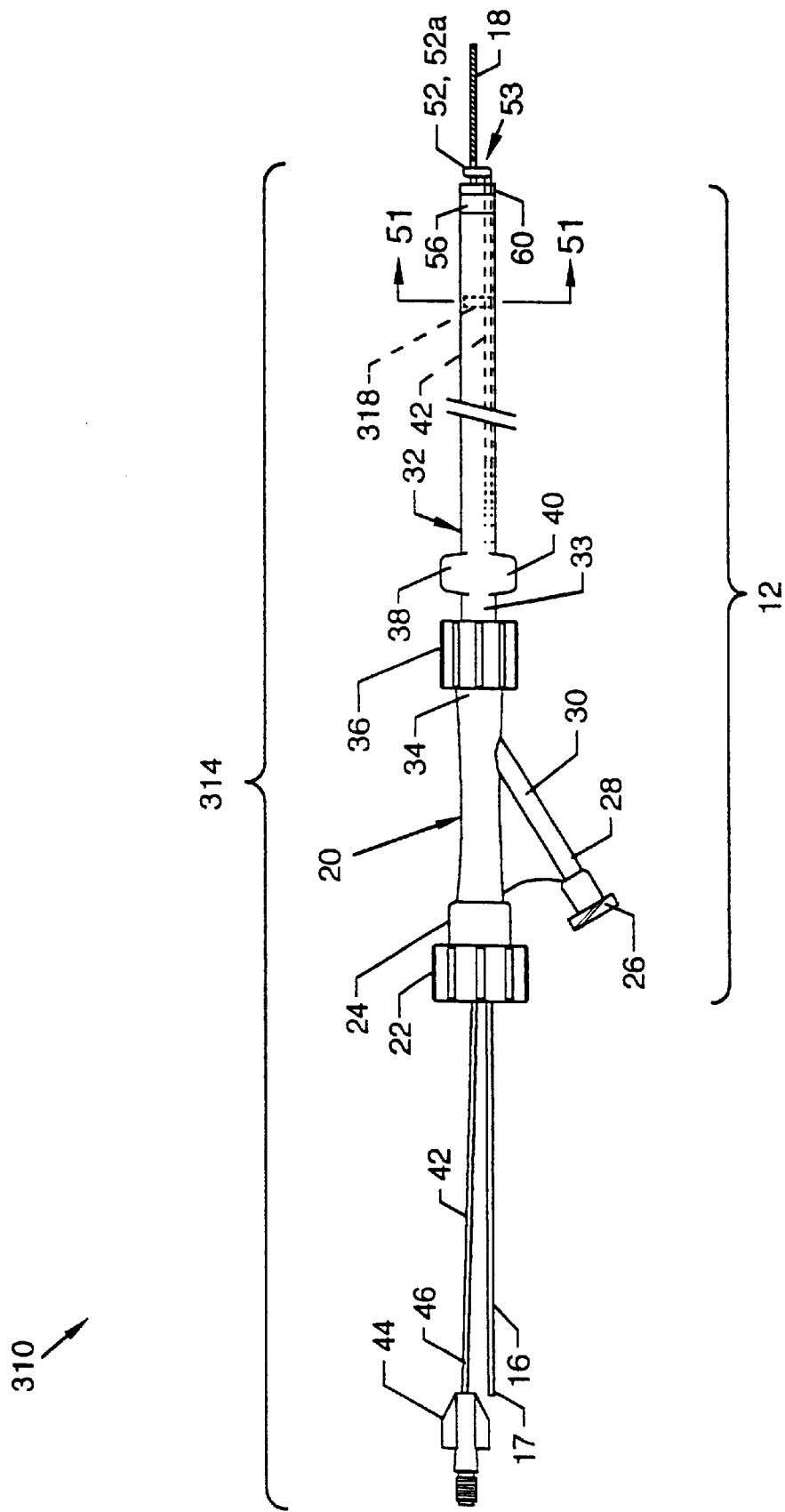
FIG. 49 illustrates the use of a centering ring with the elements of FIGS. 45, 46, 47 and 48.
Figure 50:
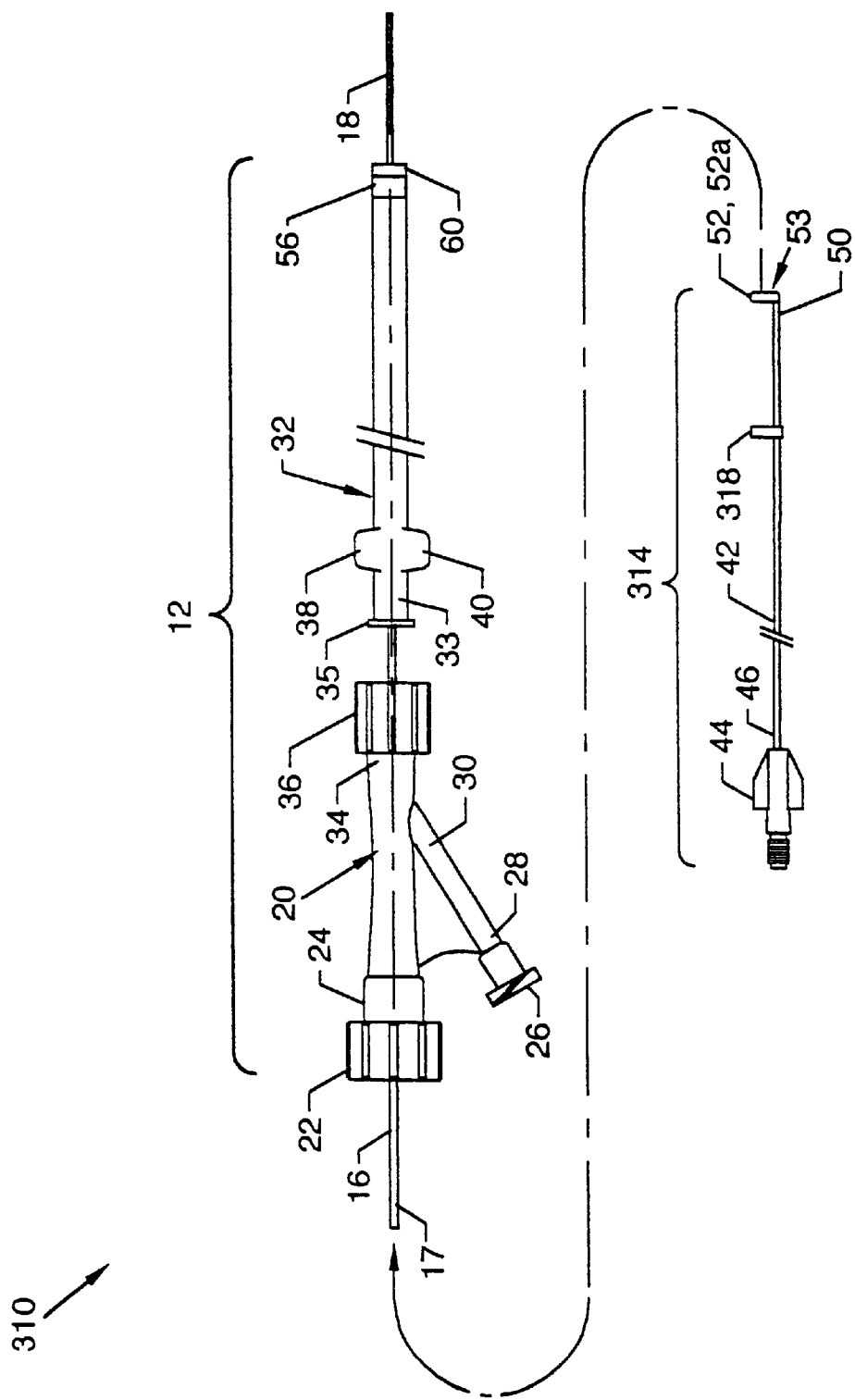
FIG. 50 illustrates a semi-exploded side view of the elements of FIG. 49.

FIG. 49 illustrates a side view, and FIG. 50 illustrates a semi-exploded side view, of the elements and features of FIGS. 45, 46, 47 and 48 additionally including a centering ring 318 secured to the second tube 42 slightly proximal to the jet emanator 52. The centering ring 318 is placed such that it remains housed within the first tube or guide catheter 32 to ensure coaxial positioning of the centering ring 318 within the first tube or guide catheter 32. Such coaxial positioning ensures impingement of the saline jet flow emanating from the jet orifices 90a–90n with the lumen 100 of the first tube or guide catheter 32 and as such avoids having saline jet flow which does not impinge the lumen 100 of the first tube or guide catheter 32.

Figure 51:
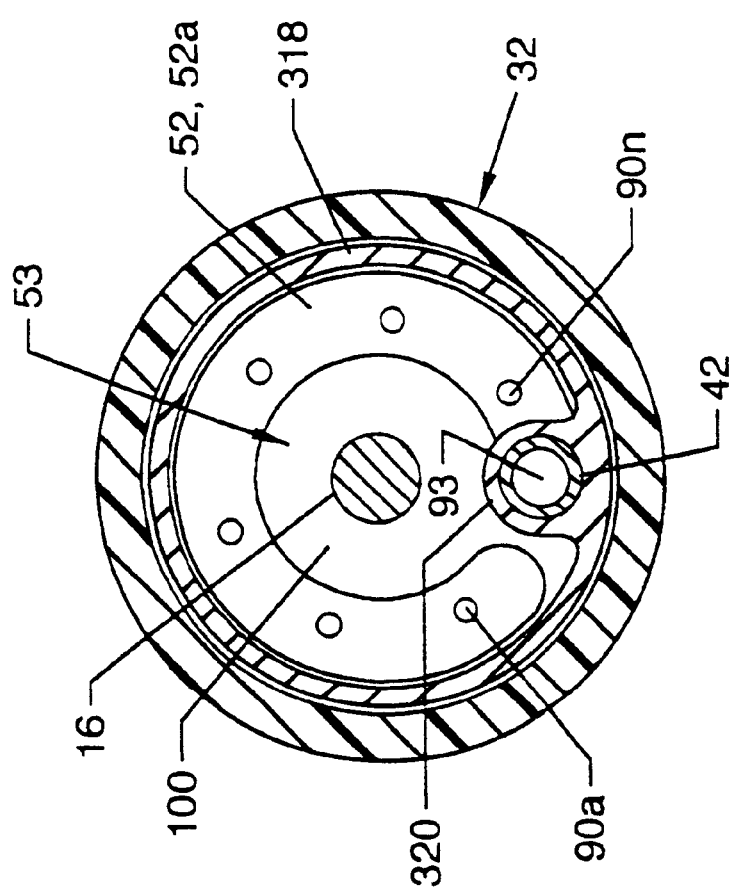
FIG. 51 illustrates a cross section view of the single operator exchange fluid jet thrombectomy device along line 51—51 of FIG. 49.

FIG. 51 illustrates a cross section view of the single operator exchange fluid jet thrombectomy device 310 along line 51—51 of FIG. 49, wherein the centering ring 318 is utilized. The centering ring 318 is sized to allow longitudinal movement within and along the lumen 100 of the first tube or guide catheter 32. A centering ring surround 320 extends inwardly from the centering ring 318 to surround and firmly attach to the second tube 42. Such firm attachment maintains the aligned relationship of the jet emanator 52, in this case a toroidal loop 52a, with the second tube 42. The aligned relationship, of course, is maintained as the second tube 42 is advanced to position the jet emanator 52 the desired distance beyond the distal end 60 of the first tube or guide catheter 32 to ensure alignment of all of the jet orifices 90a–90n with the lumen 100 at the distal end 60.

Various modifications can be made to the present invention without departing from the apparent scope hereof.

PARTS LIST

| | |
|---|---|
| 10 | single operator exchange fluid jet thrombectomy device |
| 12 | outer catheter assembly |
| 14 | inner catheter assembly |
| 16 | guidewire |
| 17 | proximal end (of guidewire) |
| 18 | flexible tip |
| 20 | manifold |
| 22 | hemostasis nut/stop |
| 24 | proximal end (of manifold) |
| 26 | Luer connection |
| 28 | proximal end (of manifold branch) |
| 30 | manifold branch |
| 32 | first tube or guide catheter |
| 33 | proximal end (of first tube or guide catheter) |
| 34 | distal end (of manifold) |
| 35 | Luer connection |
| 36 | Luer fitting |
| 38 | manipulating tab |
| 40 | manipulating tab |
| 42 | second tube |
| 44 | transitional filter housing/high pressure connection/stop assembly |
| 46 | proximal end (of second tube) |
| 48a–d | optional flow directors |
| 50 | distal end (of second tube) |
| 52 | jet emanator |
| 52a | toroidal loop |
| 53 | passage |
| 54 | jet cap |
| 55 | passage |
| 56 | radio-opaque marker (at distal end of first tube or guide catheter) |
| 57 | distal end (of expandable exhaust tube) |
| 58 | radio-opaque marker (at distal end of expandable exhaust tube) |
| 59 | radio-opaque marker (at proximal end of expandable exhaust tube) |
| 60 | distal end (of first tube or guide catheter) |
| 62 | distal end (of inner catheter assembly) |
| 63 | proximal end (of expandable exhaust tube) |
| 64 | interior annular surface |
| 66 | inner body |
| 68 | annulus |
| 70a | outer annular surface |
| 70b | outer surface |
| 72 | exhaust tube |

-continued

PARTS LIST

| | |
|---|---|
| 72a | compliant expandable exhaust tube |
| 72b | non-compliant expandable exhaust tube |
| 72c | non-expandable, non-compliant close fit exhaust tube |
| 72d | compliant/non-compliant exhaust tube |
| 74 | reduced radius neck |
| 76 | annular barb |
| 78 | interior annular surface |
| 80 | slotted cutout |
| 81 | weld |
| 82 | passage |
| 83 | weld |
| 84 | ramped annular surface |
| 86 | variable displacement distance |
| 88 | space |
| 90a–n | jet orifices |
| 92 | capturing cavity |
| 93 | high pressure lumen |
| 94 | saline |
| 96 | saline jet flow |
| 98 | lumen (of expandable exhaust tube) |
| 100 | lumen (of first tube or guide catheter) |
| 102a–b | segments |
| 104 | blood vessel |
| 106 | thrombotic deposit or lesion |
| 110 | single operator exchange fluid jet thrombectomy device |
| 114 | inner catheter assembly |
| 116a–d | crossflow/flow directors |
| 117 | flexible tapered tip |
| 118 | radio-opaque marker (at distal end of crossflow/flow director) |
| 119 | passage |
| 120 | distal end (of crossflow/flow director) |
| 122 | exhaust tube |
| 122a | compliant expandable exhaust tube |
| 122b | non-compliant expandable exhaust tube |
| 122c | non-expandable, non-compliant close fit exhaust tube |
| 122d | compliant/non-compliant exhaust tube |
| 124 | distal end (of inner catheter assembly) |
| 126 | radio-opaque marker (at proximal end of crossflow/flow director) |
| 127 | radio-opaque marker |
| 128 | proximal end (of crossflow/flow director) |
| 130 | inner body |
| 134 | outflow orifice |
| 136 | inflow orifice |
| 138 | annulus |
| 140 | outer annular surface |
| 142 | reduced radius neck |
| 144 | shoulder |
| 146 | passage |
| 148 | variable displacement distance |
| 150 | saline |
| 152 | saline jet flow |
| 154 | lumen (of crossflow/flow director) |
| 156 | blood vessel |
| 158 | thrombotic deposit or lesion |
| 160 | crossflow jet(s) |
| 170 | outflow orifice(s) |
| 172 | crossflow jet |
| 180 | inner body |
| 181 | bore |
| 182 | exhaust lumen |
| 183 | guidewire passage |
| 184 | curved jet emanator |
| 186 | saline jet |
| 188 | space |
| 190 | distal end (of inner body 180) |
| 200 | inner body |
| 202 | bore |
| 204 | multi-purpose lumen |
| 206 | curved jet emanator |
| 208 | saline jet |
| 210 | space |
| 212 | distal end (of inner body 200) |

-continued

PARTS LIST

| | |
|---|---|
| 214a–b | segments |
| 220 | jet cap |
| 222 | main body |
| 224 | annular ring |
| 226 | annular ring |
| 228 | guidewire lumen |
| 230 | annular extension |
| 232 | annular surface |
| 234 | annular surface |
| 236 | annulus |
| 238 | annular extension |
| 240 | round plate |
| 242 | central hole |
| 244 | receptor hole |
| 246a–n | jet orifices |
| 250 | formed passage jet cap |
| 252 | body |
| 254 | rounded taper |
| 256 | guidewire lumen |
| 258 | proximal surface |
| 259 | distal surface |
| 260 | passageway |
| 262 | jet orifice |
| 264 | receptor hole |
| 270 | first tube or guide catheter |
| 272 | distal end |
| 273 | passage |
| 274 | proximal end |
| 275 | blood vessel |
| 276 | Luer connection |
| 278 | manipulating tab |
| 280 | manipulating tab |
| 281 | manifold branch |
| 282 | inflatable balloon |
| 283 | Luer connector |
| 284 | lumen |
| 285 | manifold |
| 286 | inflation lumen |
| 286a | inflation lumen |
| 287 | hemostasis nut/stop |
| 288 | interior wall |
| 289 | proximal end |
| 291 | Luer connection |
| 292 | region of proximal occlusion |
| 293 | proximal end |
| 294 | inflatable balloon |
| 295 | manifold branch |
| 296 | first tube or guide catheter |
| 297 | Luer fitting |
| 298a–n | inflow orifices |
| 299 | distal end |
| 300 | flow director |
| 302 | sealed region |
| 310 | single operator fluid jet thrombectomy device |
| 314 | inner catheter assembly |
| 316 | maximum safe gap |
| 318 | centering ring |
| 320 | centering ring surround |

What is claimed is:

1. A method of removing undesired obstructing matter from a body vessel or cavity having an obstruction, the method comprising the steps of:

a. providing a guidewire and an outer assembly, the outer assembly having a proximal end and a distal end and including:

(1) a manifold situated at proximal end of the outer assembly, the manifold having a proximal end and a distal end;

(2) a first tube, the first tube connected to the manifold at the distal end of the manifold and having an interior annular surface and a distal end; and, (3) an externally located stationary hemostasis nut/stop at the proximal end of the manifold;

b. advancing the first tube distally in the body vessel or cavity until the distal end of the first tube is situated proximal to the obstruction of the body vessel or cavity;

c. advancing the provided guidewire through the first tube to the obstruction;

d. providing an inner assembly comprising a second tube having a proximal end and a distal end, with a jet emanator at the distal end of the second tube, a flow director including an expandable exhaust tube proximal to the jet emanator, and further having a high pressure connection assembly at the proximal end of the second tube;

e. advancing the inner assembly to a selected position within the first tube, such that the jet emanator is spaced apart from and extends past the distal end of the first tube, and the proximal end of the flow director remains proximal to the distal end of the first tube;

f. providing a high pressure fluid supply to the second tube causing:

(1) emanating of at least one jet of fluid from the jet emanator;

(2) entraining of undesired obstructing matter from the obstruction by the at least one jet of fluid;

(3) macerating of the undesired obstructing matter subsequent entrainment by the at least one jet of fluid; and, (4) transitting of the undesired obstructing matter following entrainment and maceration through the flow director and into the first tube for removal from the body vessel or cavity by the at least one jet of fluid; and, g. providing impingement of at least one jet upon the flow director to create sufficient stagnation pressure to both expand expandable exhaust tube of the flow director against the interior annular surface of the first tube and force evacuation of undesired obstructing matter subsequent entrainment and maceration through the flow director and first tube out of the body vessel or cavity with no requirement for additional suction.

2. The method of claim 1, further comprising the step of moving the inner assembly axially relative to both the first tube and the guidewire while providing the high pressure fluid supply t o the second tube, thereby facilitating removal of the obstruction of undesired obstructing matter.

3. The method of claim 1, wherein the undesired obstructing matter is thrombus.

4. The method of claim 1, wherein the high pressure fluid supply to the jet emanator comprises saline.

5. The method of claim 1, further comprising the step of assisting the removal of the undesired obstructing matter with suction.

6. The method of claim 1, wherein the flow director has at least one inflow orifice and at least one outflow orifice, and further comprising the step of:

a. directing at least one fluid jet towards the flow director so as to create entrainment of fluid and matter to be treated into the flow director through the at least one inflow orifice, maceration of matter to be treated by the fluid jet, and a region of elevated pressure which drives at least some of the fluid and matter subsequent maceration out of the flow director through the at least one outflow orifice.

7. A method of treating matter in a body vessel or cavity comprising the steps of:

a. providing an outer catheter having a proximal end and a distal end and at least a first lumen extending along its length and a stationary stop, and an inner assembly longer than the outer catheter and having a transitional stop and a jet emanator and a flow director which pass inside the first lumen of the outer catheter and can be exchanged for an alternate inner assembly, the flow director being adapted to substantially seal against the first lumen of the outer catheter , and a guidewire;

b. advancing the outer catheter until the distal end of the outer catheter is near the matter to be treated in the body vessel or cavity;

c. inserting the inner assembly into the outer catheter and advancing the inner assembly until at least a portion of the jet emanator and at least a portion of the flow director extend past the distal end of the outer catheter, utilizing the guidewire to facilitate advancement of the outer assembly or the inner assembly and utilizing the stationary stop and the transitional stop to determine the location of the inner assembly with respect to the outer assembly; and, d. providing pressurized fluid to the jet emanator causing emanation of at least one fluid jet from the jet emanator, entrainment and maceration of the matter to be treated in the body vessel or cavity, and flow of fluid and matter subsequent maceration through the flow director and into the first lumen of the outer catheter and creating a region of elevated pressure in at least a portion of the flow director.

8. The method of claim 7 further comprising the step of:

a. removing at least some of the matter following entrainment and maceration from the body vessel or cavity by passage along the first lumen of the outer catheter.

9. The method of claim 7 wherein the flow director has at least one inflow orifice and at least one outflow orifice, and further comprising the step of:

a. directing at least one fluid jet towards the flow director so as to create entrainment of fluid and matter to be treated into the flow director through the at least one inflow orifice, maceration of matter to be treated by the fluid jet, and utilizing the region of elevated pressure to drive at least some of the fluid and matter subsequent maceration out of the flow director through the at least one outflow orifice.

10. The method of claim 7 further comprising the step of:

a. providing suction to the proximal end of the first lumen of the outer catheter to aid in the removal of fluid and matter subsequent maceration from the body vessel or cavity.

11. A method of treating matter in a body vessel or cavity comprising the steps of a. providing an outer catheter having a proximal end and a distal end and at least a first lumen extending alone its length, and an inner assembly longer than the outer catheter and having a jet emanator and a flow director which pass inside the first lumen of the outer catheter, the flow director being adapted to substantially seal against the first lumen of the outer catheter;

b. advancing the outer catheter until the distal end of the outer catheter is near the matter to be treated in the body vessel or cavity;

c. inserting the inner assembly into the outer catheter and advancing the inner assembly until at least a portion of the jet emanator and at least a portion of the flow director extend past the distal end of the outer catheter;

d. providing pressurized fluid to the jet emanator causing emanation of at least one fluid jet from the let emanator, entrainment and maceration of the matter to be treated in the body vessel or cavity, and flow of fluid and matter subsequent maceration through the flow director and into the first lumen of the outer catheter;

e. providing isolation means to prevent passage of fluid or other material past the isolation means in the body vessel or cavity; and, f. using isolation means to prevent passage of fluid or other material past the isolation means in the body vessel or cavity during at least a portion of the time that the outer catheter is positioned in the body vessel or cavity.

12. A method of treating matter in a body vessel or cavity comprising the steps of:

a. providing an outer catheter having a proximal end and a distal end and at least a first lumen extending along its length, and an inner assembly longer than the outer catheter and haying a jet emanator and a flow director which pass inside the first lumen of the outer catheter the flow director being adapted to substantially seal against the first lumen of the outer catheter;

b. advancing the outer catheter until the distal end of the outer catheter is near the matter to be treated in the body vessel or cavity;

c. inserting the inner assembly into the outer catheter and advancing the inner assembly until at least a portion of the jet emanator and at least a portion of the flow director extend past the distal end of the outer catheters; and, d. providing pressurized fluid to the jet emanator causing emanation of at least one fluid jet from the jet emanator, entrainment and maceration of the matter to be treated in the body vessel or cavity, and flow of fluid and matter subsequent maceration through the flow director and into the first lumen of the outer catheter;

e. removing the inner assembly from the outer catheter;

f. providing an alternate inner assembly and introducing the alternate inner assembly into the outer catheter; and, g. using the alternate inner assembly to aid in treatment or diagnosis in the body vessel or cavity.

13. The method of claim 12, further comprising the steps of:

a. providing isolation means to prevent passage of fluid or other material past the isolation means in the body vessel or cavity; and, b. using isolation means to prevent passage of fluid or other material past the isolation means in the body vessel or cavity at least while the inner assembly is removed and the alternate inner assembly is introduced.

14. The method of claim 12, wherein the flow director has at least one inflow orifice and at least one outflow orifice, and further comprising the step of:

a. directing at least one fluid jet towards the flow director so as to create entrainment of fluid and matter to be treated into the flow director through the at least one inflow orifice, maceration of matter to be treated by the fluid jet, and a region of elevated pressure which drives at least some of the fluid and matter subsequent maceration out of the flow director through the at least one outflow orifice.

* * * * *